(12) United States Patent
Shaughnessy et al.

(10) Patent No.: US 7,308,364 B2
(45) Date of Patent: *Dec. 11, 2007

(54) DIAGNOSIS OF MULTIPLE MYELOMA ON GENE EXPRESSION PROFILING

(75) Inventors: John D. Shaughnessy, Little Rock, AR (US); Fenghuang Zhan, Little Rock, AR (US); Bart Barlogie, Little Rock, AR (US)

(73) Assignee: The University of Arkansas for Medical Sciences, Little Rock, AR (US)

( * ) Notice: Subject to any disclaimer, the term of this patent is extended or adjusted under 35 U.S.C. 154(b) by 442 days.

This patent is subject to a terminal disclaimer.

(21) Appl. No.: 10/454,263

(22) Filed: Jun. 4, 2003

(65) Prior Publication Data

US 2004/0009523 A1 Jan. 15, 2004

Related U.S. Application Data

(63) Continuation-in-part of application No. 10/409,004, filed on Apr. 8, 2003, now abandoned, which is a continuation-in-part of application No. 10/289,746, filed on Nov. 7, 2002, now abandoned.

(60) Provisional application No. 60/403,075, filed on Aug. 13, 2002, provisional application No. 60/355,386, filed on Feb. 8, 2002, provisional application No. 60/348,238, filed on Nov. 7, 2001.

(51) Int. Cl.
*G01N 33/48* (2006.01)
*C12Q 1/68* (2006.01)
*C12P 19/34* (2006.01)
*C07H 21/04* (2006.01)

(52) U.S. Cl. .............................. 702/19; 702/20; 435/6; 435/91.2; 536/24.3

(58) Field of Classification Search ..................... None
See application file for complete search history.

(56) References Cited

OTHER PUBLICATIONS

Zhang, Y. et al. The LRP5 High-Bone-Mass G171 Mutation Disrupts LRP5 Interaction with Mesd: *Molecular and Cellular Biology*, Jun. 2004, vol. 24, No. 11, pp. 4677-4684.

Boyden, L. M. et al. High Bone Density Due to a Mutation in LDL-Receptor-Related Protein 5: *N Engl J Med*, May 16, 2002, vol. 346, No. 20, pp. 1513-1521.

Little, R.D. et al.; A Mutation in the LDL Receptor-Related Protein 5 Gene Results in the Autosomal Dominant High-Bone-Mass Trait: *Am. J. Hum. Genet.*, 2002 vol. 70, pp. 11-19.

*Primary Examiner*—Shubo (Joe) Zhou
(74) *Attorney, Agent, or Firm*—Benjamin Aaron Adler

(57) ABSTRACT

Gene expression profiling between normal B cells/plasma cells and multiple myeloma cells revealed four distinct subgroups of multiple myeloma plasma cells that have significant correlation with clinical characteristics known to be associated with poor prognosis. Diagnosis for multiple myeloma (and possibly monoclonal gammopathy of undetermined significance) based on differential expression of 14 genes, as well as prognostics for the four subgroups of multiple myeloma based on the expression of 24 genes were also established. Gene expression profiling also allows placing multiple myeloma into a developmental schema parallel to that of normal plasma cell differentiation. The development of a gene expression- or developmental stage-based classification system for multiple myeloma would lead to rational design of more accurate and sensitive diagnostics, prognostics and tumor-specific therapies for multiple myeloma.

2 Claims, 24 Drawing Sheets

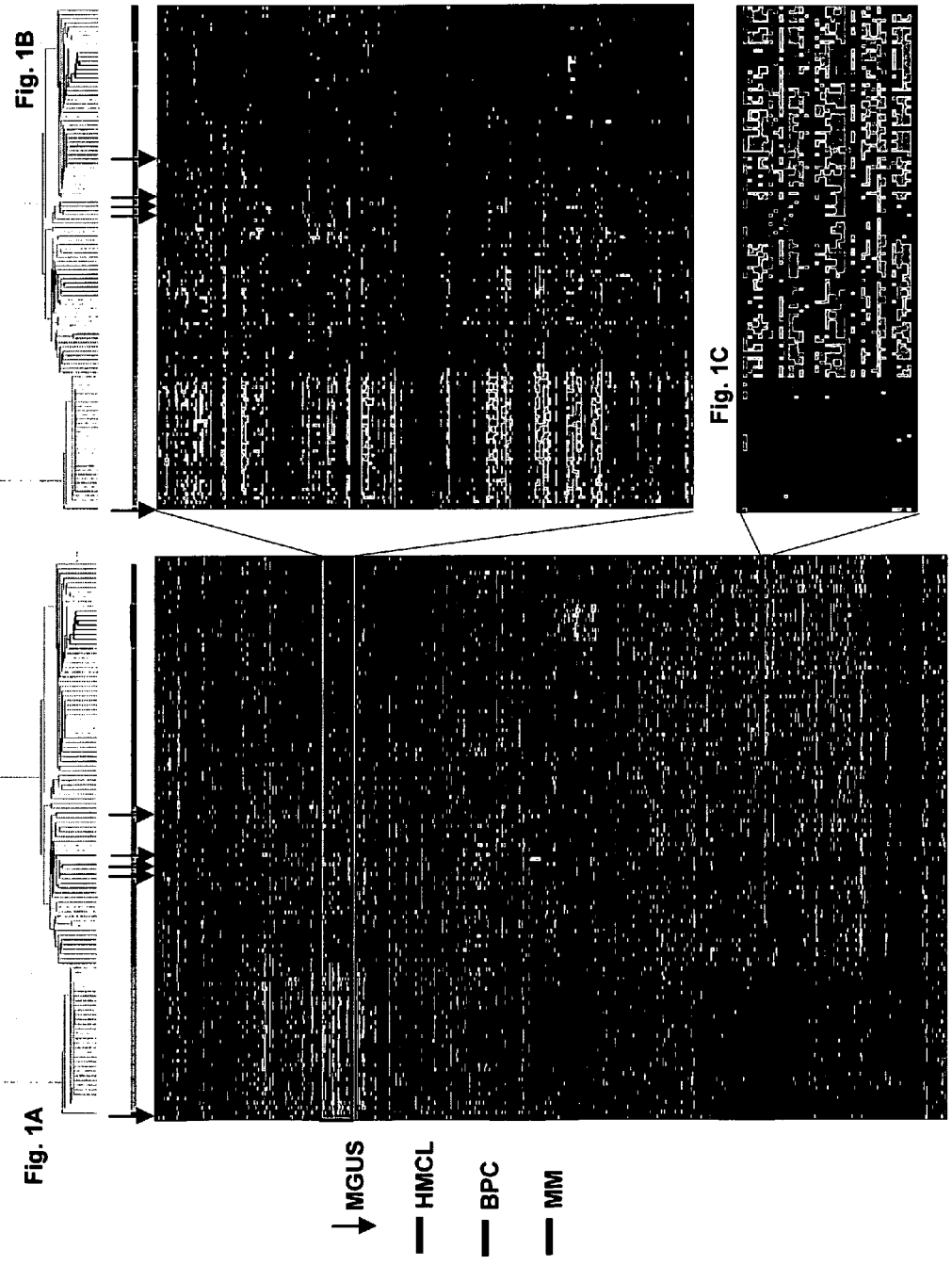

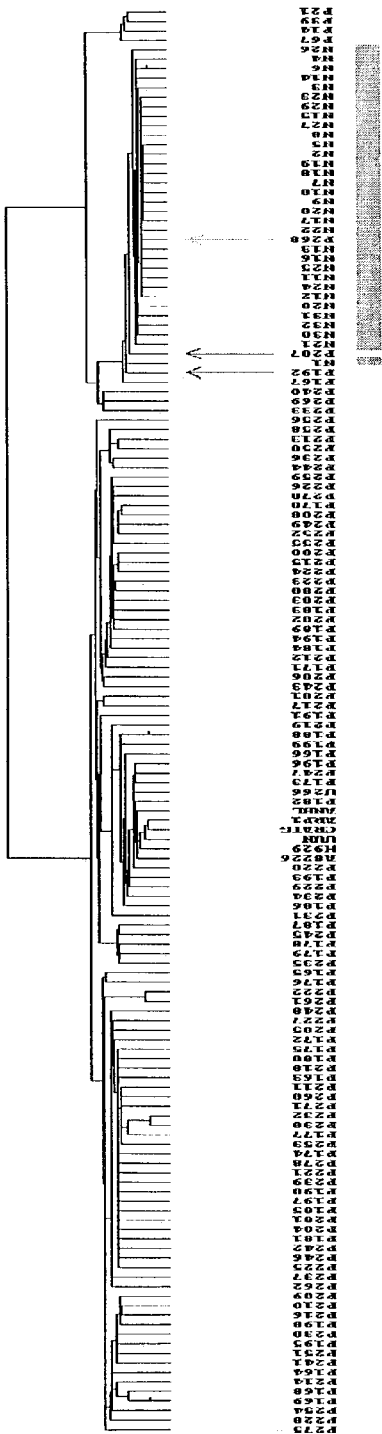
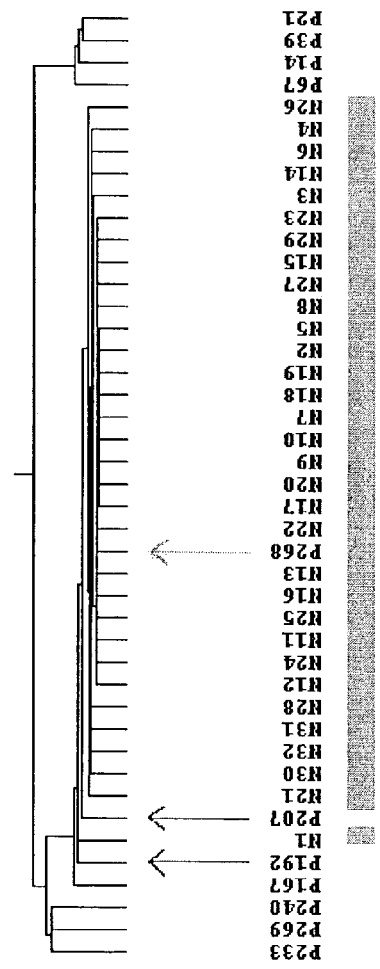
Fig. 6A
Fig. 6B

```
SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<221> NAME/KEY: primer_bind
<223> OTHER INFORMATION: primer IGJH2

<400> SEQUENCE: 1
caatggtcac cgtctcttca                                              20

<210> SEQ ID NO 2
<211> LENGTH: 22
<212> TYPE: DNA
<213> ORGANISM: Artificial Sequence
<220> FEATURE:
<221> NAME/KEY: primer_bind
<223> OTHER INFORMATION: primer MMSET

<400> SEQUENCE: 2
cctcaatttc ctgaaattgg tt                                           22
```

DIAGNOSIS OF MULTIPLE MYELOMA ON GENE EXPRESSION PROFILING

CROSS-REFERENCE TO RELATED APPLICATION

This is a continuation-in-part of U.S. Ser. No. 10/409,004, filed Apr. 8, 2003 now abandoned, which is a continuation-in-part of U.S. Ser. No. 10/289,746, filed Nov. 7, 2002, which claims benefit of provisional patent applications U.S. Ser. No. 60/348,238, filed Nov. 7, 2001, U.S. Ser. No. 60/355,386, filed Feb. 8, 2002, and U.S. Ser. No. 60/403,075, filed Aug. 13, 2002, which are all abandoned now.

FEDERAL FUNDING LEGEND

This invention was produced in part using funds obtained through a grant from the National Cancer Institute. Consequently, the federal government has certain rights in this invention.

BACKGROUND OF THE INVENTION

1. Field of the Invention

The present invention relates generally to the field of cancer research. More specifically, the present invention relates to gene expression profiling of plasma cells from patients with multiple myeloma or monoclonal gammopathy of undetermined significance.

2. Description of the Related Art

Multiple myeloma (MM) is a uniformly fatal tumor of terminally differentiated plasma cells (PCs) that home to and expand in the bone marrow. Although initial transformation events leading to the development of multiple myeloma are thought to occur at a post-germinal center stage of development as suggested by the presence of somatic hypermutation of IGV genes, progress in understanding the biology and genetics of and advancing therapy for multiple myeloma has been slow.

Multiple myeloma cells are endowed with a multiplicity of anti-apoptotic signaling mechanisms that account for their resistance to current chemotherapy and thus the ultimately fatal outcome for most patients. While aneuploidy by interphase fluorescence in situ hybridization (FISH) and DNA flow cytometry are observed in >90% of cases, cytogenetic abnormalities in this typically hypoproliferative tumor are informative in only about 30% of cases and are typically complex, involving on average 7 different chromosomes. Given this "genetic chaos" it has been difficult to establish correlations between genetic abnormalities and clinical outcomes. Only recently has chromosome 13 deletion been identified as a distinct clinical entity with a grave prognosis. However, even with the most comprehensive analysis of laboratory parameters, such as $\beta$2-microglobulin ($\beta$2M), C-reactive protein (CRP), plasma cell labeling index (PCLI), metaphase karyotyping, and FISH, the clinical course of patients afflicted with multiple myeloma can only be approximated, because no more than 20% of the clinical heterogeneity can be accounted for. Thus, there are distinct clinical subgroups of multiple myeloma and modern molecular tests may identify these entities.

Monoclonal gammopathy of undetermined significance (MGUS) and multiple myeloma are the most frequent forms of monoclonal gammopathies. Monoclonal gammopathy of undetermined significance is the most common plasma cell dyscrasia with an incidence of up to 10% of population over age 75. The molecular basis of monoclonal gammopathy of undetermined significance and multiple myeloma are not very well understood and it is not easy to differentiate the two disorders. The diagnosis of multiple myeloma or monoclonal gammopathy of undetermined significance is identical in ⅔ of cases using classification systems that are based on a combination of clinical criteria such as the amount of bone marrow plasmocytosis, the concentration of monoclonal immunoglobulin in urine or serum, and the presence of bone lesions. Especially in early phases of multiple myeloma, the differential diagnosis is associated with a certain degree of uncertainty.

Furthermore, in the diagnosis of multiple myeloma, the clinician must exclude other disorders in which a plasma cell reaction may occur such as rheumatoid arthritis and connective tissue disorders, or metastatic carcinoma where the patient may have osteolytic lesions associated with bone metastases. Therefore, given that multiple myeloma is thought to have an extended latency and clinical features are recognized many years after the development of the malignancy, new molecular diagnostic techniques are needed in screening for the disease and provide differential diagnosis for multiple myeloma, e.g., monoclonal gammopathy of undetermined significance versus multiple myeloma or the recognition of various subtypes of multiple myeloma.

Thus, the prior art is deficient in methods of differential diagnosing and identifying distinct and prognostically relevant clinical subgroups of multiple myeloma. The present invention fulfills this long-standing need and desire in the art.

SUMMARY OF THE INVENTION

Bone marrow plasma cells from 74 patients with newly diagnosed multiple myeloma, 5 with monoclonal gammopathy of undetermined significance (MGUS), and 31 normal volunteers (normal plasma cells) were purified by CD138$^+$ selection. Gene expression of purified plasma cells and 7 multiple myeloma cell lines were profiled using high-density oligonucleotide microarrays interrogating ~6,800 genes. On hierarchical clustering analysis, normal and multiple myeloma plasma cells were differentiated and four distinct subgroups of multiple myeloma (MM1, MM2, MM3 and MM4) were identified. The expression patterns of MM1 was similar to normal plasma cells and monoclonal gammopathy of undetermined significance, whereas MM4 was similar to multiple myeloma cell lines. Clinical parameters linked to poor prognosis such as abnormal karyotype (P=0.0003) and high serum $\beta$2-microglobulin levels (P=0.0004) were most prevalent in MM4. Genes involved in DNA metabolism and cell cycle control were overexpressed in a comparison of MM1 and MM4.

Using chi square and Wilcoxon rank sum tests, 120 novel candidate disease genes that discriminated between normal and malignant plasma cells (P<0.0001) were identified. Many of these candidate genes are involved in adhesion, apoptosis, cell cycle, drug resistance, growth arrest, oncogenesis, signaling and transcription. In addition, a total of 156 genes, including FGFR3 and CCND1, exhibited highly elevated ("spiked") expression in at least 4 of the 74 multiple myeloma cases (range of spikes: 4 to 25). Elevated expression of FGFR3 and CCND1 were caused by the translocation t(4;14)(p16;q32) or t(11;14)(q13;q32).

The present invention also identifies, through multivariate stepwise discriminant analysis, a minimum subset of genes whose expression is intimately associated with the malignant features of multiple myeloma. Fourteen genes were defined as predictors that are able to differentiate plasma cells of multiple myeloma patients from normal plasma cells with a high degree of accuracy, and 24 genes were identified as predictors that are able to differentiate the distinct subgroups of multiple myeloma (MM1, MM2, MM3 and MM4) described herein.

Furthermore, data disclosed herein indicated that multiple myeloma can be placed into a developmental schema parallel to that of normal plasma cell differentiation. Based on gene expression profiling, the MM4, MM3 and MM2 subgroups described above were found to have similarity with tonsil B cells, tonsil plasma cells and bone marrow plasma cells respectively. These data suggest that the enigmatic multiple myeloma is amendable to a gene expression/development stage-based classification system.

The present invention of gene expression profiling using DNA microarray and hierarchical clustering analysis can be used to classify subgroups of multiple myeloma, identify genes with differential expression in subsets of multiple myeloma patients, and identify potential therapeutic targets for multiple myeloma. For example, there are provided methods of diagnosis for multiple myeloma or subgroups of multiple myeloma based on the expression of a group of 14 genes or a group of 24 genes respectively.

In another aspect of the present invention, there are provided methods of treatment for multiple myeloma. Such methods involve inhibiting or enhancing the expression of genes that are found to be over-expressed or down-regulated respectively in multiple myeloma patients as disclosed herein.

The present invention also provides a method of developmental stage-based classification for multiple myeloma that is based on gene expression profiling between multiple myeloma cells and normal B or plasma cells and the present invention also provides a method of controlling bone loss in an individual, comprising the step of inhibiting the expression of the DKK1 gene (accession number NM012242) or the activity of the protein expressed by the DKK1 gene.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

FIG. 1A shows cluster-ordered data table. The clustering is presented graphically as a colored image. Along the vertical axis, the analyzed genes are arranged as ordered by the clustering algorithm. The genes with the most similar patterns of expression are placed adjacent to each other. Likewise, along the horizontal axis, experimental samples are arranged; those with the most similar patterns of expression across all genes are placed adjacent to each other. Both sample and gene groupings can be further described by following the solid lines (branches) that connect the individual components with the larger groups. The color of each cell in the tabular image represents the expression level of each gene, with red representing an expression greater than the mean, green representing an expression less than the mean, and the deeper color intensity representing a greater magnitude of deviation from the mean.

FIG. 1B shows an amplified gene cluster showing genes downregulated in MM. Most of the characterized and sequence-verified cDNA-encoded genes are known to be immunoglobulins.

FIG. 1C shows a cluster enriched with genes whose expression level was correlated with tumorigenesis, cell cycle, and proliferation rate. Many of these genes were also statistically significantly upregulated in multiple myeloma ($\chi^2$ and WRS test) (see Table 5).

FIG. 6A shows 269 cases of multiple myeloma, 7 multiple myeloma cell lines, 7 monoclonal gammopathy of undetermined significance and 32 normal plasma cells samples clustered based on the correlation of 5,483 genes (probe sets). Two major branches contained two distinct cluster groups. The subgroup including normal plasma cell samples contained 1 monoclonal gammopathy of undetermined significance (green arrow) and 2 misclassified multiple myeloma samples (pink arrow). FIG. 6B shows amplified sample cluster showing samples connecting to the normal group.

CD19-Selected Tonsil B cells: Tonsil-derived mononuclear fractions were tested for percentage of tonsil B cells prior to anti-CD19 immunomagnetic bead sorting by using two-color FACs analysis with antibodies to CD20/CD38 (a and b). The post-sorting purity of the tonsil B cell sample was determined by CD20/CD38 (c and d), CD138/CD20 (e), and CD138/CD38 (f) staining. Cytospin preparations of the purified tonsil B cell samples were stained with Wright Giemsa and cell morphology observed with light microscopy (g). Purifed B cells were also stained with AMCA and FITC antibodies against cytoplasmic immunoglobulin (cIg) light chain κ and λ and observed by immunofluorescence microscopy (h). Note the lack of cIg staining and thus minimal plasma cell contamination in the tonsil B cell fraction.

CD 138-Selected Tonsil Plasma Cells: Tonsil mononuclear fractions were tested for percentage of plasma cells prior to anti-CD138 immunomagnetic bead sorting by using two color FACs analysis using antibodies to CD38/CD45 (i) and CD138/CD45 (j). The post-sorting purity of the tonsil plasma cell samples was determined by dual color FACs analysis of CD38/CD45 (k), CD138/CD45 (l), CD38/CD20 (m), and CD138/CD38 (n). Cytospin preparations of the purified tonsil plasma cells were analyzed for morphological appearance (o) and cIg (p).

CD 138-Selected Bone Marrow Plasma Cells: Mononuclear fractions from bone marrow aspirates were tested for percentage of plasma cells prior to anti-CD138 immunomagnetic bead sorting by using two color FACs analysis using antibodies to CD38/CD45 (q) and CD138/CD45 (r). The post sorting purity of the bone marrow plasma cell sample was determined by dual color FACs analysis of CD38/CD45 (s), CD138/CD45 (t), CD38/CD20 (u), and CD138/CD38 (v). Cytospin preparations of the purified bone marrow plasma cells were analyzed for morphological appearance (w) and cIg (x). Note the high percentage of cIg-positive bone marrow plasma cells with clear plasma cell morphologic characteristics.

Figure 11:
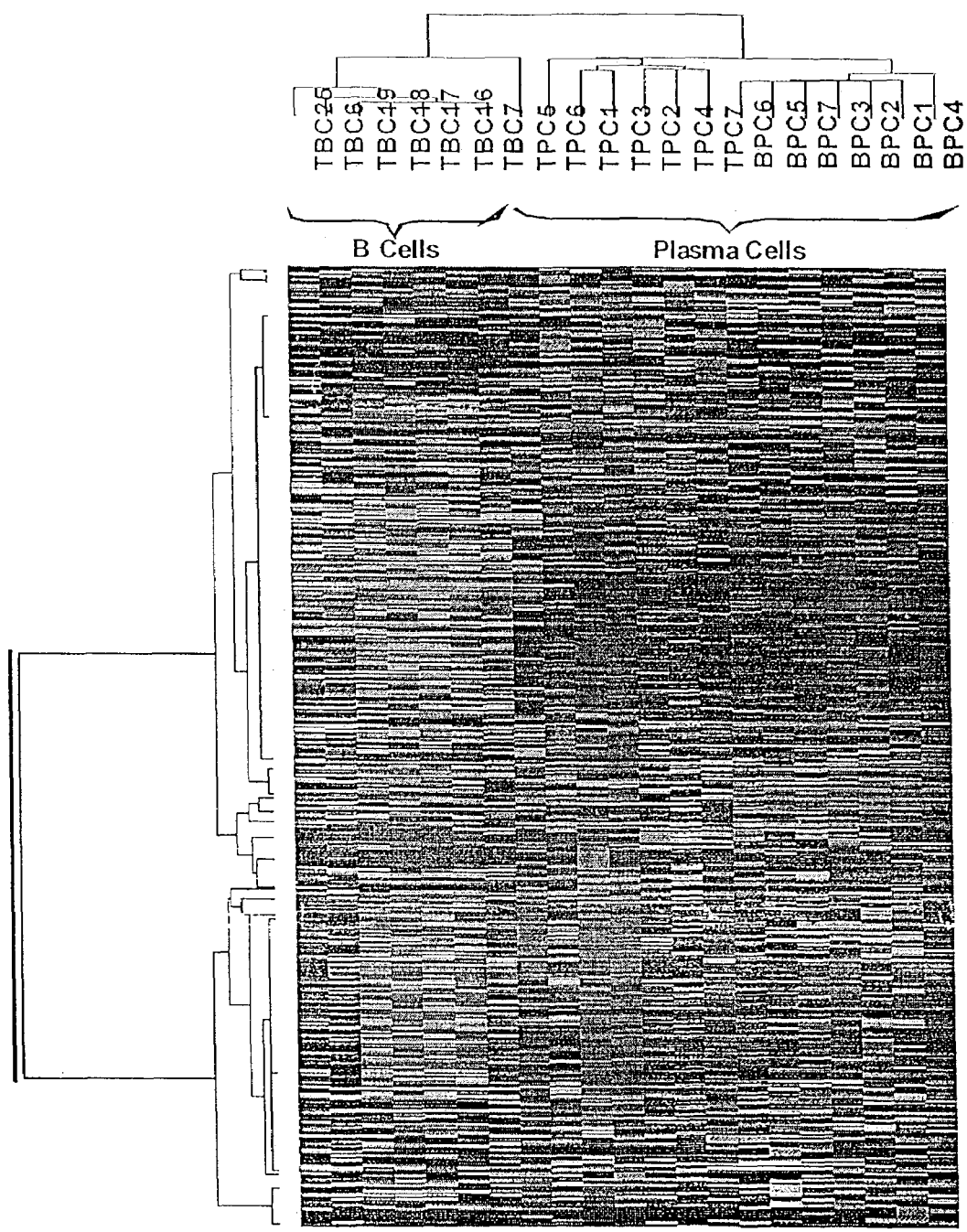

FIG. 11 shows two-dimensional hierarchical cluster analysis of normal human plasma cells. Included were 7 tonsil BC (TBC), 7 tonsil PC (TPC), and 7 bone marrow PC (BPC) samples clustered based on the correlation of experimental expression profiles of 4866 probe sets. The clustering is presented graphically as a colored image. Along the vertical axis, the analyzed genes are arranged as ordered by the clustering algorithm. The genes with the most similar patterns of expression are placed adjacent to each other. Experimental samples are similarly arranged in the horizontal axis. The color of each cell in the tabular image represents the expression level of each gene, with red representing an expression greater than the mean, green representing an expression less than the mean, and the deeper color intensity representing a greater magnitude of deviation from the mean. The top dendrogram produces two major branches separating tonsil BCs from PCs. In addition, within the PC cluster, tonsil PCs and bone marrow PCs are separated on three unique branches.

Figure 12:
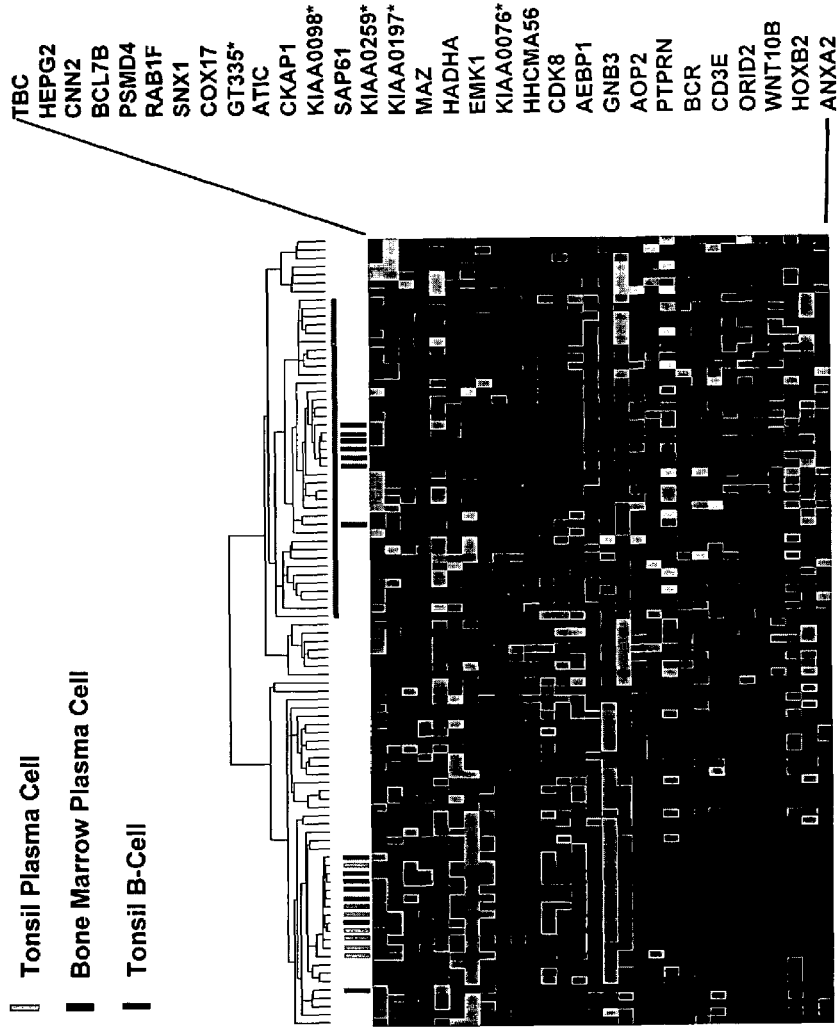

FIG. 12 shows two-dimensional hierarchical cluster analysis of experimental expression profiles and gene behavior of 30 EDG-MM. B cells, tonsil and bone marrow plasma cells, and multiple myeloma (MM) samples were analyzed using a cluster-ordered data table. The tonsil B cell, tonsil plasma cell, bone marrow plasma cell samples are indicated by red, blue, and golden bars respectively. The nomenclature for the 74 MM samples is as indicated in Zhan et al. (2002a). Along the vertical axis, the analyzed genes are arranged as ordered by the clustering algorithm. The genes with the most similar patterns of expression are placed adjacent to each other. Both sample and gene groupings can be further described by following the solid lines (branches) that connect the individual components with the larger groups. The tonsil B cell cluster is identified by the horizontal red bar. The color of each cell in the tabular image represents the expression level of each gene, with red representing an expression greater than the mean, green representing an expression less than the mean, and the deeper color intensity representing a greater magnitude of deviation from the mean.

Figure 13:
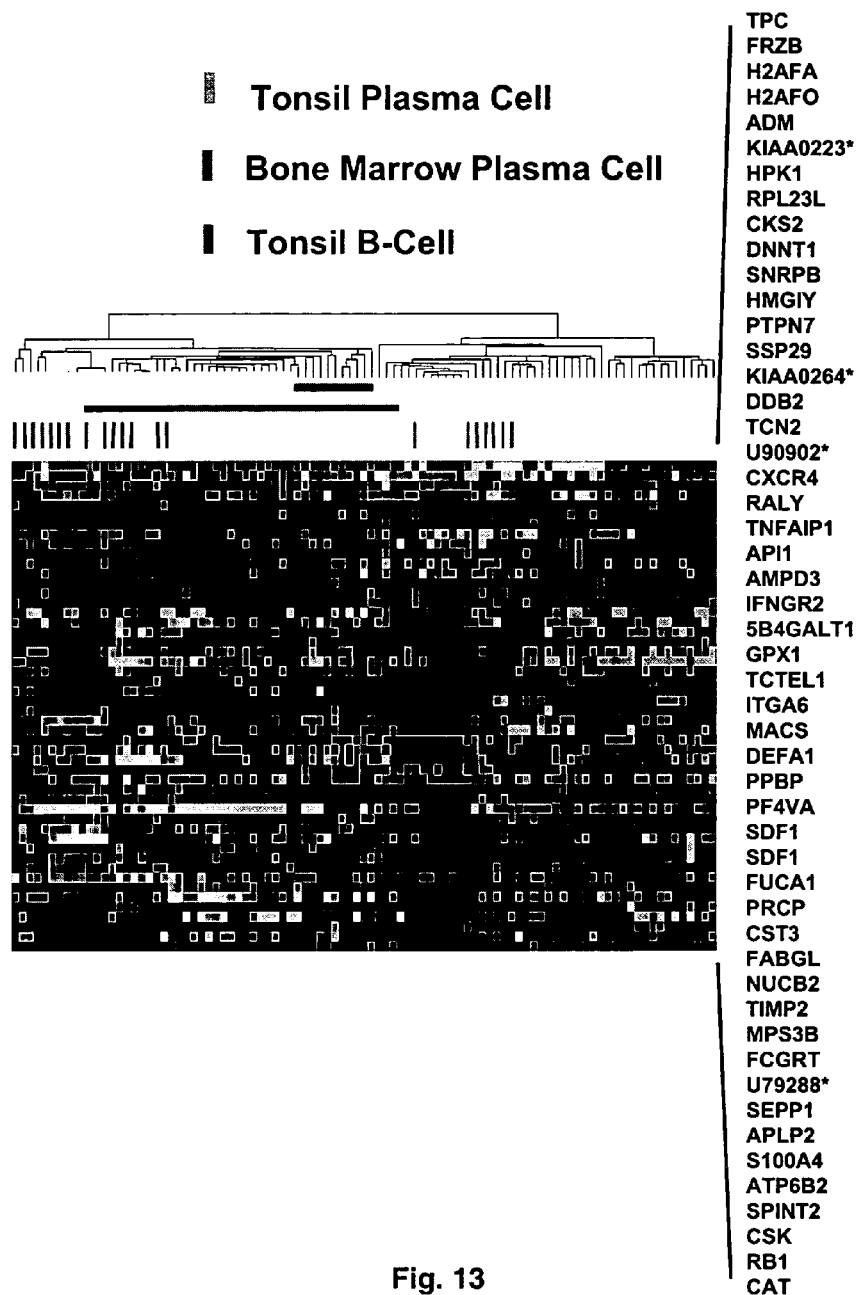

FIG. 13 shows two-dimensional hierarchical cluster analysis of experimental expression profiles and gene behavior of 50 LDG-MM1 genes. Genes are plotted along the vertical axis (right side), and experimental samples are plotted along the top horizontal axis by their similarity. The tonsil plasma cell cluster is identified by a horizontal blue bar. Tonsil B cell, tonsil plasma cell, and bone marrow plasma cell samples are indicated as in FIG. 12.

Figure 14:
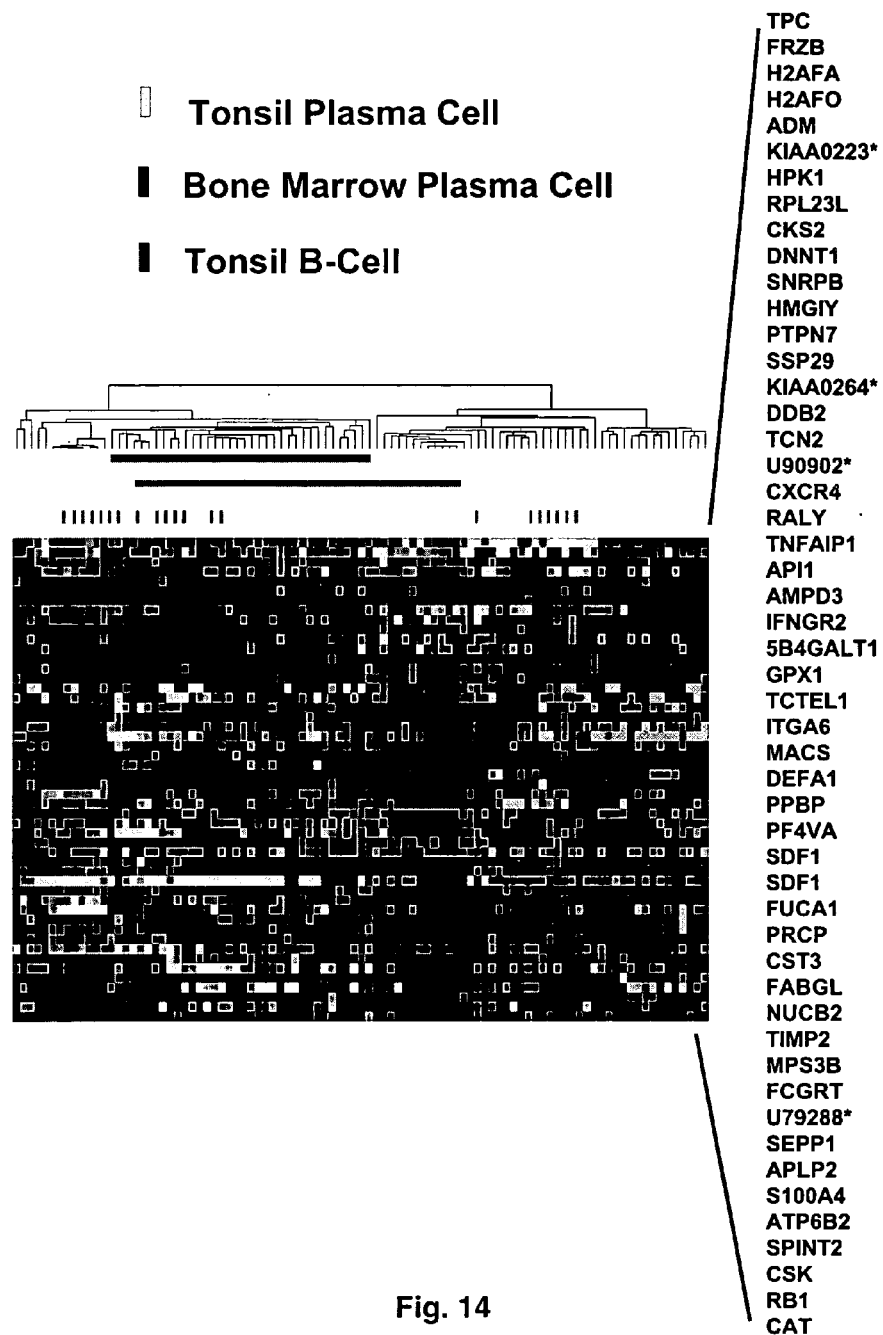

FIG. 14 shows two-dimensional hierarchical cluster analysis of experimental expression profiles and gene behavior of 50 LDG-MM2 genes. Genes are plotted along the vertical axis (right side), and experimental samples are plotted along the top horizontal axis by their similarity. The bone marrow plasma cell cluster is identified by a horizontal golden bar. Tonsil B cell, tonsil plasma cell, and bone marrow plasma cell samples are indicated as in FIG. 12.

Figure 15:
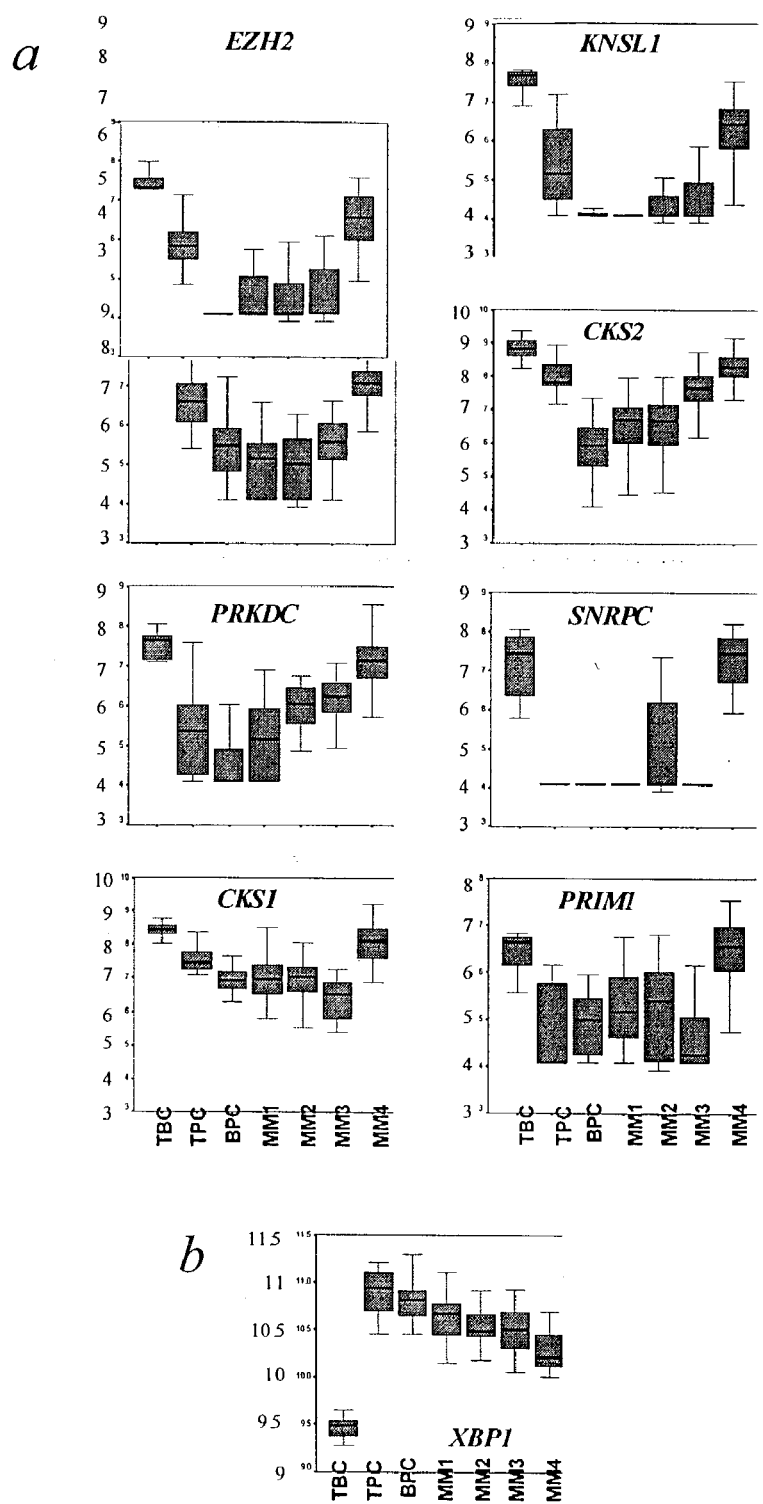

FIG. 15 shows variation in expression of proliferation genes reveals similarities between tonsil B cells and MM4. The data are shown as boxplot of Kruskal-Wallis test values. The seven groups analyzed (tonsil B cells, tonsil plasma cells, bone marrow plasma cells, and gene expression defined subgroups MM1, MM2, MM3, and MM4) are distributed along the x-axis and the natural log transformed average difference is plotted on the y axis. EZH2; $P=7.61 \times 10^{-11}$; KNSL1, $P=3.21 \times 10^{-8}$; PRKDC, $P=2.86 \times 10^{-11}$; SNRPC, $P=5.44 \times 10^{-12}$; CCNB1, $P=2.54 \times 10^{-8}$; CKS2, $P=9.49 \times 10^{-11}$; CKS1, $P=5.86 \times 10^{-9}$; PRIM1, $P=4.25 \times 10^{-5}$.

Figure 16:
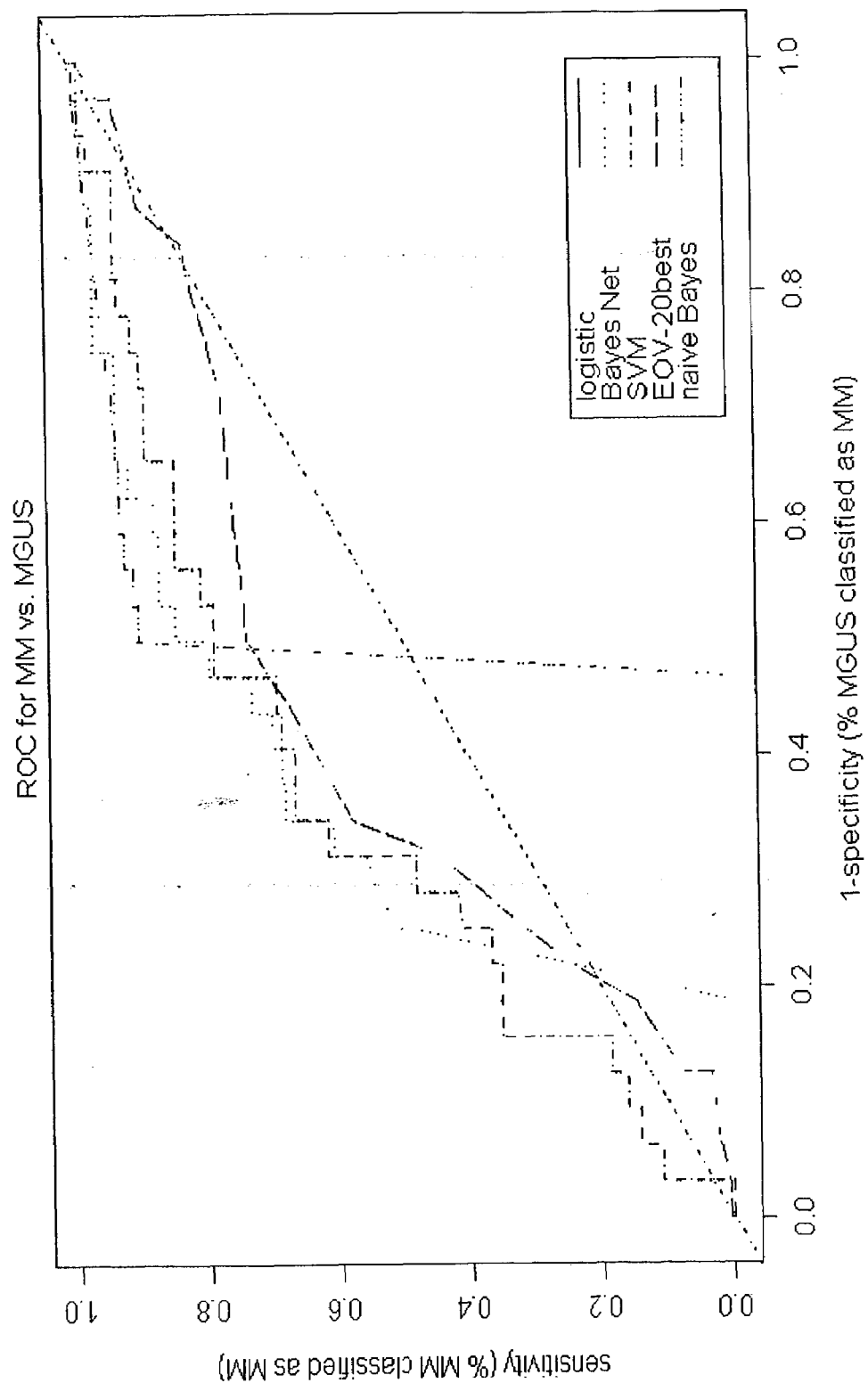

FIG. 16 shows the receiver operating characteristic (ROC) curves for the multiple myeloma (MM) vs monoclonal gammopathy of undetermined significance (MGUS) classification.

Figure 17A:
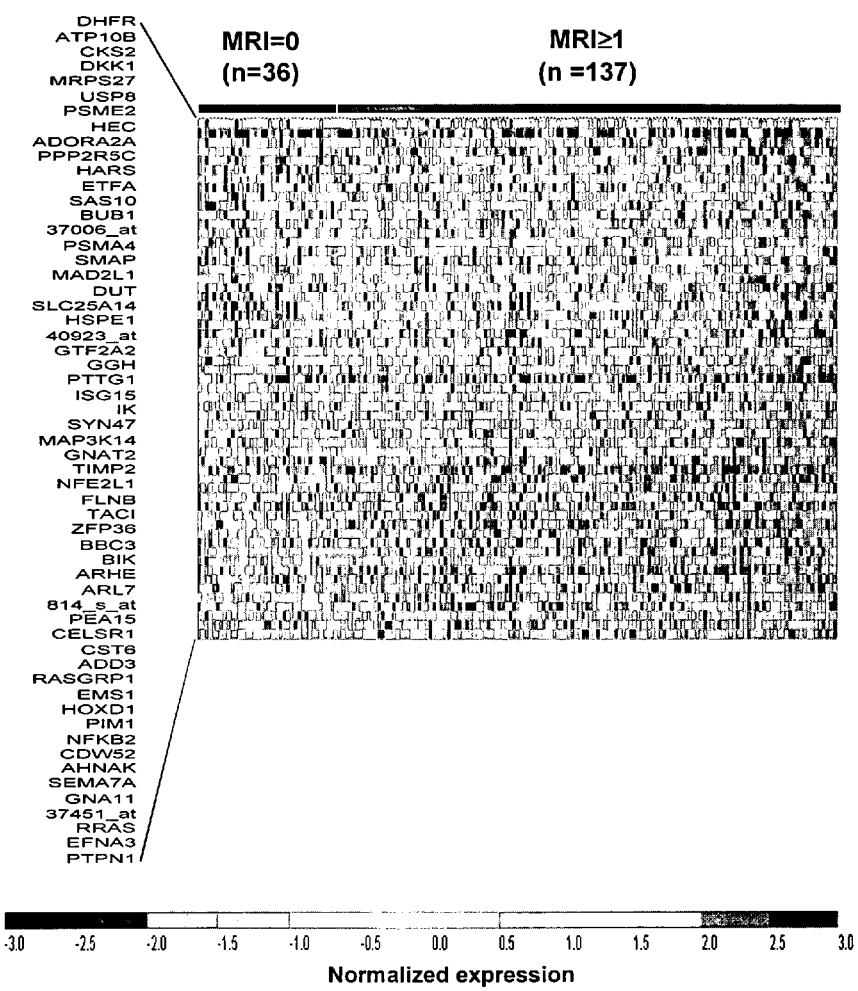

FIG. 17A shows global gene expression patterns reflect bone lesions in multiple myeloma. Clusterview of normalized expression levels of 58 genes identified by logistic regression and permutation analysis as being significantly differentially expressed in malignant plasma cells from patients with 0 (n=36) and 1+ MRI focal lesions (n=137) (P<0.0001). The 28 genes exhibiting overexpression in plasma cells from patients with 1+ MRI lesions are ordered from top to bottom based on the significance rank. Likewise the 30 genes showing significant elevation in patients with no MRI-lesions are ordered from bottom to top based on significance rank. Expression scales range from −3 (blue) to +3 (red) as indicated below the data display. DKK1 ranked 4th in significance.

Figure 17B:
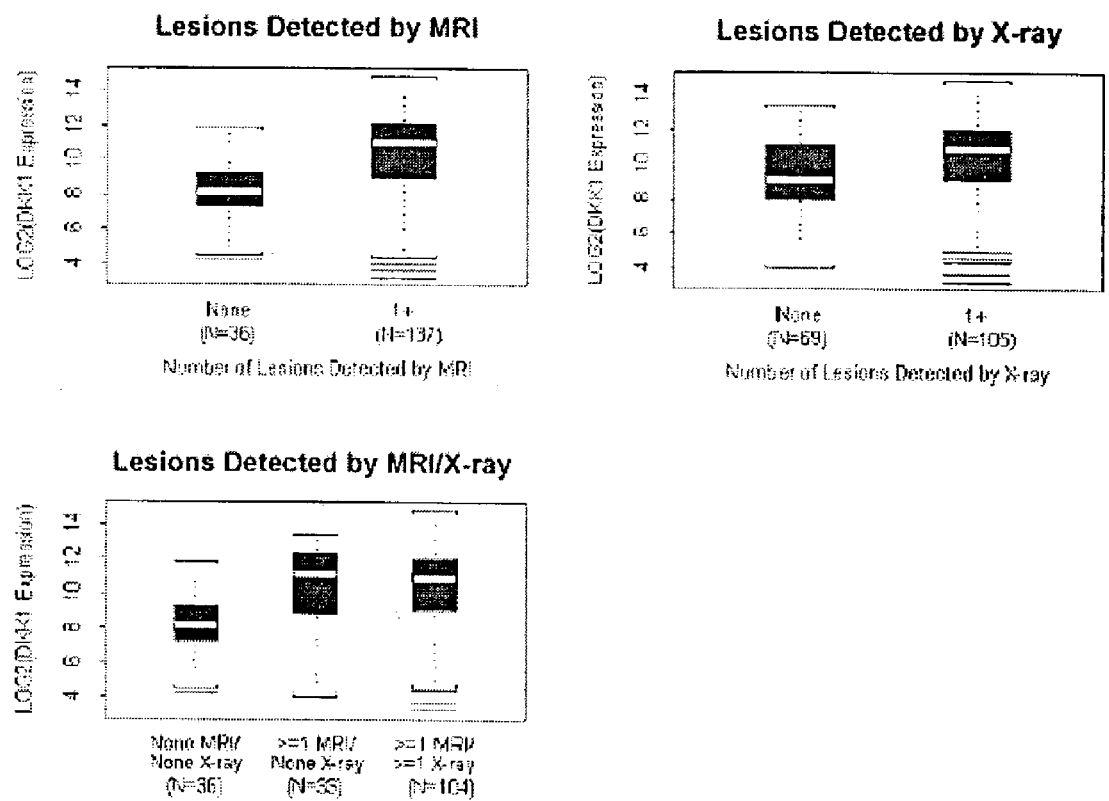

FIG. 17B shows Log 2 DKK1 expression was correlated with bone lesions. Box plots of DKK1 gene expression levels in purified plasma cells in relation to lesions detected by MRI, x-ray, and MRI and xray. Odds ratios for relative risk and associated p values are presented in the text.

Figure 18:
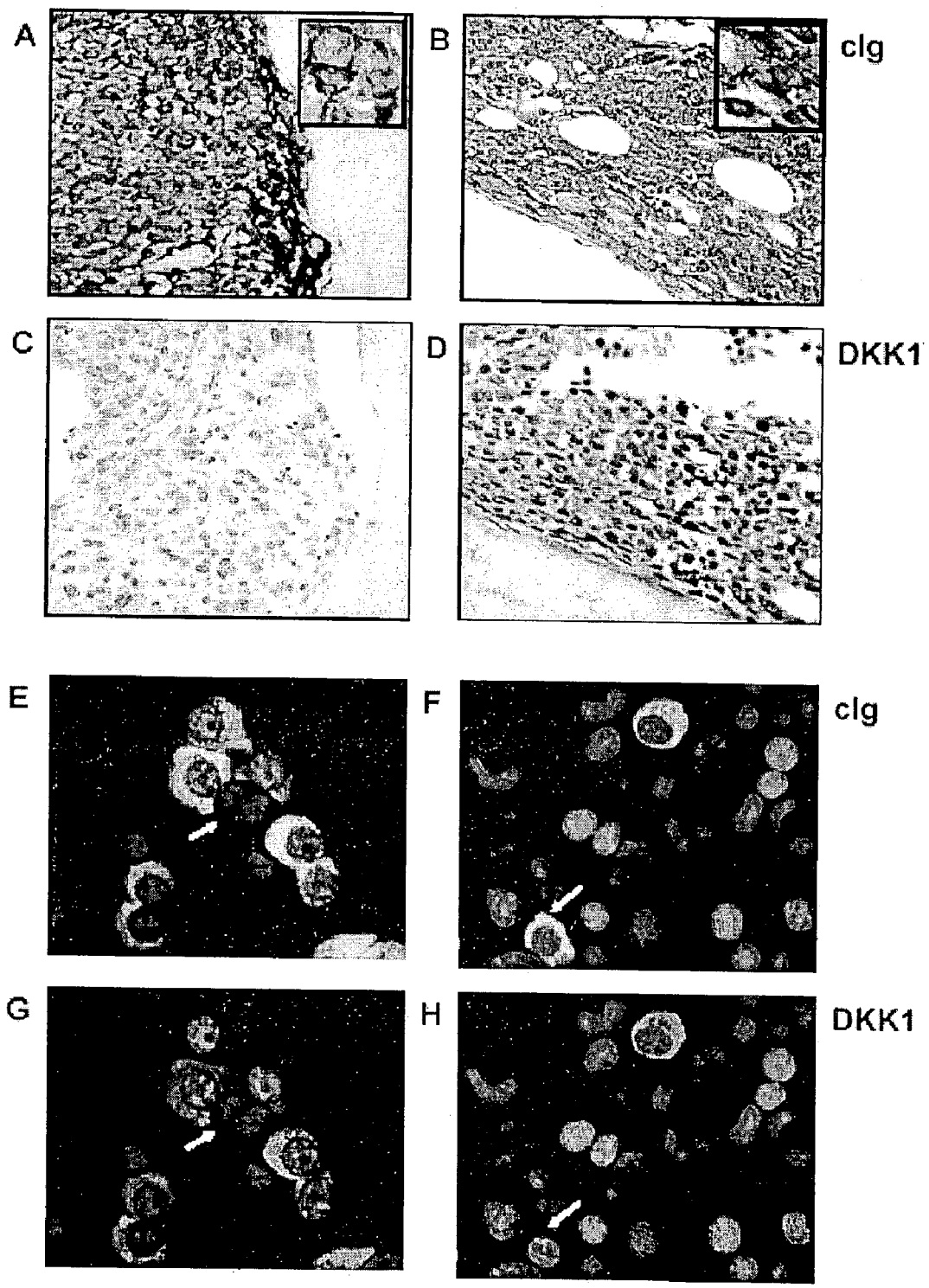

FIG. 18 shows DKK1 protein expression is restricted to plasma cells in the bone marrow. Expression of DKK1 and cytoplasmic immunoglobulin (cIg) kappa or lambda light chain was examined by immunohistochemistry (A-D) and immunofluorescence (E-H) staining of bone marrow biopsies and bone marrow aspirates, respectively. DKK1 protein expression in representative examples from a patient with low (A, C) and high (B, D) DKK1 gene expression are correlated. A, B, E, and F are stained for cIg; C, D, G, and H are stained for DKK1. Note that both biopsies (A and B) stain brightly for cIg, but only the case with high DKK1 gene expression (B) shows DKK1 protein expression (D). All images are at 250× magnification. Immunofluorescence staining was performed on mononuclear cells from bone marrow aspirates of a multiple myeloma patient (E and G) and a normal healthy donor (F and H). Note that only plasma cells stain for DKK1 in both multiple myeloma and normal bone marrow (arrows, E and G, indicate neutrophil nuclear morphology). Also note that not all plasma cells in normal marrow (F and H) are DKK1 positive (see arrows). All images are at 1000× magnification.

Figure 19:
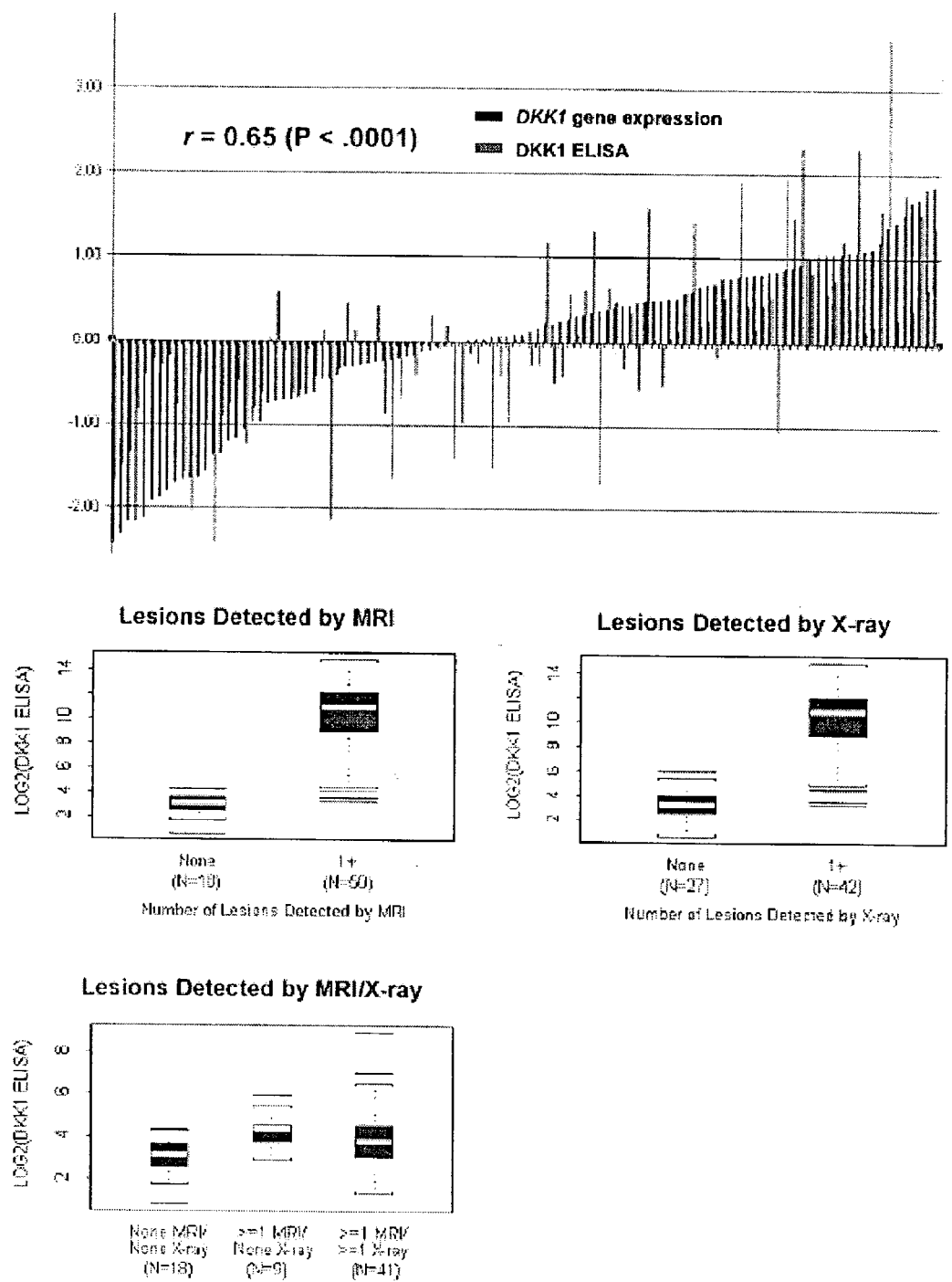

FIG. 19 shows DKK1 protein in the serum is highly correlated with DKK1 gene expression and the presence of bone lesions. FIG. 19A shows the expression of DKK1 mRNA and proteins detected by microarray and ELISA respectively and both of the results were transformed by the log base 2 and normalized to give a mean of 0 and variance of 1. Each bar indicates the relative relationship between each sample. There was a strong significant correlation between DKK1 transcripts and protein (r=0.65, p<0.0001). FIG. 19B shows box plots of bone marrow serum DKK1 protein levels in relation to lesions detected by MRI, x-ray, and MRI and x-ray. Odds ratios for relative risk and associated p values are presented in the text.

Figure 20:
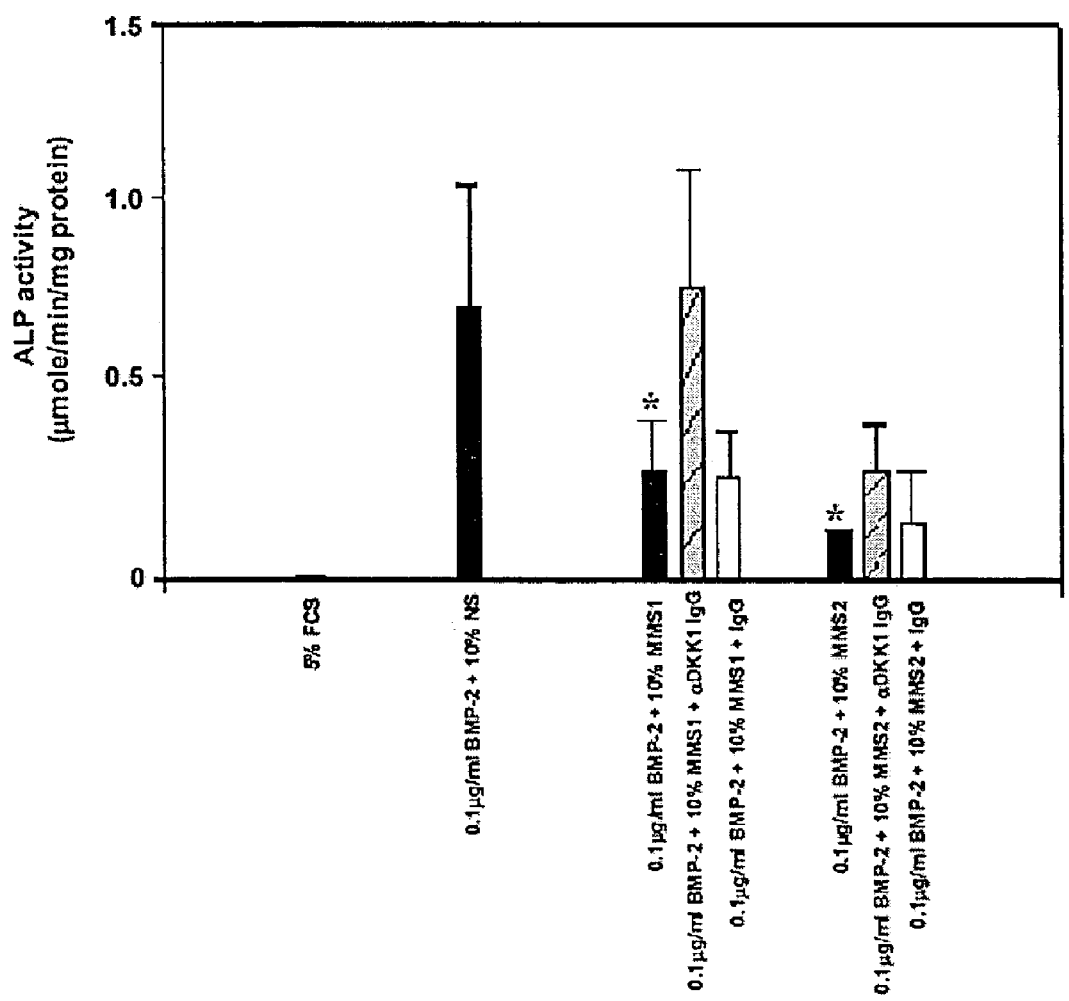

FIG. 20 shows multiple myeloma serum can block alkaline phosphatase production in BMP-2 treated C2C12 cells in a DKK1-dependent manner. Twenty thousand C2C12 cells were cultured for 5 days in the presence of 100 ng/ml BMP2, BMP2+10% normal bone marrow serum (NS), BMP2+10% multiple myeloma bone marrow serum from 2 patients (MMS1 and MMS2), or BMP2+10% multiple myeloma patient serum after pre-incubation with goat anti-DKK1 or goat polyclonal IgG 30 minutes at RT. Alkaline phosphatase levels were determined and each bar represents the mean±SEM) of triplicate determinants. Data were analyzed by Wilcoxon test after establishing homogeneity of variances. * Indicates p<0.05 in comparison to ALP in BMP2+10% normal serum.

DETAILED DESCRIPTION OF THE INVENTION

There is now strong evidence that global gene expression profiling can reveal a molecular heterogeneity of similar or related hematopoietic malignancies that have been difficult to distinguish. The most significantly differentially expressed genes in a comparison of normal and malignant cells can be used in the development of clinically relevant diagnostics as well as provide clues into the basic mechanisms of cellular transformation. In fact, these profiles might even be used to identify malignant cells even in the absence of any clinical manifestations. In addition, the biochemical pathways in which the products of these genes act may be targeted by novel therapeutics.

The present invention demonstrates that both normal and malignant plasma cells can be purified to homogeneity from bone marrow aspirates using anti-CD138-based immunomagnetic bead-positive selection. Using these cells, the present invention provides the first comprehensive global gene expression profiling of newly diagnosed multiple myeloma patients and contrasted these expression patterns with those of normal plasma cells. Novel candidate multiple myeloma disease genes were identified using the method of gene expression profiling disclosed herein and this profiling has lead to the development of a gene-based classification system for multiple myeloma.

Results from hierarchical cluster analysis on multiple myeloma and normal plasma cells, as well as the benign plasma cell dyscrasia monoclonal gammopathy of undetermined significance and the end-stage-like multiple myeloma cell lines revealed normal plasma cells are unique and that primary multiple myeloma is either like monoclonal gammopathy of undetermined significance or multiple myeloma cell lines. In addition, multiple myeloma cell line gene expression was homogeneous as evidenced by the tight clustering in the hierarchical analysis. The similarity of multiple myeloma cell line expression patterns to primary newly diagnosed forms of multiple myeloma support the validity of using multiple myeloma cell lines as models for multiple myeloma.

Upon hierarchical clustering of multiple myeloma alone, four distinct clinical multiple myeloma subgroups (MM1 to MM4) were distinguished. The MM1 subgroup contained samples that were more like monoclonal gammopathy of undetermined significance, whereas the MM4 subgroup contained samples more like multiple myeloma cell lines. The most significant gene expression patterns differentiating MM1 and MM4 were cell cycle control and DNA metabolism genes, and the MM4 subgroup was more likely to have abnormal cytogenetics, elevated serum β2M, elevated creatinine, and deletions of chromosome 13. These are important variables that historically have been linked to poor prognosis.

Gene Expression Changes in Multiple Myeloma

Data disclosed herein indicated that the MM4 subgroup likely represents the most high-risk clinical entity. Thus, knowledge of the molecular genetics of this particular subgroup should provide insight into its biology and possibly provide a rationale for appropriate subtype-specific therapeutic interventions. The most significant gene expression changes differentiating the MM1 and MM4 subgroups code for activities that clearly implicate MM4 as having a more proliferative and autonomous phenotype. The most significantly altered gene in the comparison, TYMS (thymidylate synthase), which functions in the prymidine biosynthetic pathway, has been linked to resistance to fluoropyrimidine chemotherapy and also poor prognosis in colorectal carcinomas. Other notable genes upregulated in MM4 were the CAAX farnesyltransferase gene, FTNA. Farnesyltransferase prenylates RAS, a post translational modification required to allow RAS to attach to the plasma membrane. These data suggest that farnesyltransferase inhibitors may be effective in treating patients with high levels of FTNA expression.

Two other genes coding for components of the proteasome pathway, POH1 (26S proteasome-associated pad1 homolog) and UBL1 (ubiquitin-like protein 1) were also overexpressed in MM4. Overexpression of POH1 confers P-glycoprotein-independent, pleotropic drug resistance to mammalian cells. UBL1, also known as sentrin, is involved in many processes including associating with RAD51, RAD52, and p53 proteins in the double-strand repair pathway; conjugating with RANGAP 1 involved in nuclear protein import; and importantly for multiple myeloma, protecting against both Fas/Apo-1 (TNFRSF6) or TNFR1-induced apoptosis. In contrast to normal plasma cells, more than 75% of multiple myeloma plasma cells express abundant mRNA for the multidrug resistance gene, lung-resistance-related protein (MVP). These data are consistent with previous reports showing that expression of MVP in multiple myeloma is a poor prognostic factor. Given the uniform development of chemotherapy resistance in multiple myeloma, the combined overexpression of POH1 and MVP may have profound influences on this phenotype. The deregulated expression of many genes whose products function in the proteasome pathway may be used in the pharmacogenomic analysis of efficacy of proteasome inhibitors like PS-341 (Millennium Pharmaceuticals, Cambridge, Mass.).

Another significantly upregulated gene in MM4 was the single stranded DNA-dependent ATP-dependent helicase (G22P1), which is also known as Ku70 autoantigen. The DNA helicase II complex, made up of p70 and p80, binds preferentially to fork-like ends of double-stranded DNA in a cell cycle-dependent manner. Binding to DNA is thought to be mediated by p70 and dimerization with p80 forms the ATP-dependent DNA-unwinding enzyme (helicase II) and acts as the regulatory component of a DNA-dependent protein kinase (DNPK) which was also significantly upregulated in MM4. The involvement of the helicase II complex in DNA double-strand break repair, V(D)J recombination, and notably chromosomal translocations has been proposed. Another gene upregulated was the DNA fragmentation factor (DFFA). Caspase-3 cleaves the DFFA-encoded 45 kD subunit at two sites to generate an active factor that produces DNA fragmentation during apoptosis signaling. In light of the many blocks to apoptosis in multiple myeloma, DFFA activation could result in DNA fragmentation, which in turn would activate the helicase II complex that then may facilitate chromosomal translocations. It is of note that abnormal karyotypes, and thus chromosomal translocations, are associated with the MM4 subgroup which tended to overexpress these two genes.

Hence, results disclosed herein demonstrate that direct comparison of gene expression patterns in multiple myeloma and normal plasma cells can identified novel genes that could represent the fundamental changes associated with the malignant transformation of plasma cells.

The progression of multiple myeloma as a hypoproliferative tumor is thought to be linked to a defect in programmed cell death rather than rapid cell replication. Two genes, prohibitin (PHB) and quiescin Q6 (QSCN6), overexpressed in multiple myeloma are involved in growth arrest. The overexpression of these genes may be responsible for the typically low proliferation indices seen in multiple myeloma. It is hence conceivable that therapeutic downregulation of these genes that results in enhanced proliferation could render multiple myeloma cells more susceptible to cell cycle-active chemotherapeutic agents.

The gene coding for CD27, TNFRSF7, the second most significantly underexpressed gene in multiple myeloma, is a member of the tumor necrosis factor receptor (TNFR) superfamily that provides co-stimulatory signals for T and B cell proliferation and B cell immunoglobulin production and apoptosis. Anti-CD27 significantly inhibits the induction of Blimp-1 and J-chain transcripts which are turned on in cells committed to plasma cell differentiation, suggesting that ligation of CD27 on B cells may prevent terminal differentiation. CD27 ligand (CD70) prevents IL-10-mediated apoptosis and directs differentiation of $CD27^+$ memory B cells toward plasma cells in cooperation with IL-10. Thus, it is possible that the downregulation of CD27 gene expression in multiple myeloma may block an apoptotic program.

The overexpression of CD47 on multiple myeloma may be related to escape of multiple myeloma cells from immune surveillance. Studies have shown that cells lacking CD47 are rapidly cleared from the bloodstream by splenic red pulp macrophages and CD47 on normal red blood cells prevents this elimination.

The gene product of DNA methyltransferase 1, DNMT1, overexpressed in multiple myeloma, is responsible for cytosine methylation in mammals and has an important role in epigenetic gene silencing. In fact, aberrant hypermethylation of tumor suppressor genes plays an important role in the development of many tumors. De novo methylation of p16/INK4a is a frequent finding in primary multiple myeloma. Also, recent studies have shown that upregulated expression of DNMTs may contribute to the pathogenesis of leukemia by inducing aberrant regional hypermethylation. DNA methylation represses genes partly by recruitment of the methyl-CpG-binding protein MeCP2, which in turn recruits a histone deacetylase activity. It has been shown that the process of DNA methylation, mediated by Dnmt1, may depend on or generate an altered chromatin state via histone deacetylase activity. It is potentially significant that multiple myeloma cases also demonstrate significant overexpression of the gene for metastasis-associated 1 (MTA1). MTA1 was originally identified as being highly expressed in metastatic cells. MTA1 has more recently been discovered to be one subunit of the NURD (NUcleosome Remodeling and histone Deacetylation) complex which contains not only ATP-dependent nucleosome disruption activity, but also histone deacetylase activity. Thus, over expression of DNMT1 and MTA1 may have dramatic effects on repressing gene expression in multiple myeloma.

Oncogenes activated in multiple myeloma included ABL and MYC. Although it is not clear whether ABL tyrosine kinase activity is present in multiple myeloma, it is important to note that overexpression of abl and c-myc results in the accelerated development of mouse plasmacytomas. Thus, it may be more than a coincidence that multiple myeloma cells significantly overexpresses MYC and ABL.

Chromosomal translocations involving the MYC oncogene and IGH and IGL genes that result in dysregulated MYC expression are hallmarks of Burkitt's lymphoma and experimentally induced mouse plasmacytomas; however, MYC/IGH-associated translocations are rare in multiple myeloma. Although high MYC expression was a common feature in our panel of multiple myeloma, it was quite variable, ranging from little or no expression to highly elevated expression. It is also of note that the MAZ gene whose product is known to bind to and activate MYC expression was significantly upregulated in the MM4 subgroup. Given the important role of MYC in B cell neoplasia, it is speculated that overexpression of MYC, and possibly ABL, in multiple myeloma may have biological and possibly prognostic significance.

EXT1 and EXT2, which are tumor suppressor genes involved in hereditary multiple exostoses, heterodimerize and are critical in the synthesis and display of cell surface heparan sulfate glycosaminoglycans (GAGs). EXT1 is expressed in both multiple myeloma and normal plasma cells. EXT2L was overexpressed in multiple myeloma, suggesting that a functional glycosyltransferase could be created in multiple myeloma. It is of note that syndecan-1 (CD138/SDC1), a transmembrane heparan sulfate proteoglycan, is abundantly expressed on multiple myeloma cells and, when shed into the serum, is a negative prognostic factor. Thus, abnormal GAG-modified SDC1 may be important in multiple myeloma biology. The link of SDC1 to multiple myeloma biology is further confirmed by the recent association of SDC1 in the signaling cascade induced by the WNT proto-oncogene products. It has been showed that syndecan-1 (SDC1) is required for Wnt-1-induced mammary tumorigenesis. Data disclosed herein indicated a significant downregulation of WNT10B in primary multiple myeloma cases. It is also of note that the WNT5A gene and the FRZB gene, which codes for a decoy WNT receptor, were also marginally upregulated in newly diagnosed multiple myeloma. Given that the WNTs represent a novel class of B cell regulators, deregulation of the expression of these growth factors (WNT5A, WNT10B) and their receptors (e.g., FRZB) and genes products that modulate receptor signaling (e.g., SDC1), may be important in the genesis of multiple myeloma.

The present invention also identifies, through multivariate stepwise discriminant analysis, a minimum subset of genes whose expression is intimately associated with the malignant features of multiple myeloma. By applying linear regression analysis to the top 50 statistically significant differentially expressed genes, 14 genes were defined as predictors that are able to differentiate multiple myeloma from normal plasma cells with a high degree of accuracy. When the model was applied to a validation group consisting of 118 multiple myeloma, 6 normal plasma cells and 7 cases of MGUS, an accuracy of classification of more than 99% was achieved. Importantly, 6 of the 7 MGUS cases were classified as multiple myeloma, indicating that MGUS has gene expression features of malignancy. Thus the altered expression of 14 genes out of over 6,000 genes interrogated are capable of defining multiple myeloma. Similar multivariate discriminant analysis also identified a set of 24 genes that can distinguish between the four multiple myeloma subgroups described above.

In addition to identifying genes that were statistically different between the group of normal plasma cells and multiple myeloma plasma cells, the present invention also identified genes, like FGFR3 and CCND1, that demonstrate highly elevated "spiked" expression in subsets of multiple myelomas. Patients with elevated expression of these genes can have significant distribution differences among the four gene expression cluster subgroups. For example, FGFR3 spikes are found in MM1 and MM2 whereas spikes of IFI27 are more likely to be found in MM3 and MM4. Highly elevated expression of the interferon-induced gene IFI27 may be indicative of a viral infection, either systemic or specifically within the plasma cells from these patients. Correlation analysis has shown that IFI27 spikes are significantly linked (Pearson correlation coefficient values of 0.77 to 0.60) to elevated expression of 14 interferon-induced genes, including MX1, MX2, OAS1, OAS2, IFIT1, IFIT4, PLSCR1, and STAT1. More recent analysis of a large population of multiple myeloma patients (N=280) indicated that nearly 25% of all patients had spikes of the IFI27 gene. It is of interest to determine whether or not the IFI27 spike patients who cluster in the MM4 subgroup are more likely to have a poor clinical course and to identify the suspected viral infection causing the upregulation of this class of genes. Thus, spiked gene expression may also be used in the development of clinically relevant prognostic groups.

Finally, the 100% coincidence of spiked FGFR3 or CCND1 gene expression with the presence of the t(4;14)(p14;q32) or t(11;14)(q13;q32) translocations, as well as the strong correlations between protein expression and gene expression represent important validations of the accuracy of gene expression profiling and suggests that gene expression profiling may eventually supplant the labor intensive and expensive clinical laboratory procedures, such as cell surface marker immunophenotyping and molecular and cellular cytogenetics.

Genes identified by the present invention that shows significantly up-regulated or down-regulated expression in multiple myeloma are potential therapeutic targets for multiple myeloma. Over-expressed genes may be targets for small molecules or inhibitors that decrease their expression. Methods and materials that can be used to inhibit gene expression, e.g. small drug molecules, anti-sense oligo, or antibody would be readily apparent to a person having ordinary skill in this art. On the other hand, under-expressed genes can be replaced by gene therapy or induced by drugs.

Comparison of Multiple Myeloma with Normal Plasma Cell Development

Data disclosed herein indicated that multiple myeloma can be placed into a developmental schema parallel to that of normal plasma cell differentiation. Global gene expression profiling reveals distinct changes in transcription associated with human plasma cell differentiation. Hierarchical clustering analyses with 4866 genes segregated tonsil B cells, tonsil plasma cells, and bone marrow plasma cells. Combining $\chi^2$ and Wilcoxon rank sum tests, 359 previously defined and novel genes significantly (P<0.0005) discriminated tonsil B cells from tonsil plasma cells, and 500 genes significantly discriminated tonsil plasma cells from bone marrow plasma cells. Genes that were significantly differentially expressed in the tonsil B cell to tonsil plasma cell transition were referred as "early differentiation genes" (EDGs) and those differentially expressed in the tonsil plasma cell to bone marrow plasma cell transition were referred as "late differentiation genes" (LDGs). One-way ANOVA was then applied to EDGs and LDGs to identify statistically significant expression differences between multiple myeloma (MM) and tonsil B cells (EDG-MM), tonsil plasma cells (LDG-MM1), or bone marrow plasma cells (LDG-MM2).

Hierarchical cluster analysis revealed that 13/18 (P=0.00005) MM4 cases (a putative poor-prognosis subtype) clustered tightly with tonsil B cells. The other groups (MM1, 2 and 3) failed to show such associations. In contrast, there was tight clustering between tonsil plasma cells and 14/15 (P=0.00001) MM3, and significant similarities between bone marrow plasma cells and 14/20 (P=0.00009) MM2 cases were found. MM1 showed no significant linkage with the normal cell types studied. In addition, XBP1, a transcription factor essential for plasma cell differentiation, exhibited a significant, progressive reduction in expression from MM1 to MM4, consistent with developmental-stage relationships. Therefore, global gene expression patterns linked to late-stage B cell differentiation confirmed and extended a global gene expression-defined classification system of multiple myeloma, suggesting that multiple myeloma represents a constellation of distinct subtypes of disease with unique origins.

In summary, the present invention is drawn to a method of gene expression profiling for multiple myeloma. Nucleic acid samples of isolated plasma cells derived from individuals with or without multiple myeloma were applied to a DNA microarray, and hierarchical clustering analysis performed on data obtained from the microarray will classify the individuals into distinct subgroups such as the MM1, MM2, MM3 and MM4 subgroups disclosed herein. The profiling will also identify genes with elevated expression in subsets of multiple myeloma patients or genes with significantly different levels of expression in multiple myeloma patients as compared to normal individuals. These genes are potential therapeutic targets for multiple myeloma. Representative examples of these genes are listed in Tables 4, 5 and 8.

In another embodiment of the present invention, there is provided a method of identifying a group of genes that can distinguish between normal plasma cells and plasma cells of multiple myeloma. Nucleic acid samples of isolated plasma cells derived from individuals with or without multiple myeloma were applied to a DNA microarray, and hierarchical clustering analysis was performed on data obtained from the microarray. Genes with statistically significant differential expression patterns were identified, and linear regression analysis was used to identify a group of genes that is capable of accurate discrimination between normal plasma cells and plasma cells of multiple myeloma. Representative examples of these genes are listed in Table 6. This analysis can also identify a group of genes that is capable of accurate discrimination between subgroups of multiple myeloma. Representative examples of these genes are listed in Table 7.

Expression levels of such a group of 14 genes as listed in Table 6 or a group of 24 genes as listed in Table 7 could be used for diagnosis of multiple myeloma. Significant differential expression of these genes would indicate that such individual has multiple myeloma or a subgroup of multiple myeloma. Gene expression levels can be examined at nucleic acid level or protein level according to methods well known to one of skill in the art.

In another embodiment of the present invention, there are provided methods of treatment for multiple myeloma. Such methods involve inhibiting expression of one of the genes listed in Table 5 or Table 8, or increasing expression of one of the genes listed in Table 4. Methods of inhibiting or increasing gene expression such as those using anti-sense oligonucleotide or antibody are well known to one of skill in the art. Inhibiting gene expression can be achieved through RNA interference using so called siRNA. Gene expression enhancement might be through gene therapy.

The present invention is also drawn to a method of developmental stage-based classification for multiple myeloma. Nucleic acid samples of isolated B cells and plasma cells derived from individuals with or without multiple myeloma were applied to a DNA microarray, and hierarchical clustering analysis performed on data obtained from the microarray will classify the multiple myeloma cells according to the developmental stages of normal B cells and plasma cells. In general, normal B cells and plasma cells are isolated from tonsil, bone marrow, mucoal tissue, lymph node or peripheral blood.

The present invention also provides a method of controlling bone loss in an individual by inhibiting the expression of the DKK1 gene (accession number NM012242). In general, DKK1 expression can be inhibited by anti-sense oligonucleotides or anti-DKK1 antibodies. In another embodiment, bone loss can be controlled by a pharmacological inhibitor of DKK1 protein. Preferably, the individual having bone loss may have multiple myeloma, osteoporosis, post-menopausal osteoporosis or malignancy-related bone loss that is caused by breast cancer metastasis or prostate cancer metastasis.

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

EXAMPLE 1

Cell Isolation and Analysis

Samples for the following studies included plasma cells from 74 newly diagnosed cases of multiple myeloma, 5 subjects with monoclonal gammopathy of undetermined significance, 7 samples of tonsil B lymphocytes (tonsil BCs), 11 samples of tonsil plasma cells (tonsil PCs), and 31 bone marrow PCs derived from normal healthy donor.

Multiple myeloma cell lines (U266, ARP1, RPMI-8226, UUN, ANBL-6, CAG, and H929 (courtesy of P. L. Bergsagel) and an Epstein-Barr virus (EBV)-transformed B-lymphoblastoid cell line (ARH-77) were grown as recommended (ATCC, Chantilly, Va.).

Tonsils were obtained from patients undergoing tonsillectomy for chronic tonsillitis. Tonsil tissues were minced, softly teased and filtered. The mononuclear cell fraction from tonsil preparations and bone marrow aspirates were separated by a standard Ficoll-Hypaque gradient (Pharmacia Biotech, Piscataway, N.J.). The cells in the light density fraction (S.G.≦1.077) were resuspended in cell culture media and 10% fetal bovine serum, RBC lysed, and several PBS wash steps were performed. Plasma cell isolation was performed with anti-CD138 immunomagnetic bead selection as previously described (Zhan et al., 2002a). B lymphocyte isolation was performed using directly conjugated monoclonal mouse anti-human CD19 antibodies and the AutoMacs automated cell sorter (Miltenyi-Biotec, Auburn, Calif.).

For cytology, approximately 40,000 purified tonsil BC and PC mononuclear cells were cytocentrifuged at 1000×g for 5 min at room temperature. For morphological studies, the cells were immediately processed by fixing and staining with DiffQuick fixative and stain (Dade Diagnostics, Aguada, PR).

For immunofluorescence, slides were treated essentially as described (Shaughnessy et al., 2000). Briefly, slides were air-dried overnight, then fixed in 100% ethanol for 5 min at room temperature and baked in a dry 37° C. incubator for 6 hr. The slides were then stained with 100 µl of a 1:20 dilution of goat anti-human-kappa immunoglobulin light chain conjugated with 7-amino-4-methylcourmarin-3-acitic acid (AMCA) (Vector Laboratories, Burlingame, Calif.) for 30 min in a humidified chamber. After incubation, the slides were washed two times in 1×PBS+0.1% NP-40 (PBD). To enhance the AMCA signal, the slides were incubated with 100 µl of a 1:40 dilution of AMCA-labeled rabbit-anti-goat IgG antibody and incubated for 30 min at room temperature in a humidified chamber. Slides were washed 2 times in 1×PBD. The slides were then stained with 100 µl of a 1:100 dilution of goat anti-human-lambda immunoglobulin light chain conjugated with FITC (Vector Laboratories, Burlingame, Calif.) for 30 min in a humidified chamber; the slides were washed two times in 1×PBD. Then the slides were stained with propidium iodide at 0.1 µg/ml in 1×PBS for 5 min, washed in 1×PBD, and 10 µl anti-fade (Molecular Probes, Eugene, Oreg.) was added and coverslips were placed. Cytoplasmic immunoglobulin light chain-positive PCs were visualized using an Olympus BX60 epi-fluorescence microscope equipped with appropriate filters. The images were captured using a Quips XL genetic workstation (Vysis, Downers Grove, Ill.)

Both unpurified mononuclear cells and purified fractions from tonsil BCs, tonsil PCs, and bone marrow PCs were subjected to flow cytometric analysis of CD marker expression using a panel of antibodies directly conjugated to FITC or PE. Markers used in the analysis included FITC-labeled CD20, PE-labeled CD38, FITC-labeled or ECD-labeled CD45, PE- or PC5-labled CD138 (Beckman Coulter, Miami, Fla.). For detection of CD138 on PCs after CD138 selection, we employed an indirect detection strategy using a FITC-labeled rabbit anti-mouse IgG antibody (Beckman Coulter) to detect the mouse monoclonal anti-CD138 antibody BB4 used in the immunomagnetic selection technique. Cells were taken after Ficoll Hypaque gradient or after cell purification, washed in PBS, and stained at 4° C. with CD antibodies or isotype-matched control G1 antibodies (Beckman Coulter). After staining, cells were resuspended in 1×PBS and analyzed using a Epics XL-MCL flow cytometry system (Beckman Coulter).

EXAMPLE 2

Preparation of Labeled cRNA and Hybridization to High-Density Microarray

Total RNA was isolated with RNeasy Mini Kit (Qiagen, Valencia, Calif.). Double-stranded cDNA and biotinylated cRNA were synthesized from total RNA and hybridized to GENECHIP® HUGENEFL® microarrays (Affymetrix, Santa Clara, Calif.), which were washed and scanned according to procedures developed by the manufacturer. The arrays were scanned using Hewlett Packard confocal laser scanner and visualized using Affymetrix 3.3 software (Affymetrix). Arrays were scaled to an average intensity of 1,500 and analyzed independently.

EXAMPLE 3

Geneehip GENCHIP® (DNA microarray) Data Analysis

To efficiently manage and mine high-density oligonucleotide DNA microarray data, a new data-handling tool was developed. GENCHIP® (DNA microarray) derived expression data was stored on an MS SQL Server. This database was linked, via an MS Access interface called Clinical Gene-Organizer to multiple clinical parameter databases for multiple myeloma patients. This Data Mart concept allows gene expression profiles to be directly correlated with clinical parameters and clinical outcomes using standard statistical software. All data used in the present analysis were derived from Affymetrix 3.3 software. GENCHIP® (DNA microarray) 3.3 output files are given (1) as an average difference (AD) that represents the difference between the intensities of the sequence-specific perfect match probe set and the mismatch probe set, or (2) as an absolute call (AC) of present or absent as determined by the GENCHIP® (DNA microarray) 3.3 algorithm. Average difference calls were transformed by the natural log after substituting any sample with an average difference of <60 with the value 60 (2.5 times the average Raw Q). Statistical analysis of the data was performed with software packages SPSS 10.0 (SPSS, Chicago, Ill.), S-Plus 2000 (Insightful Corp., Seattle, Wash.), and Gene Cluster/Treeview (Eisen at al., 1998).

To differentiate four distinct subgroups of multiple myeloma (MM 1, MM2, MM3 and MM4), hierarchical clustering of average linkage clustering with the centered correlation metric was employed. The clustering was done on the average difference data of 5,483 genes. Either Chi square ($c^2$) or Fisher's exact test was used to find significant differences between cluster groups with the AC data. To compare the expression levels, the non-parametric Wilcoxon rank sum (WRS) test was used. This test uses a null hypothesis that is based on ranks rather than on normally distributed data. Before the above tests were performed genes that were absent (AC) across all samples were removed; 5,483 genes were used in the analyses. Genes that were significant (P <0.0001) for both the $c^2$ test and the WRS test were considered to be significantly differentially expressed.

Clinical parameters were tested across multiple myeloma cluster groups. ANOVA test was used to test the continuous variables, and $\chi^2$ test of independence or Fisher's exact test was applied to test discrete variables. The natural log of the average difference data was used to find genes with a "spiked profile" of expression in multiple myeloma. Genes were identified that had low to undetectable expression in the majority of patients and normal samples (no more than 4 present absolute calls [P-AC]). A total of 2,030 genes fit the criteria of this analysis. The median expression value of each of the genes across all patient samples was determined. For the $i^{th}$ gene, this value was called medgene (i). The $i^{th}$ gene was a "spiked" gene if it had at least 4 patient expression values >2.5+medgene (i). The constant 2.5 was based on the log of the average difference data. These genes that were "spiked" were further divided into subsets according to whether or not the largest spike had an average difference expression value greater than 10,000.

To determine transcriptional changes associated with human plasma cell differentiation, a total of 4866 genes were scanned across 7 cases each of tonsil B cells, tonsil plasma cells, and bone marrow plasma cells. The 4866 genes were derived from 6800 by filtering out all control genes, and genes not fulfilling the test of Max−Min<1.5 (1.5 being the natural log of the average difference). The $\chi^2$ test was used to eliminate genes with absent absolute call (AAC). For example, in the tonsil plasma cell to bone marrow plasma cell comparison, genes with $\chi^2$ values greater than 3.84 (P<0.05) or having "present" AC (PAC) in more than half of the samples in each group were retained. In the tonsil B cell to tonsil plasma cell and tonsil plasma cell to bone marrow plasma cell comparisons, 2662 and 2549 genes were retained as discriminating between the two groups, respectively. To compare gene expression levels, the non-parametric Wilcoxon Rank Sum (WRS) test was used to compare two groups using natural log transformed AD. The cutoff P value depended on the sample size, the heterogeneity of the two comparative populations (tonsil B cells, tonsil plasma cells, and bone marrow plasma cells showed a higher degree of stability in AD), and the degree of significance. In this analysis, 496 and 646 genes were found to be significantly (P<0.0005) differentially expressed in the tonsil B cell versus tonsil plasma cell and tonsil plasma cell versus bone marrow plasma cell comparisons, respectively. To define the direction of significance (expression changes being up or down in one group compared with the other), the non-parametric Spearman correlation test of the AD was employed.

Genes that were significantly differentially expressed in the tonsil B cell to tonsil plasma cell transition were referred as "early differentiation genes" (EDGs) and those differentially expressed in the tonsil plasma cell to bone marrow plasma cell transition were referred as "late differentiation genes" (LDGs). Previously defined and novel genes were identified that significantly discriminated tonsil B cells from tonsil plasma cells (359 genes) and tonsil plasma cells from bone marrow plasma cells (500 genes).

To classify multiple myeloma with respect to EDG and LDG, 74 newly diagnosed cases of multiple myeloma and 7 tonsil B cell, 7 tonsil plasma cell, and 7 bone marrow plasma cell samples were tested for variance across the 359 EDGs and 500 LDGs. The top 50 EDGs that showed the most significant variance across all samples were defined as early differentiation genes for myeloma (EDG-MM). Likewise, the top 50 LDGs showing the most significant variance across all samples were identified as late differentiation genes for myeloma-1 (LDG-MM1). Subtracting the LDG-MM1 from the 500 LDG and then applying one-way ANOVA test for variance to the remaining genes identified the top 50 genes showing similarities between bone marrow plasma cells and multiple myeloma. These genes were defined as LDG-MM2.

Hierarchical clustering was applied to all samples using 30 of the 50 EDG-MM. A total of 20 genes were filtered out with Max−Min<2.5. This filtering was performed on this group because many of the top 50 EDG-MM showed no variability across multiple myeloma and thus could not be used to distinguish multiple myeloma subgroups. A similar clustering strategy was employed to cluster the samples using the 50 LDG-MM1 and 50 LDG-MM2; however, in these cases all 50 significant genes were used in the cluster analysis.

EXAMPLE 4

RT-PCR and Immunohistochemistry

RT-PCR for the FGFR3 MMSET was performed on the same cDNAs used in the microarray analysis. Briefly, cDNA was mixed with the IGJH2 (5'-CAATGGTCACCGTCTCT-TCA-3', SEQ ID No. 1) primer and the MMSET primer (5'-CCTCAATTTCCTGAAATTGGTT-3', SEQ ID No. 2). PCR reactions consisted of 30 cycles with a 58° C. annealing temperature and 1-minute extension time at 72° C. using a Perkin-Elmer GeneAmp 2400 thermocycler (Wellesley, Mass.). PCR products were visualized by ethidium bromide staining after agarose gel electrophoresis.

Immunohistochemical staining was performed on a Ventana ES (Ventana Medical Systems, Tucson, Ariz.) using Zenker-fixed paraffin-embedded bone marrow sections, an avidin-biotin peroxidase complex technique (Ventana Medical Systems), and the antibody L26 (CD20, Ventana Medical Systems). Heat-induced epitope retrieval was performed by microwaving the sections for 28 minutes in a 1.0-mmol/L concentration of citrate buffer at pH 6.0.

EXAMPLE 5

Interphase FISH

For interphase detection of the t(11;14)(q13;q32) translocation fusion signal, a LSI IGH/CCND1 dual-color, dual-fusion translocation probe was used (Vysis, Inc, Downers Grove, Ill.). The TRI-FISH procedure used to analyze the samples has been previously described. Briefly, at least 100 clonotypic plasma cells identified by cIg staining were counted for the presence or absence of the translocation fusion signal in all samples except one, which yielded only 35 plasma cells. An multiple myeloma sample was defined as having the translocation when >25% of the cells contained the fusion.

EXAMPLE 6

Figure 1D:
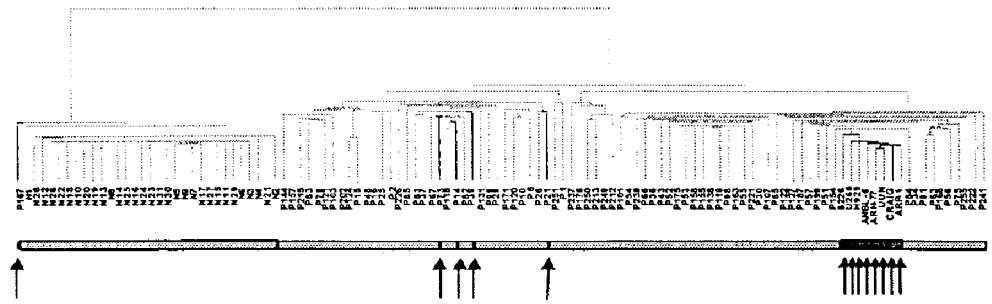
FIG. 1D shows a dendrogram of hierarchical cluster. 74 cases of newly diagnosed untreated multiple myeloma, 5 monoclonal gammopathy of undetermined significance, 8 multiple myeloma cell lines, and 31 normal bone marrow plasma cell samples clustered based on the correlation of 5,483 genes (probe sets). Different-colored branches represent normal plasma cell (green), monoclonal gammopathy of undetermined significance (blue arrow), multiple myeloma (tan) and multiple myeloma cell lines (brown arrow).

Hierarchical Clustering of Plasma Cell Gene Expression Demonstrates Class Distinction As a result of 656,000 measurements of gene expression in 118 plasma cell samples, altered gene expression in the multiple myeloma samples was identified. Two-dimensional hierarchical clustering differentiated cell types by gene expression when performed on 5,483 genes that were expressed in at least one of the 118 samples (FIG. 1A). The sample dendrogram derived two major branches (FIGS. 1A and 1D). One branch contained all 31 normal samples and a single monoclonal gammopathy of undetermined significance case whereas the second branch contained all 74 multiple myeloma and 4 monoclonal gammopathy of undetermined significance cases and the 8 cell lines. The multiple myeloma-containing branch was further divided into two sub-branches, one containing the 4 monoclonal gammopathy of undetermined significance and the other the 8 multiple myeloma cell lines. The cell lines were all clustered next to one another, thus showing a high degree of similarity in gene expression among the cell lines. This suggested that multiple myeloma could be differentiated from normal plasma cells and that at least two different classes of multiple myeloma could be identified, one more similar to monoclonal gammopathy of undetermined significance and the other similar to multiple myeloma cell lines.

Hierarchical clustering analysis with all 118 samples together with duplicate samples from 12 patients (plasma cells taken 24 hr or 48 hr after initial sample) were repeated to show reproducibility of the technique and analysis. All samples from the 12 patients studied longitudinally were found to cluster adjacent to one another. This indicated that gene expression in samples from the same patient were more similar to each other than they were to all other samples (data not shown).

In addition to the demonstration of reproducibility of clustering noted above, three microarray analyses were also performed on a single source of RNA from one patient. When included in the cluster analysis, the three samples clustered adjacent to one another. Consistent with the manufacturer's specification, an analysis of the fold changes seen in the samples showed that <2% of all genes had a >2-fold difference. Hence, these data indicated reproducibility for same samples.

The clustergram (FIG. 1A) showed that genes of unrelated sequence but similar function clustered tightly together along the vertical axis. For example, a particular cluster of 22 genes, primarily those encoding immunoglobulin molecules and major histocompatibility genes, had relatively low expression in multiple myeloma plasma cells and high expression in normal plasma cells (FIG. 1B). This was anticipated, given that the plasma cells isolated from multiple myeloma are clonal and hence only express single immunoglobulin light-chain and heavy-chain variable and constant region genes, whereas plasma cells from normal donors are polyclonal and express many different genes of these two classes. Another cluster of 195 genes was highly enriched for numerous oncogenes/growth-related related genes (e.g., MYC, ABL1, PHB, and EXT2), cell cycle-related genes (e.g., CDC37, CDK4, and CKS2), and translation machinery genes (EIF2, EIF3, HTF4A, and TFIIA) (FIG. 1C). These genes were all highly expressed in MM, especially in multiple myeloma cell lines, but had low expression levels in normal plasma cells.

EXAMPLE 7

Figure 1E:
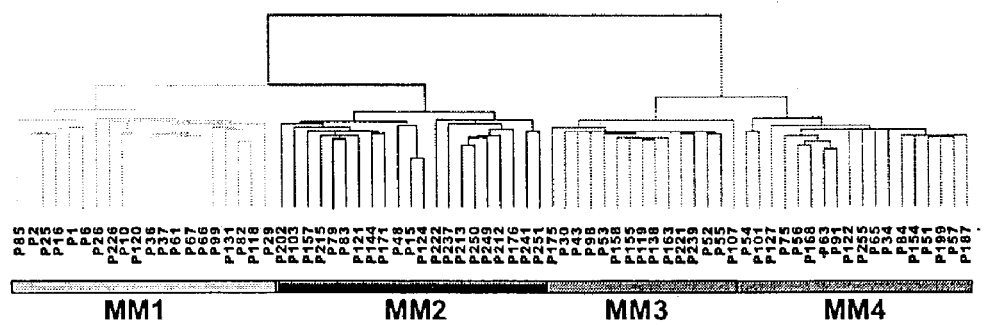
FIG. 1E shows a dendrogram of a hierarchical cluster analysis of 74 cases of newly diagnosed untreated multiple myeloma alone (clustergram note shown). Two major branches contained two distinct cluster groups. The subgroups under the right branch, designated MM1 (light blue) and MM2 (blue) were more related to the monoclonal gammopathy of undetermined significance cases in FIG. 1D. The two subgroups under the left branch, designated MM3 (violet) and MM4 (red) represent samples that were more related to the multiple myeloma cell lines in FIG. 1D.

Hierarchical Clustering of Newly Diagnosed Multiple Myeloma Identifies Four Distinct Subgroups Two-dimensional cluster analysis was performed on the 74 multiple myeloma cases alone. The sample dendrogram identified two major branches with two distinct subgroups within each branch (FIG. 1E). The four subgroups were designated MM1, MM2, MM3, and MM4 containing 20, 21, 15, and 18 patients respectively. The MM1 subgroup represented the patients whose plasma cells were most closely related to the monoclonal gammopathy of undetermined significance plasma cells and MM4 were most like the multiple myeloma cell lines (see FIG. 1D). These data suggested that the four gene expression subgroups were authentic and might represent four distinct clinical entities.

Differences in gene expression across the four subgroups were then examined using the $\chi^2$ and WRS tests (Table 1). As expected the largest difference was between MM1 and MM4 (205 genes) and the smallest difference was between MM1 and MM2 (24 genes). Next, the top 30 genes turned on or upregulated in MM4 as compared with MM1 were examined (Table 2). The data demonstrated that 13 of 30 most significant genes (10 of the top 15 genes) were involved in DNA replication/repair or cell cycle control. Thymidylate synthase (TYMS), which was present in all 18 samples comprising the MM4 subgroup, was only present in 3 of the 20 MM1 samples and represented the most significant gene in the $\chi^2$ test. The DNA mismatch repair gene, mutS (E. coli) homolog 2 (MSH2) with a WRS P value of $2.8 \times 10^{-6}$ was the most significant gene in the WRS test. Other notable genes in the list included the CAAX farnesyltransferase (FNTA), the transcription factors enhancer of zeste homolog 2 (EZH2) and MYC-associated zinc finger protein (MAZ), eukaryotic translation initiation factors (EIF2S1 and EIF2B1), as well as the mitochondrial translation initiation factor 2 (MTIF2), the chaperone (CCT4), the UDP-glucose pyrophosphorylase 2 (IUGP2), and the 26S proteasome-associated pad1 homolog (POH1).

To assess the validity of the clusters with respect to clinical features, correlations of various clinical parameters across the 4 subgroups were analyzed (Table 3). Of 17 clinical variables tested, the presence of an abnormal karyotype (P=0.0003) and serum β2M levels (P=0.0005) were significantly different among the four subgroups and increased creatinine (P=0.06) and cytogenetic deletion of chromosome 13 (P=0.09) were marginally significant. The trend was to have higher β2M and creatinine as well as an abnormal karyotype and chromosome 13 deletion in the MM4 subgroup as compared with the other 3 subgroups.

TABLE 1

Differences In Gene Expression Among Multiple Myeloma Subgroups

| Comparison | Range of WRS* P Values | Number of Genes |
| --- | --- | --- |
| MM1 vs MM4 | .00097 to $9.58 \times 10^{-7}$ | 205 |
| MM2 vs MM4 | .00095 to $1.0410^{-6}$ | 162 |
| MM3 vs MM4 | .00098 to $3.7510^{-6}$ | 119 |
| MM1 vs MM3 | .00091 to $6.2710^{-6}$ | 68 |
| MM2 vs MM3 | .00097 to $1.9810^{-5}$ | 44 |
| MM1 vs MM2 | .00083 to $2.9310^{-5}$ | 24 |

*Wilcoxon rank sum test. Comparisons are ordered based on the number of significant genes. Comparisons have a WRS P value < 0.001.

TABLE 2

The 30 Most Differentially Expressed Genes In A Comparison Of MM1 And MM4 Subgroups

| Accession* | Function | Gene Symbol | MM1 (N = 20) P | MM4 (N = 18) P | Chi Square | WRS‡ P Value |
| --- | --- | --- | --- | --- | --- | --- |
| D00596 | DNA replication | TYMS | 3 | 18 | 24.35 | $1.26 \times 10^{-4}$ |
| U35835 | DNA repair | PRKDC | 2 | 17 | 23.75 | $4.55 \times 10^{-6}$ |

TABLE 2-continued

The 30 Most Differentially Expressed Genes In A Comparison Of MM1 And MM4 Subgroups

| Accession* | Function | Gene Symbol | MM1 (N = 20) P | MM4 (N = 18) P | Chi Square | WRS‡ P Value |
|---|---|---|---|---|---|---|
| U77949 | DNA replication | CDC6 | 1 | 13 | 15.62 | $5.14 \times 10^{-6}$ |
| U91985 | DNA fragmentation | DFFA | 1 | 12 | 13.38 | $6.26 \times 10^{-5}$ |
| U61145 | transcription | EZH2 | 4 | 15 | 12.77 | $1.67 \times 10^{-4}$ |
| U20979 | DNA replication | CHAF1A | 2 | 12 | 10.75 | $1.10 \times 10^{-4}$ |
| U03911 | DNA repair | MSH2 | 0 | 9 | 10.48 | $2.88 \times 10^{-6}$ |
| X74330 | DNA replication | PRIM1 | 0 | 9 | 10.48 | $9.36 \times 10^{-6}$ |
| X12517 | SnRNP | SNR PC | 0 | 9 | 10.48 | $5.26 \times 10^{-6}$ |
| D85131 | transcription | MAZ | 0 | 9 | 10.48 | $1.08 \times 10^{-5}$ |
| L00634 | farnesyltransferase | FNTA | 10 | 18 | 9.77 | $7.28 \times 10^{-5}$ |
| U21090 | DNA replication | POLD2 | 11 | 18 | 8.27 | $8.05 \times 10^{-5}$ |
| X54941 | cell cycle | CKS1 | 10 | 17 | 7.07 | $1.26 \times 10^{-4}$ |
| U62136 | cell cycle | UBE2V2 | 13 | 18 | 5.57 | $4.96 \times 10^{-6}$ |
| D38076 | cell cycle | RANBP1 | 13 | 18 | 5.57 | $7.34 \times 10^{-6}$ |
| X95592 | unknown | C1D† | 13 | 18 | 5.57 | $1.10 \times 10^{-4}$ |
| X66899 | cell cycle | EWSR1 | 14 | 18 | 4.35 | $1.89 \times 10^{-4}$ |
| L34600 | translation initiation | MTIF2 | 14 | 18 | 4.35 | $3.09 \times 10^{-5}$ |
| U27460 | Metabolism | IUGP2 | 15 | 18 | 3.22 | $1.65 \times 10^{-4}$ |
| U15009 | SnRNP | SNRPD3 | 15 | 18 | 3.22 | $1.47 \times 10^{-5}$ |
| J02645 | translation initiation | EIF2S1 | 16 | 18 | 2.18 | $7.29 \times 10^{-5}$ |
| X95648 | translation initiation | EIF2B1 | 16 | 18 | 2.18 | $1.45 \times 10^{-4}$ |
| M34539 | calcium signaling | FKBP1A | 18 | 18 | 0.42 | $1.71 \times 10^{-5}$ |
| J04611 | DNA repair | G22P1 | 18 | 18 | 0.42 | $7.29 \times 10^{-5}$ |
| U67122 | anti-apoptosis | UBL1 | 20 | 18 | 0.00 | $7.29 \times 10^{-5}$ |
| U38846 | chaperon | CCT4 | 20 | 18 | 0.00 | $1.26 \times 10^{-4}$ |
| U80040 | metabolism | ACO2 | 20 | 18 | 0.00 | $8.38 \times 10^{-5}$ |
| U86782 | proteasome | POH† | 20 | 18 | 0.00 | $5.90 \times 10^{-5}$ |
| X57152 | signaling | CSNK2B | 20 | 18 | 0.00 | $7.29 \times 10^{-5}$ |
| D87446 | unknown | KIAA0257† | 20 | 18 | 0.00 | $1.26 \times 10^{-5}$ |

Accession numbers listed are GENBANK ® numbers. †Gene symbol not HUGO approved. ‡Wilcoxon rank sum test.

Accession numbers listed are GENBANK numbers. † Gene symbol not HUGO approved. ‡ Wilcoxon rank sum test.

TABLE 3

Clinical Parameters Linked To Multiple Myeloma Subgroups

| Clinical Parameter | Multiple Myeloma Subgroups | | | | P value |
|---|---|---|---|---|---|
| | 1 | 2 | 3 | 4 | |
| Abnormal cytogenetics | 40.0% | 5.3% | 53.3% | 72.2% | .00028 |
| Average β2-microglobulin (mg/L) | 2.81 | 2.73 | 4.62 | 8.81 | .00047 |

ANOVA, Chi square, and Fisher's exact tests were used to determine significance.

EXAMPLE 8

Altered Expression of 120 Genes in Malignant Plasma Cells

Hierarchical cluster analysis disclosed above showed that multiple myeloma plasma cells could be differentiated from normal plasma cells. Genes distinguishing the multiple myeloma from normal plasma cells were identified as significant by $\chi^2$ analysis and the WRS test (P<0.0001). A statistical analysis showed that 120 genes distinguished multiple myeloma from normal plasma cells. Pearson correlation analyses of the 120 differentially expressed genes were used to identify whether the genes were upregulated or downregulated in MM.

When genes associated with immune function (e.g. IGH, IGL, HLA) that represent the majority of significantly downregulated genes were filtered out, 50 genes showed significant downregulation in multiple myeloma (Table 4). The P values for the WRS test ranged from $9.80 \times 10^{-5}$ to $1.56 \times 10^{-14}$, and the $\chi^2$ test of the absence or presence of the expression of the gene in the groups ranged from 18.83 to 48.45. The gene representing the most significant difference in the $\chi^2$ test was the CXC chemokine SDF1. It is important to note that a comparison of multiple myeloma plasma cells to tonsil-derived plasma cells showed that, like multiple myeloma plasma cells, tonsil plasma cells also do not express SDF1. Two additional CXC chemokines, PF4 and PF4V1, were also absent in multiple myeloma plasma cells. The second most significant gene was the tumor necrosis factor receptor super family member TNFRF7 coding for CD27, a molecule that has been linked to controlling maturation and apoptosis of plasma cells.

The largest group of genes, 20 of 50, were linked to signaling cascades. multiple myeloma plasma cells have reduced or no expression of genes associated with calcium signaling (S100A9 and S100A12) or lipoprotein signaling (LIPA, LCN2, PLA2G7, APOE, APOC1). LCN2, also known as 24p3, codes for secreted lipocalin, which has recently been shown to induce apoptosis in pro B-cells after growth factor deprivation. Another major class absent in multiple myeloma plasma cells was adhesion-associated genes (ITGA2B, IGTB2, GP5, VCAM, and MIC2).

Correlation analysis showed that 70 genes were either turned on or upregulated in multiple myeloma (Table 5). When considering the $\chi^2$ test of whether expression is present or absent, the cyclin-dependent inhibitor, CDKN1A, was the most significantly differentially expressed gene ($\chi^2 = 53.33$, WRS=$3.65 \times 10^{-11}$). When considering a quantitative change using the WRS test, the tyrosine kinase oncogene ABL1 was the most significant ($\chi^2$=43.10, WRS=3.96×10$^{-14}$). Other oncogenes in the list included USF2, USP4, MLLT3 and MYC. The largest class of genes represented those whose products are involved in protein metabolism (12 genes), including amino acid synthesis, translation initiation, protein folding, glycosylation, trafficking, and protein degradation. Other multiple-member classes included transcription (11 genes), signaling (9 genes), DNA synthesis and modification (6 genes), and histone synthesis and modification (5 genes).

Overexpression of signaling genes such as QSCN6, PHB, phosphatases PTPRK and PPP2R4, and the kinase MAPKAPK3 has been linked to growth arrest. The only secreted growth factor in the signaling class was HGF, a factor known to play a role in multiple myeloma biology. The MOX2 gene, whose product is normally expressed as an integral membrane protein on activated T cells and CD19$^+$ B cells and involved in inhibiting macrophage activation, was in the signaling class. The tumor suppressor gene and negative regulator of β-catenin signaling, APC, was another member of the signaling class. Classes containing two members included RNA binding, mitochondrial respiration, cytoskeletal matrix, metabolism, cell cycle, and adhesion. Single member classes included complement casasde (MASP1), drug resistance (MVP), glycosaminoglycan catabolism, heparin sulfate synthesis (EXTL2), and vesicular transport (TSC1). Four genes of unknown function were also identified as significantly upregulated in MM.

TABLE 4

The 50 Most Significantly Downregulated Genes In Multiple Myeloma In Comparison With Normal Bone Marrow Plasma Cells

| Accession* | Function | Gene Symbol | Chi Square | WRS‡ P Value |
|---|---|---|---|---|
| L36033 | cxc chemokine | SDF1 | 48.45 | 3.05 × 10$^{-12}$ |
| M63928 | signaling | TNFRSF7 | 48.45 | 6.35 × 10$^{-11}$ |
| U64998 | ribonuclease | RNASE6 | 46.44 | 2.82 × 10$^{-9}$ |
| M20902 | lipoprotein signaling | APOC1 | 45.62 | 4.63 × 10$^{-10}$ |
| M26602 | immunity | DEFA1 | 40.75 | 1.06 × 10$^{-12}$ |
| M21119 | immunity | LYZ | 40.73 | 6.24 × 10$^{-10}$ |
| M14636 | metabolism | PYGL | 39.84 | 1.15 × 10$^{-10}$ |
| M26311 | calcium signaling | S100A9 | 38.96 | 3.60 × 10$^{-13}$ |
| M54992 | signaling | CD72 | 36.14 | 2.40 × 10$^{-9}$ |
| X16832 | protein degradation | CTSH | 35.26 | 1.81 × 10$^{-12}$ |
| M12529 | lipoprotein signaling | APOE | 34.50 | 3.95 × 10$^{-14}$ |
| M15395 | adhesion | ITGB2 | 34.02 | 1.74 × 10$^{-13}$ |
| Z74616 | extracellular matrix | COL1A2 | 34.02 | 8.06 × 10$^{-11}$ |
| HT2152 | receptor signaling | CD163 | 33.01 | 1.66 × 10$^{-12}$ |
| U97105 | pyrimidine metabolism | DPYSL2 | 32.52 | 2.22 × 10$^{-10}$ |
| U81787 | signaling | WNT10B | 32.50 | 1.77 × 10$^{-5}$ |
| HT3165 | receptor tyrosine kinase | AXL | 31.36 | 5.26 × 10$^{-11}$ |
| M83667 | transcription | CEBPD | 31.19 | 4.69 × 10$^{-10}$ |
| L33930 | receptor signaling | CD24 | 30.33 | 1.56 × 10$^{-14}$ |
| D83657 | calcium signaling | S100A12 | 29.91 | 6.58 × 10$^{-8}$ |
| M11313 | proteinase inhibitor | A2M | 29.91 | 1.07 × 10$^{-10}$ |
| M31158 | signaling | PRKAR2B | 29.91 | 2.20 × 10$^{-9}$ |
| U24577 | lipoprotein signaling | PLA2G7 | 29.78 | 2.08 × 10$^{-10}$ |
| M16279 | adhesion | MIC2 | 28.75 | 8.01 × 10$^{-11}$ |
| HT2811 | cell cycle | CDK8 | 28.32 | 6.53 × 10$^{-9}$ |
| M26167 | cxc chemokine | PF4V1 | 27.35 | 4.68 × 10$^{-11}$ |
| U44111 | metabolism | HNMT | 27.24 | 2.07 × 10$^{-11}$ |
| X59871 | transcription | TCF7 | 26.79 | 7.16 × 10$^{-10}$ |
| X67235 | transcription | HHEX | 25.21 | 2.07 × 10$^{-10}$ |
| U19713 | calcium signaling | AIF1 | 25.21 | 2.57 × 10$^{-10}$ |
| Y08136 | apoptosis | ASM3A† | 24.74 | 3.30 × 10$^{-8}$ |
| M97676 | transcription | MSX1 | 24.58 | 9.80 × 10$^{-5}$ |
| M64590 | house keeping | GLDC | 24.27 | 4.10 × 10$^{-8}$ |
| M20203 | protease | ELA2 | 24.03 | 6.36 × 10$^{-12}$ |

TABLE 4-continued

The 50 Most Significantly Downregulated Genes In Multiple Myeloma In Comparison With Normal Bone Marrow Plasma Cells

| Accession* | Function | Gene Symbol | Chi Square | WRS‡ P Value |
|---|---|---|---|---|
| M30257 | adhesion | VCAM1 | 23.42 | 1.71 × 10$^{-10}$ |
| M93221 | mediates endocytosis | MRC1 | 23.30 | 1.15 × 10$^{-7}$ |
| S75256 | lipoprotein signaling | LCN2 | 23.30 | 4.17 × 10$^{-7}$ |
| U97188 | RNA binding | KOC1† | 22.47 | 5.86 × 10$^{-9}$ |
| Z23091 | adhesion | GP5 | 22.47 | 7.58 × 10$^{-7}$ |
| M34344 | adhesion | ITGA2B | 21.99 | 8.00 × 10$^{-8}$ |
| M25897 | cxc chemokine | PF4 | 21.89 | 1.12 × 10$^{-8}$ |
| M31994 | house keeping | ALDH1A1 | 21.36 | 4.86 × 10$^{-9}$ |
| Z31690 | lipoprotein signaling | LIPA | 20.67 | 1.50 × 10$^{-9}$ |
| S80267 | signaling | SYK | 20.42 | 5.90 × 10$^{-5}$ |
| U00921 | signaling | LY117 | 18.83 | 1.57 × 10$^{-8}$ |

Accession numbers listed are GENBANK ® numbers, except those beginning with "HT", which are provided by the Institute for Genomic Research (TIGR). †Gene symbol not HUGO approved. ‡Wilcoxon rank sum test.

Accession numbers listed are GENBANK® numbers, except those beginning with "HT", which are provided by the Institute for Genomic Research (TIGR). † Gene symbol not HUGO approved. ‡ Wilcoxon rank sum test.

TABLE 5

The 70 Most Significantly Upregulated Genes in Multiple Myeloma in Comparison with Normal Bone Marrow Plasma Cells

| Accession* | Function | Gene Symbol† | Chi Square | WRS‡ P Value |
|---|---|---|---|---|
| U09579 | cell cycle | CDKN1A | 53.33 | 3.65 × 10$^{-11}$ |
| U78525 | amino acid synthesis | EIF3S9 | 49.99 | 2.25 × 10$^{-2}$ |
| HT5158 | DNA synthesis | GMPS | 47.11 | 4.30 × 10$^{-12}$ |
| X57129 | histone | H1F2 | 46.59 | 5.78 × 10$^{-13}$ |
| M55210 | adhesion | LAMC1 | 45.63 | 1.34 × 10$^{-9}$ |
| L77886 | signaling, phosphatase | PTPRK | 45.62 | 5.42 × 10$^{-10}$ |
| U73167 | glycosaminoglycan catabolism | HYAL3 | 44.78 | 1.07 × 10$^{-10}$ |
| X16416 | oncogene, kinase | ABL1 | 43.10 | 3.96 × 10$^{-14}$ |
| U57316 | transcription | GCN5L2 | 43.04 | 1.36 × 10$^{-12}$ |
| Y09022 | protein glycosylation | NOT56L† | 42.05 | 5.53 × 10$^{-10}$ |
| M25077 | RNA binding | SSA2 | 41.26 | 1.69 × 10$^{-7}$ |
| AC002115 | mitochondrial respiration | COX6B | 41.16 | 2.16 × 10$^{-8}$ |
| Y07707 | transcription | NRF† | 37.59 | 4.79 × 10$^{-10}$ |
| L22005 | protein ubiquination | CDC34 | 34.50 | 2.89 × 10$^{-6}$ |
| X66899 | transcription | EWSR1 | 34.39 | 4.23 × 10$^{-8}$ |
| D50912 | RNA binding | RBM10 | 33.93 | 2.61 × 10$^{-6}$ |
| HT4824 | amino acid synthesis | CBS | 33.77 | 1.49 × 10$^{-6}$ |
| U10324 | transcription | ILF3 | 33.33 | 3.66 × 10$^{-11}$ |
| AD000684 | oncogene, transcription | USF2 | 32.18 | 7.41 × 10$^{-11}$ |
| U68723 | cell cycle | CHES1 | 31.68 | 1.03 × 10$^{-6}$ |
| X16323 | signaling, growth factor | HGF | 30.67 | 4.8210$^{-9}$ |
| U24183 | metabolism | PFKM | 30.47 | 8.92 × 10$^{-10}$ |
| D13645 | unknown | KIAA0020† | 30.47 | 7.40 × 10$^{-6}$ |
| S85655 | signaling, growth arrest | PHB | 29.37 | 1.32 × 10$^{-8}$ |
| X73478 | signaling, phosphatase | PPP2R4 | 28.32 | 6.92 × 10$^{-9}$ |
| L77701 | mitochondrial respiration | COX17 | 27.81 | 1.33 × 10$^{-6}$ |
| U20657 | oncogene, proteasome | USP4 | 27.71 | 2.31 × 10$^{-6}$ |
| M59916 | signaling, DAG signaling | SMPD1 | 27.49 | 3.52 × 10$^{-8}$ |

TABLE 5-continued

The 70 Most Significantly Upregulated Genes in Multiple Myeloma in Comparison with Normal Bone Marrow Plasma Cells

| Accession* | Function | Gene Symbol† | Chi Square | WRS‡ P Value |
|---|---|---|---|---|
| D16688 | oncogene, DNA binding | MLLT3 | 27.24 | $6.97 \times 10^{-13}$ |
| X90392 | DNA endonuclease | DNASE1L1 | 26.98 | $4.72 \times 10^{-7}$ |
| U07424 | amino acid synthesis | FARSL | 26.93 | $1.66 \times 10^{-6}$ |
| X54199 | DNA synthesis | GART | 26.57 | $9.61 \times 10^{-11}$ |
| L06175 | unknown | P5-1† | 26.57 | $5.16 \times 10^{-7}$ |
| M55267 | unknown | EVI2A | 25.92 | $3.79 \times 10^{-6}$ |
| M87507 | protein degradation | CASP1 | 25.78 | $5.46 \times 10^{-7}$ |
| M90356 | transcription | BTF3L2 | 25.78 | $9.68 \times 10^{-8}$ |
| U35637 | cytoskeletal matrix | NEB | 25.40 | $9.15 \times 10^{-6}$ |
| L06845 | amino acid synthesis | CARS | 25.34 | $5.39 \times 10^{-8}$ |
| U81001 | DNA, nuclear matrix attachment | SNURF | 24.58 | $4.54 \times 10^{-5}$ |
| U76189 | heparan sulfate synthesis | EXTL2 | 24.58 | $7.28 \times 10^{-6}$ |
| U53225 | protein trafficking | SNX1 | 24.48 | $5.53 \times 10^{-7}$ |
| X04366 | protein degradation | CAPN1 | 24.35 | $1.26 \times 10^{-9}$ |
| U77456 | protein folding | NAP1L4 | 24.27 | $4.23 \times 10^{-10}$ |
| L42379 | signaling, growth arrest | QSCN6 | 24.27 | $1.28 \times 10^{-10}$ |
| U09578 | signaling, kinase | MAPKAPK3 | 24.27 | $2.35 \times 10^{-9}$ |
| Z80780 | histone | H2BFH | 24.27 | $3.44 \times 10^{-12}$ |
| HT4899 | oncogene, transcription | MYC | 24.27 | $1.77 \times 10^{-5}$ |
| M74088 | signaling, b-catenin regulator | APC | 23.94 | $1.50 \times 10^{-5}$ |
| X57985 | histone | H2BFQ | 23.90 | $3.25 \times 10^{-12}$ |
| X79882 | drug resistance | MVP | 23.47 | $1.77 \times 10^{-11}$ |
| X77383 | protein degradation | CTSO | 23.18 | $4.68 \times 10^{-7}$ |
| M91592 | transcription | ZNF76 | 23.16 | $1.12 \times 10^{-8}$ |
| X63692 | DNA methyltransferase | DNMT1 | 23.12 | $5.15 \times 10^{-11}$ |
| M60752 | histone | H2AFO | 21.60 | $1.46 \times 10^{-8}$ |
| M96684 | transcription | PURA | 21.25 | $4.54 \times 10^{-5}$ |
| U16660 | metabolism | ECH1 | 21.18 | $5.52 \times 10^{-5}$ |
| M86737 | DNA repair | SSRP1 | 20.60 | $2.62 \times 10^{-5}$ |
| U35113 | histone deacetylase | MTA1 | 20.60 | $6.67 \times 10^{-10}$ |
| X81788 | unknown | ICT1 | 20.42 | $2.97 \times 10^{-7}$ |
| HT2217 | signaling | MUC2A | 20.33 | $2.61 \times 10^{-7}$ |
| M62324 | unknown | MRF-1† | 20.31 | $3.98 \times 10^{-9}$ |
| U09367 | transcription | ZNF136 | 20.30 | $7.72 \times 10^{-9}$ |
| X89985 | cytoskeletal matrix | BCL7B | 19.81 | $5.50 \times 10^{-9}$ |
| L19871 | transcription repression | ATF3 | 19.43 | $1.13 \times 10^{-6}$ |
| X69398 | adhesion | CD47 | 19.16 | $6.44 \times 10^{-7}$ |
| X05323 | signaling macrophage inhibitor | MOX2 | 19.16 | $8.58 \times 10^{-6}$ |
| X04741 | protein ubiquination | UCHL1 | 19.14 | $9.76 \times 10^{-5}$ |
| D87683 | vesicular transport | TSC1 | 19.12 | $6.81 \times 10^{-6}$ |
| D17525 | complement cascade | MASP1 | 18.81 | $4.05 \times 10^{-7}$ |

Accession numbers listed are GENBANK ® (GenBank) numbers, except those beginning with "HT", which are provided by the Institute for Genomic Research (TIGR). †Gene symbol not HUGO approved. ‡Wilcoxon rank sum test.

Accession numbers listed are GENBANK® (GenBank) numbers, except those beginning with "HT", which are provided by the Institute for Genomic Research (TIGR). † Gene symbol not HUGO approved. ‡ Wilcoxon rank sum test.

EXAMPLE 9

Altered Exoression of 14 Genes Differentiates Malignant from Normal Plasma Cells The present invention also sought to determine whether expression patterns of a minimum number of genes could be used to clearly differentiate normal, pre-neoplastic and malignant plasma cells. A multivariate step-wise discriminant analysis (MSDA) was applied to the top 50 significantly differentially expressed genes across the normal plasma cells (N=26) and multiple myeloma plasma cells (N=162) and a linear discriminant function between the normal plasma cell group and multiple myeloma group was observed. Both forward and backward variable selections were performed. The choice to enter or remove variables was based on a Wilks' λ analysis, defined as follows: λ(x)=det W(x)/det T(x) where W(x) and T(x) are the within-group and total scatter matrices respectively. Wilks' λ can assume values ranging from 0 to 1. The significance of change in λ was tested using the F statistic. At the end of multivariate step-wise discriminant analysis, only 14 genes were selected to compute the canonical discriminant functions (Table 6). The multivariate step-wise discriminant analysis selected the following equation: Discriminant score=HT5158 (SEQ I.D. 14)×3.683−L33930 (SEQ I.D. 1)×3.134+L42379 (SEQ I.D. 2)×1.284+L77886 (SEQ I.D. 3)×1.792+M14636 (SEQ I.D. 4)×5.971−M26167 (SEQ I.D. 5)×6.834+U10324 (SEQ I.D. 6)×2.861−U24577 (SEQ I.D. 7)×10.909+U35113 (SEQ I.D. 8)×2.309+X16416 (SEQ I.D. 9)×6.671−X64072 (SEQ I.D. 10)×5.143+X79882 (SEQ I.D. 11)×5.53+Z22970 (SEQ I.D. 12)×4.147+Z80780 (SEQ I.D. 13)×2.64−87.795. The cutoff value was −3.3525. Values less than −3.3525 indicated the sample belonged to the normal group and values greater than −3.3525 indicated the sample belonged to the multiple myeloma group.

The 14 gene model was then applied to a training group consisting of 162 multiple myeloma and 26 normal plasma cell (data not shown). A cross-validation analysis was performed where samples were removed one at a time from the sample set, and training statistics and expression means for each class of the modified sample set were re-calculated. A predictive value using genes with a P value <0.05 in the modified sample set was generated. A 100% accurate prediction of the sample types in the training group was obtained.

Figure 5:
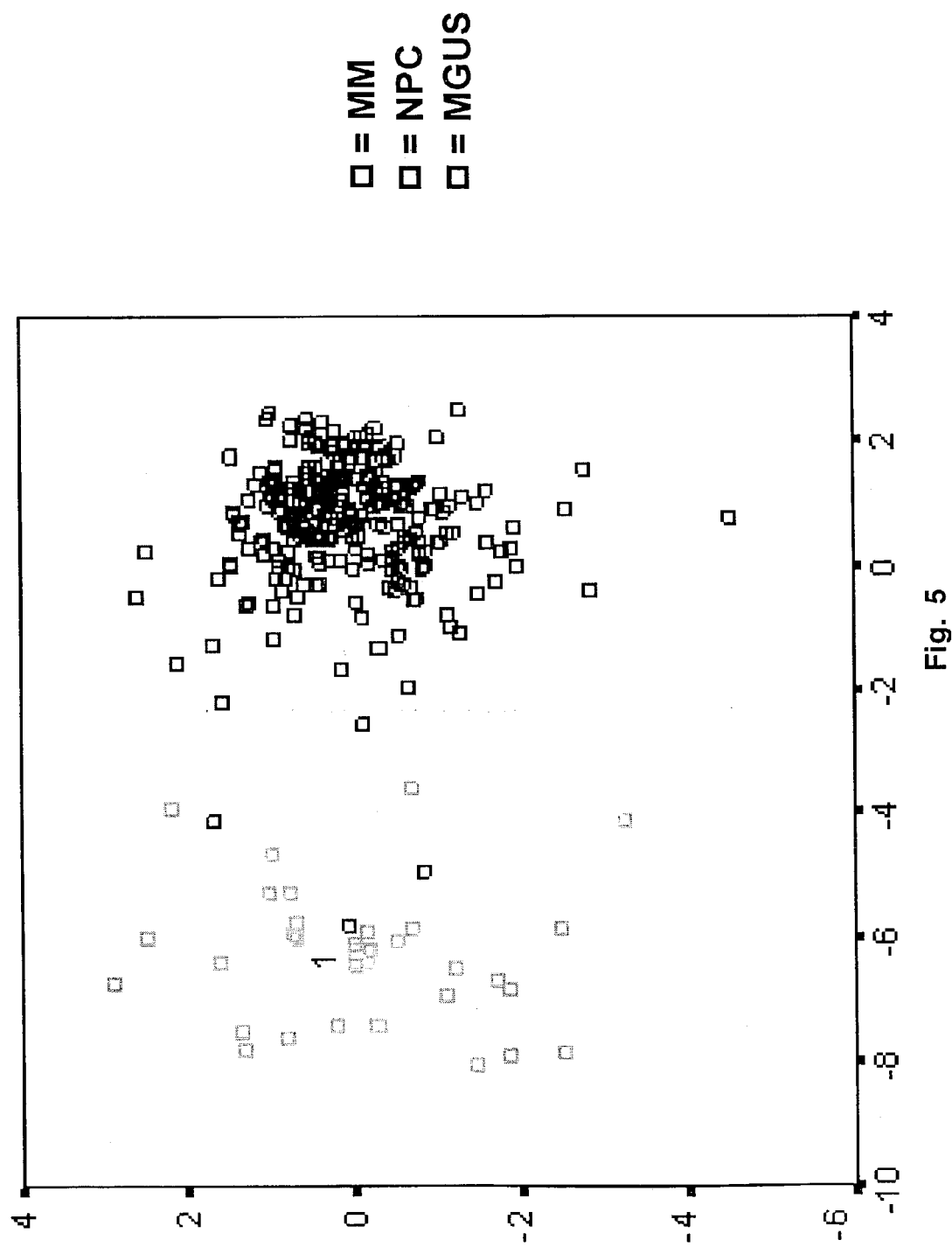
FIG. 5 shows multivariate discriminant analysis of 14 features of all normal plasma cells, MMs, monoclonal gammopathy of undetermined significance and multiple myeloma cell lines. This scatterplot resulted from the orthogonal projection of value per case onto the plane defined by the 2 centers. The green plots represent normal plasma cells; the blue plots represent multiple myeloma plasma cells and multiple myeloma cell lines; the pink plots represent monoclonal gammopathy of undetermined significance.

A validation group was then applied to the model. The multivariate step-wise discriminant analysis correctly classified 116 of 118 (98.31%) primary multiple myeloma samples and 8 of 8 (100%) of human myeloma cell lines as multiple myeloma. In addition, 6 of 6 normal plasma plasma cell samples were classified as normal. Importantly, the model predicted that 6 of 7 monoclonal gammopathy of undetermined significance cases were multiple myeloma with 1 monoclonal gammopathy of undetermined significance case predicted to be normal (FIG. 5). The classification of the 6 monoclonal gammopathy of undetermined significance cases as multiple myeloma has important ramifications in that it suggests that cells in this benign condition have strong similarities to fully transformed cells. These results also have important implications in the eitology of monoclonal gammopathy of undetermined significance and its transition to overt multiple myeloma. The fact that the model classified monoclonal gammopathy of undetermined significance as multiple myeloma is consistent with recent studies that have shown monoclonal gammopathy of undetermined significance has chromosomal abnormalities e.g. translocations of the IGH locus and deletion of chromosome 13 that are also common in multiple myeloma. Future studies will be aimed at identification of gene expression patterns that can actually distinguish monoclonal gammopathy of undetermined significance from multiple myeloma. With the majority of the monoclonal gammopathy of undetermined significance cases being classified as multiple myeloma, the classification of a 1 monoclonal gammopathy of undetermined significance cases as normal may indicate 1) the patient does not have monoclonal gammopathy of undetermined significance or 2) the monoclonal gammopathy of undetermined significance cells represented a minority of the plasma cells in the sample. The monoclonal gammopathy of undetermined significance case and the 2 multiple myeloma cases classified as normal will be followed longitudinally to determine whether in the future the samples will shift to the multiple myeloma group.

In order to further validate the discriminant results, two-dimensional hierarchical clustering was performed on 927 genes with expression in at least one sample. The 118 multiple myeloma samples from the validation group, 32 normal plasma cells, 7 multiple myeloma cell lines, and 7 monoclonal gammopathy of undetermined significance were studied. Along the horizontal axis, experimental samples were arranged such that those with the most similar patterns of expression across all genes were placed adjacent to each other. Surprisingly, the two misclassified multiple myelomas and one monoclonal gammopathy of undetermined significance classified as normal plasma samples by discriminant analysis were also connected to the normal group in the cluster analysis (FIG. 6). This result indicated that the 14 gene discriminant model was consistent with a 927 gene hierarchical cluster model.

A survey of the function of the 14 genes in the above analysis showed several interesting features. The genes are not related in function and thus represent unique and independent genetic markers that can clearly be used as signatures of normal and malignant cells. Genes are associated with the microenvironment (ITGB2), cell transformation (ABL1) and drug resistance (MVP). It is possible that the deregulated expression of these genes may represent fundamental genetic abnormalities in the malignant transformation of plasma cells. For example, the ITGB2 gene encodes the glycoprotein β-2 integrin (CD18) which is critical to the formation of integrin heterodimers known to mediate cell-cell and/or cell-matrix adhesion events. As plasma cells constitutively express ICAM-1 and this molecule can be induced on bone marrow adherent cells, one can envisage a mechanism in which the ITGB2/ICAM-1 adhesion pathway mediates adhesion among plasma cells as well as with cells in the bone marrow microenvironment. In human lymphomas, ITGB2 expression is found on tumor cells in low- and medium-grade malignant lymphomas, whereas absence of ITGB2 seems to be a characteristic of high-grade malignant lymphomas. Similar to other B lymphoma, the absence of ITGB2 might contribute to an escape from immunosurveillance in multiple myeloma.

In summary, the present invention describes a model that makes it possible to diagnosis multiple myeloma by the use of the differential expression of 14 genes. It is currently not clear whether deregulated expressions of these genes are involved in the creation of the malignant phenotype or whether they represent sentinels of some underlying yet to be recognized genetic defect(s). However, the functions of these genes suggest an underlying causal relationship between the deregulated expression and malignancy.

TABLE 6

Fourteen Gene Defining the Optimal Diagnosis Model

| Accession* | Gene Symbol | Wilks' Lambda | F to Remove | P number |
|---|---|---|---|---|
| HT5158 | GMPS | 0.090 | 10.99 | 0.0011 |
| L33930 | CD24 | 0.089 | 8.80 | 0.0034 |

TABLE 6-continued

Fourteen Gene Defining the Optimal Diagnosis Model

| Accession* | Gene Symbol | Wilks' Lambda | F to Remove | P number |
|---|---|---|---|---|
| L42379 | QSCN6 | 0.087 | 4.24 | 0.0409 |
| L77886 | PTPRK | 0.088 | 6.46 | 0.0119 |
| M14636 | PYGL | 0.091 | 12.62 | 0.0005 |
| M26167 | PF4V1 | 0.091 | 12.39 | 0.0005 |
| U10324 | ILF3 | 0.090 | 11.98 | 0.0007 |
| U24577 | PLA2G7 | 0.107 | 44.28 | $3.23 \times 10^{-10}$ |
| U35113 | MTA1 | 0.088 | 6.22 | 0.0135 |
| X16416 | ABL1 | 0.099 | 27.65 | $4.04 \times 10^{-7}$ |
| X64072 | ITGB2 | 0.097 | 24.63 | $1.59 \times 10^{-6}$ |
| X79882 | MVP | 0.098 | 25.83 | $9.19 \times 10^{-7}$ |
| Z22970 | CD163 | 0.088 | 6.08 | 0.0146 |
| Z80780 | H2B | 0.092 | 14.58 | 0.0002 |

Accession number listed are GENBANK® numbers, except the one that begin with "HT", which is provided by the Institute for Genomic Research.

Accession numbers listed are GENBANK® numbers, except the one that begin with "HT", which is provided by the Institute for Genomic Research.

EXAMPLE 10

Differential Expression of 24 Genes Can Accurately Differentiate Gene Expression-Defined Subgroups of Multiple Myeloma The present invention also sought to determine whether expression patterns of a minimum number of genes could be used to clearly differentiate the gene expression-defined subgroups of multiple myeloma identified with hierarchical clustering of over 5,000 genes. As discussed above, two-dimensional cluster analysis of 263 multiple myeloma cases, 14 normal plasma cells, 7 MGUS and 7 multiple myeloma cell lines was performed. The sample dendrogram showed four subgroups of MM1, MM2, MM3 and MM4 containing 50, 75, 67, and 71 patients respectively. Then, the top 120 statistically significant differentially expressed genes as determined by Chi-square and Wilcoxon test of 31 normal plasma cells and 74 newly diagnosed multiple myeloma were chosen for use in a canonical discriminant analysis. By applying a linear regression analysis 24 genes were defined as predictors able to differentiate the multiple myeloma subgroups (Table 7).

The 24 genes predictor model was applied to a training group consisting of multiple myeloma plasma cell samples located in the center of each hierarchical clustering group [total N=129; MM1=23, MM2=33, MM3=34 and MM4=39]. A cross-validation analysis was performed on the training group where samples were removed one at a time from the sample set, and training statistics and expression means for each class of the modified sample set were re-calculated. A predictive value using genes with a P value <0.05 in the modified sample set was generated. The results of this analysis showed that a 100% accurate prediction of the sample types in the training group was obtained.

Figure 7:
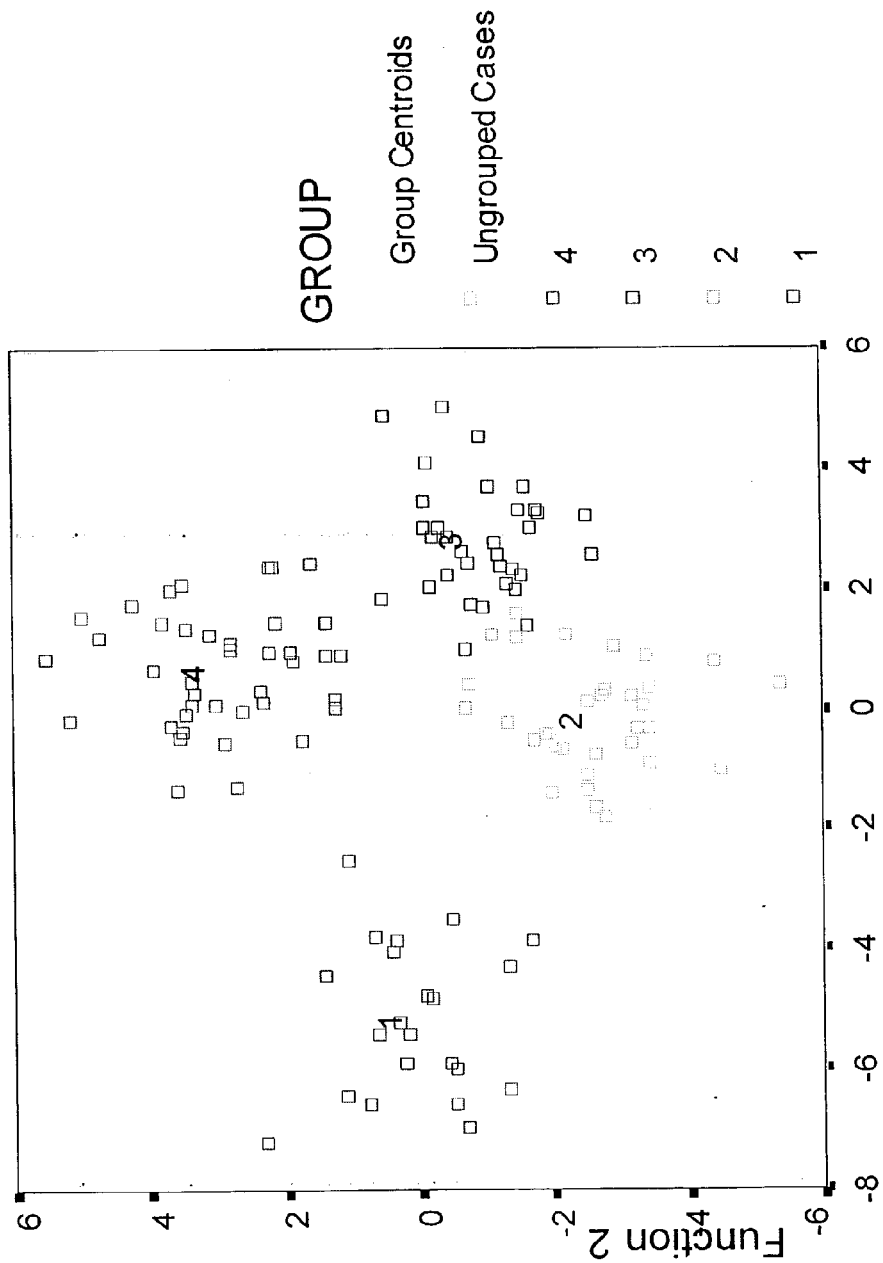
FIG. 7 shows multivariate discriminant analysis of 24 features of all multiple myeloma, monoclonal gammopathy of undetermined significance and multiple myeloma cell lines. This scatterplot resulted from the orthogonal projection of value per case onto the plane defined by the 4 centers. The red plots represent the MM1 subgroup; the green plots represent the MM2 subgroup; the blue plots represent the MM3 subgroup; and the pink plots represent the MM4 subgroup; the light blue plots are ungroup cases; and the large yellow plots represent the group centers.

A validation group was then applied to the model. The multivariate step-wise discriminant analysis correctly classified 116 of 134 (86.56%) primary multiple myeloma samples into different subgroups as compared with the subgroups defined by hierarchical clustering. Importantly, 7 of 7 (100%) of human myeloma cell lines were classified to MM4 as expected. In addition, the model predicted that 5 of 7 MGUS cases were MM1, and the remaining cases were predicted to be MM2 and MM3 respectively (FIG. 7).

TABLE 7

Twenty-Four Genes Defining Subgroups of Multiple Myeloma

| Accession No.* | Gene Symbol | Wilks' Lambda | F to Remove | P value |
|---|---|---|---|---|
| X54199 | GART | 0.004 | 3.13 | 0.0791 |
| M20902 | APOC1 | 0.005 | 4.05 | 0.0462 |
| X89985 | BCL7B | 0.005 | 4.47 | 0.0365 |
| M31158 | PRKAR2B | 0.005 | 5.07 | 0.0260 |
| U44111 | HNMT | 0.005 | 5.68 | 0.0186 |
| X16416 | ABL1 | 0.005 | 6.72 | 0.0106 |
| HT2811 | NEK2 | 0.005 | 8.35 | 0.0045 |
| D16688 | MLLT3 | 0.005 | 8.36 | 0.0045 |
| U57316 | CCN5L2 | 0.005 | 8.49 | 0.0042 |
| U77456 | NAP1L4 | 0.005 | 8.57 | 0.0040 |
| D13645 | KIAA00 | 0.005 | 9.17 | 0.0030 |
| M64590 | GLDC | 0.005 | 9.92 | 0.0020 |
| L77701 | COX17 | 0.005 | 10.01 | 0.0019 |
| U20657 | USP4 | 0.005 | 11.10 | 0.0011 |
| L06175 | P5-1 | 0.005 | 11.11 | 0.0011 |
| M26311 | S100A9 | 0.005 | 11.20 | 0.0011 |
| X04366 | CAPN1 | 0.005 | 11.67 | 0.0009 |
| AC002115 | COX6B | 0.006 | 13.64 | 0.0003 |
| X06182 | C-KIT | 0.006 | 13.72 | 0.0003 |
| M16279 | MIC2 | 0.006 | 16.12 | 0.0001 |
| M97676 | MSX1 | 0.006 | 16.41 | 0.0001 |
| U10324 | LIF3 | 0.006 | 19.66 | 0.0000 |
| S85655 | PHB | 0.007 | 20.63 | 0.0000 |
| X63692 | DNMT1 | 0.007 | 21.53 | 0.0000 |

Accession number listed are GENBANK ® numbers, except the one that begin with "HT", which is provided by the Institute for Genomic Research (TIGR).

Accession number listed are GENBANK® numbers, except the one that begin with "HT", which is provided by the Institute for Genomic Research (TIGR).

EXAMPLE 11

Gene Expression "Spikes" in Subsets of Multiple Myeloma

A total of 156 genes not identified as differently expressed in the statistical analysis of multiple myeloma versus normal plasma cells, yet highly overexpressed in subsets of multiple myeloma, were also identified. A total of 25 genes with an AD spike greater than 10,000 in at least one sample are shown (Table 8). With 27 spikes, the adhesion associated gene FBLN2 was the most frequently spiked. The gene for the interferon induced protein 27, IFI27, with 25 spikes was the second most frequently spiked gene and contained the highest number of spikes over 10,000 (N=14). The FGFR3 gene was spiked in 9 of the 74 cases (FIG. 2A). It was the only gene for which all spikes were greater than 10,000 AD. In fact, the lowest AD value was 18,961 and the highest 62,515, which represented the highest of all spikes. The finding of FGFR3 spikes suggested that these spikes were induced by the multiple myeloma-specific, FGFR3-activating t(4;14)(p21;q32) translocation. To test the above hypothesis, RT-PCR for a t(4;14)(p21;q32) translocation-specific fusion transcript between the IGH locus and the gene MMSET was performed (data not shown). The translocation-specific transcript was present in all 9 FGFR3 spike samples but was absent in 5 samples that did not express FGFR3. These data suggested that the spike was caused by the t(4;14)(p21;q32) translocation.

The CCND1 gene was spiked with AD values greater than 10,000 in 13 cases. TRI-FISH analysis for the t(11;14)(q13;q32) translocation was performed (Table 9). All 11 evaluable samples were positive for the t(11;14)(q13;q32) translocation by TRI-FISH; 2 samples were not analyzable due to loss of cell integrity during storage. Thus, all FGFR3 and CCND1 spikes could be accounted for by the presence of either the t(4;14)(p21;q32) translocation or the t(11;14)(q13;q32) translocation respectively.

Figure 2:
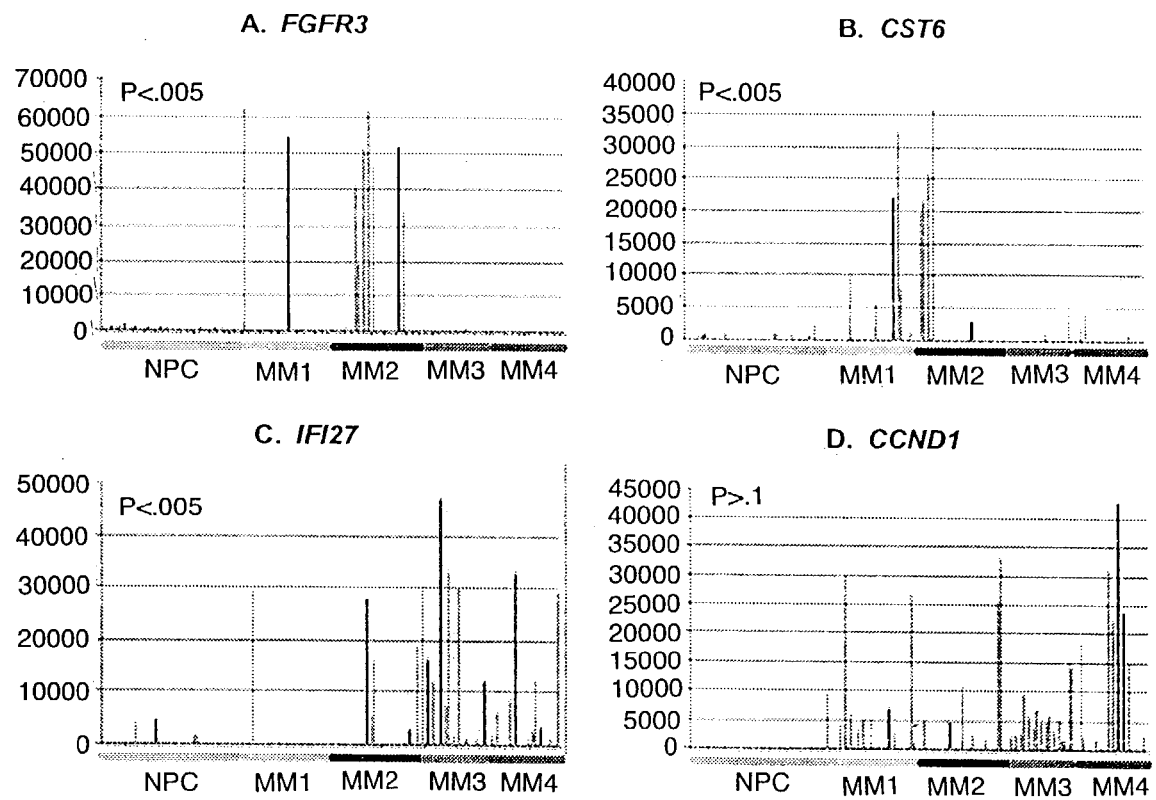
FIG. 2 shows the spike profile distributions of FGFR3, CST6, IFI27, and CCND1 gene expression. The normalized average difference (AD) value of fluorescence intensity of streptavidin-phycoerythrin stained biotinylated cRNA as hybridized to probes sets is on the vertical axis and samples are on the horizontal axis. The samples are ordered from left to right: normal plasma cells (NPCs) (green), MM1 (light blue), MM2 (dark blue), MM3 (violet), and MM4 (red). Note relatively low expression in 31 plasma cells and spiked expression in subsets of multiple myeloma samples. The P values of the test for significant nonrandom spike distributions are noted.

Next, the distribution of the FGFR3, CST6, IFI27, and CCND1 spikes within the gene expression-defined multiple myeloma subgroups was determined (FIG. 2). The data showed that FGFR3 and CST6 spikes were more likely to be found in MM1 or MM2 (P<0.005) whereas the spikes for IFI27 were associated with an MM3 and MM4 distribution (P<0.005). CCND1 spikes were not associated with any specific subgroup (P>0.1). It is noteworthy that both CST6 and CCND1 map to 11q13 and had no overlap in spikes. It remains to be tested whether CST6 overexpression is due to a variant t(11;14)(q13;q32) translocation. The five spikes for MS4A2 (CD20) were found in either the MM1 (3 spikes) or MM2 (2 spikes) subgroups (data not shown).

Figure 3A:
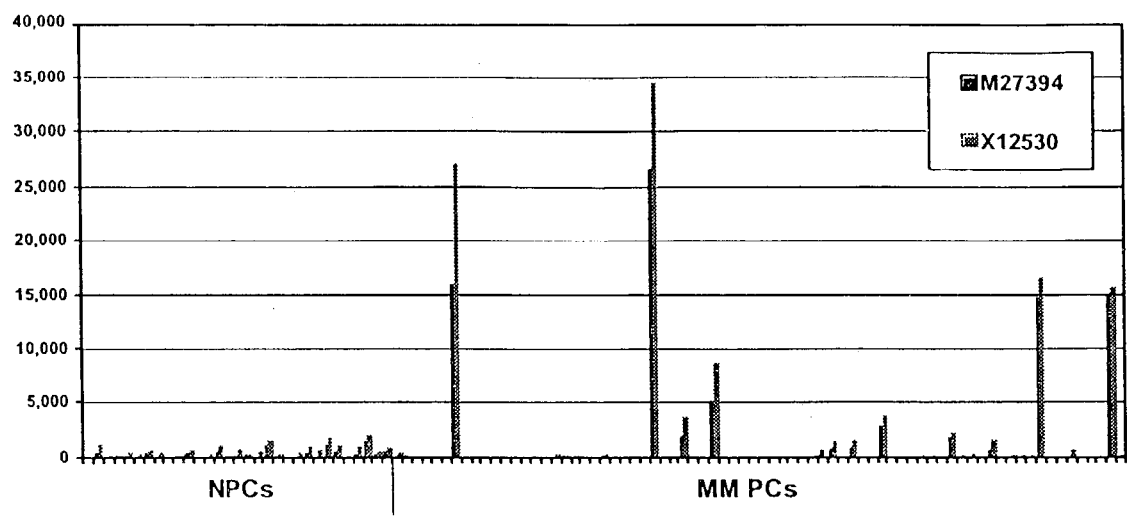
FIG. 3A shows a GENECHIP® HUGENEFL® (DNA microarray) analysis of MS4A2 (CD20) gene expression. The normalized average difference (AD) value of fluorescence intensities of streptavidin-phycoerythrin stained biotinylated cRNA as hybridized to two independent probes sets (accession numbers M27394 (blue) and X12530 (red) located in different regions of the MS4A2 gene is on the vertical axis and samples are on the horizontal axis. Note relatively low expression in 31 normal plasma cells (NPCs) and spiked expression in 5 of 74 multiple myeloma samples (multiple myeloma plasma cells). Also note similarity in expression levels detected by the two different probe sets.
Figure 3B:
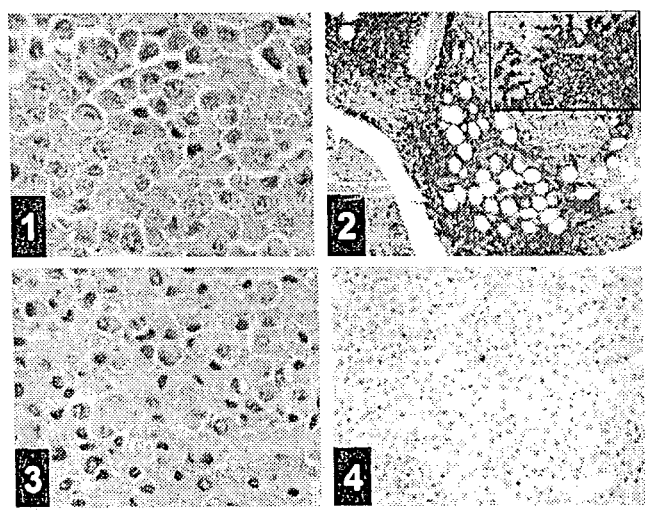
FIG. 3B shows immunohistochemistry for CD20 expression on clonal multiple myeloma plasma cells: (1) bone marrow biopsy section showing asynchronous type multiple myeloma cells (H&E, ×500); (2) CD20+ multiple myeloma cells (×100; inset ×500); (3) biopsy from a patient with mixed asynchronous and Marschalko-type multiple myeloma cells (H&E, ×500); and (4) CD20+ single lymphocyte and CD20− multiple myeloma cells (×200). CD20 immunohistochemistry was examined without knowledge of clinical history or gene expression findings.
Figure 4:
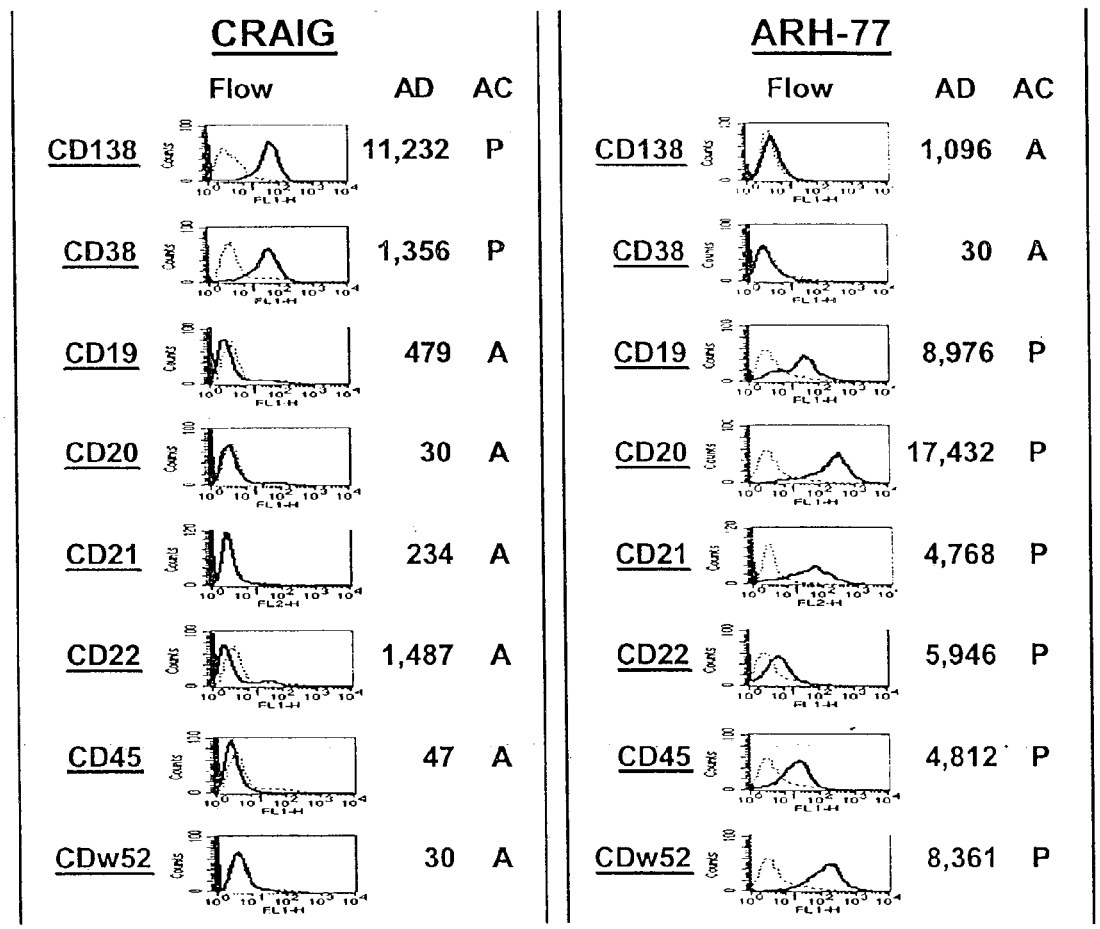
FIG. 4 shows the gene expression correlates with protein expression. Gene and protein expression of CD markers known to be differentially expressed during B-cell differentiation were compared between the multiple myeloma cell line CAG (left panel) and the Epstein-Barr virus (EBV) transformed B-lymphoblastoid line ARH-77 (right panel). In both panels, the 8 CD markers are listed in the left column of each panel. Flow cytometric analysis of protein expression is presented in the second column; the average difference (AD) and absolute call (AC) values of gene expression are presented in the third and fourth columns. Note the strong expression of both the gene and protein for CD138 and CD38 in the CAG cells but the low expression in the ARH-77 cells. The opposite correlation is observed for the remaining markers.

The gene MS4A2 which codes for the CD20 molecule was also found as a spiked gene in four cases (FIG. 3A). To investigate whether spiked gene expression correlated with protein expression, immunohistochemistry for CD20 was performed on biopsies from 15 of the 74 multiple myeloma samples (FIG. 3B). All four cases that had spiked MS4A2 gene expression were also positive for CD20 protein expression, whereas 11 that had no MS4A2 gene expression were also negative for CD20 by immunohistochemistry. To add additional validation to the gene expression profiling, a comparison of CD marker protein and gene expression in the multiple myeloma cell line CAG and the EBV-transformed lymphoblastoid cell line ARH-77 were also performed (FIG. 4). The expression of CD138 and CD38 protein and gene expression was high in CAG but absent in ARH-77 cells. On the other hand, expression of CD19, CD20, CD21, CD22, CD45, and CDw52 was found to be strong in ARH-77 and absent in CAG cells. The nearly 100% coincidence of FGFR3 or CCND1 spiked gene expression with the presence of the t(4;14)(p14;q32) or t(11;14)(q13;q32) translocation; the strong correlation of CD20 and MS42A gene expression in primary multiple myeloma; and strong correlation of CD marker protein and gene expression in B cells and plasma cells represent important validations of the accuracy of the gene expression profiling disclosed herein.

TABLE 8

Genes with "Spiked" Expression in Plasma Cells from Newly Diagnosed Multiple Myeloma Patients

| Accession No.* | Function | Gene Symbol | # of Spikes | Spikes >10K | Max Spike |
|---|---|---|---|---|---|
| M64347 | signaling | FGFR3 | 9 | 9 | 62,515 |
| U89922 | immunity | LTB | 4 | 2 | 49,261 |
| X67325 | interferon signaling | IF127 | 25 | 14 | 47,072 |
| X59798 | cell cycle | CCND1 | 6 | 13 | 42,814 |
| U62800 | cysteine protease inhibitor | CST6 | 17 | 6 | 36,081 |
| U35340 | eye lens protein | CRYBB1 | 4 | 1 | 35,713 |
| X12530 | B-cell signaling | MS4A2 | 5 | 5 | 34,487 |
| X59766 | unknown | AZGP1 | 18 | 4 | 28,523 |
| U58096 | unknown | TSPY | 4 | 1 | 23,325 |
| U52513 | interferon signaling | IFIT4 | 5 | 2 | 21,078 |
| X76223 | vesicular trafficking | MAL | 19 | 5 | 20,432 |
| X92689 | O-linked glycosylation | GALNT3 | 4 | 1 | 18,344 |
| D17427 | adhesion | DSC3 | 8 | 7 | 17,616 |
| L11329 | signaling | DUSP2 | 14 | 1 | 15,962 |
| L13210 | adhesion, macrophage lectin | LGALS3BP | 8 | 2 | 14,876 |

TABLE 8-continued

Genes with "Spiked" Expression in Plasma Cells from Newly Diagnosed Multiple Myeloma Patients

| Accession No.* | Function | Gene Symbol | # of Spikes | Spikes >10K | Max Spike |
|---|---|---|---|---|---|
| U10991 | unknown | G2† | 7 | 1 | 14,815 |
| L10373 | integral membrane protein | TM4SF2 | 4 | 2 | 14,506 |
| U60873 | unknown | 137308 | 12 | 1 | 12,751 |
| M65292 | complement regulation | HFL1 | 9 | 1 | 12,718 |
| HT4215 | phospholipid transport | PLTP | 23 | 1 | 12,031 |
| D13168 | growth factor receptor | ENDRB | 18 | 1 | 11,707 |
| AC002077 | signaling | GNAT1 | 21 | 1 | 11,469 |
| M92934 | growth factor | CTGF | 4 | 1 | 11,201 |
| X82494 | adhesion | FBLN2 | 27 | 7 | 10,648 |
| M30703 | growth factor | AR | 5 | 1 | 10,163 |

*Accession numbers listed are GENBANK ® numbers, except those beginning with "HT", which are provided by the Institute for Genomic Research (TIGR). †Gene symbol not HUGO approved.

Accession number listed are GENBANK® numbers, except the one that begin with "HT", which is provided by the Institute for Genomic Research (TIGR). † Gene symbol not HUGO approved.

TABLE 9

Correlation of CCND1 Spikes with FISH-Defined t (11; 14) (q13; q32)

| GC PT* | CCND1 Spike (AD value)† | FISH t (11; 14) | Percent PCs with Translocation | Cells Counted |
|---|---|---|---|---|
| P168 | 42,813 | Yes | 59% | 113 |
| P251 | 33,042 | Yes | 80% | 124 |
| P91 | 31,030 | Not done | — | — |
| P99 | 29,862 | Yes | 65% | 111 |
| P85 | 26,737 | Yes | 92% | 124 |
| P241 | 25,611 | Yes | 96% | 114 |
| P56 | 23,654 | Yes | 100% | 106 |
| P63 | 22,358 | Yes | 98% | 104 |
| P199 | 18,761 | Yes | 60% | 35 |
| P107 | 15,205 | Yes | 100% | 147 |
| P75 | 14,642 | Yes | 100% | 105 |
| P187 | 14,295 | Yes | 25% | 133 |
| P124 | 10,594 | Not done | — | — |

*GC PT = patient identifier; †AD = average difference call.

EXAMPLE 12

Endothelin B Receptor as Potential Therapeutic Target of Multiple Myeloma

Figure 8A:
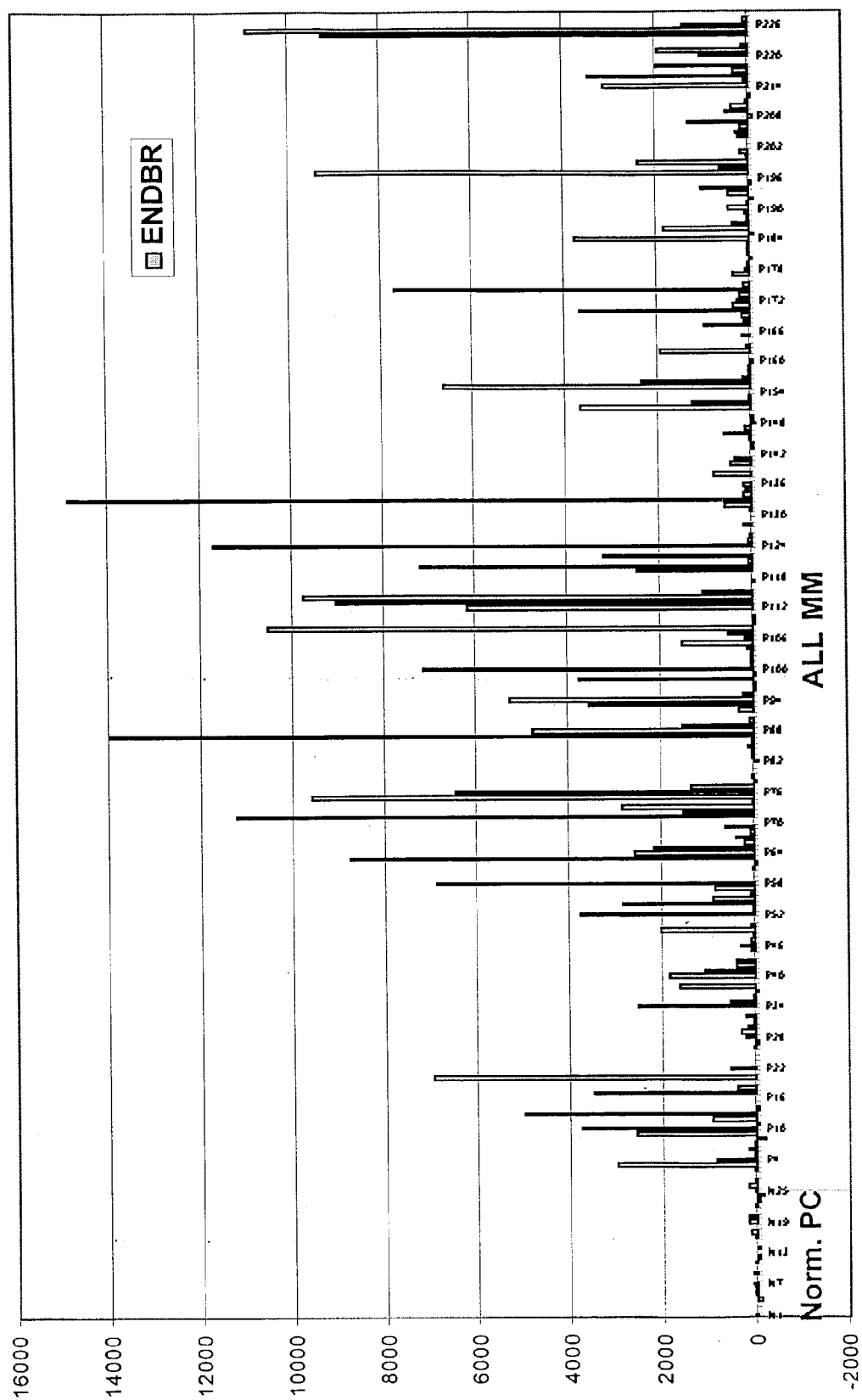
FIG. 8A shows endothelin B receptor (ENDBR) expression in normal plasma cells and in approximately 200 myeloma patients starting with P1 through P226 as indicated by the mean fluorescent intensity of the microarry data depicted on the Y axis.
Figure 8B:
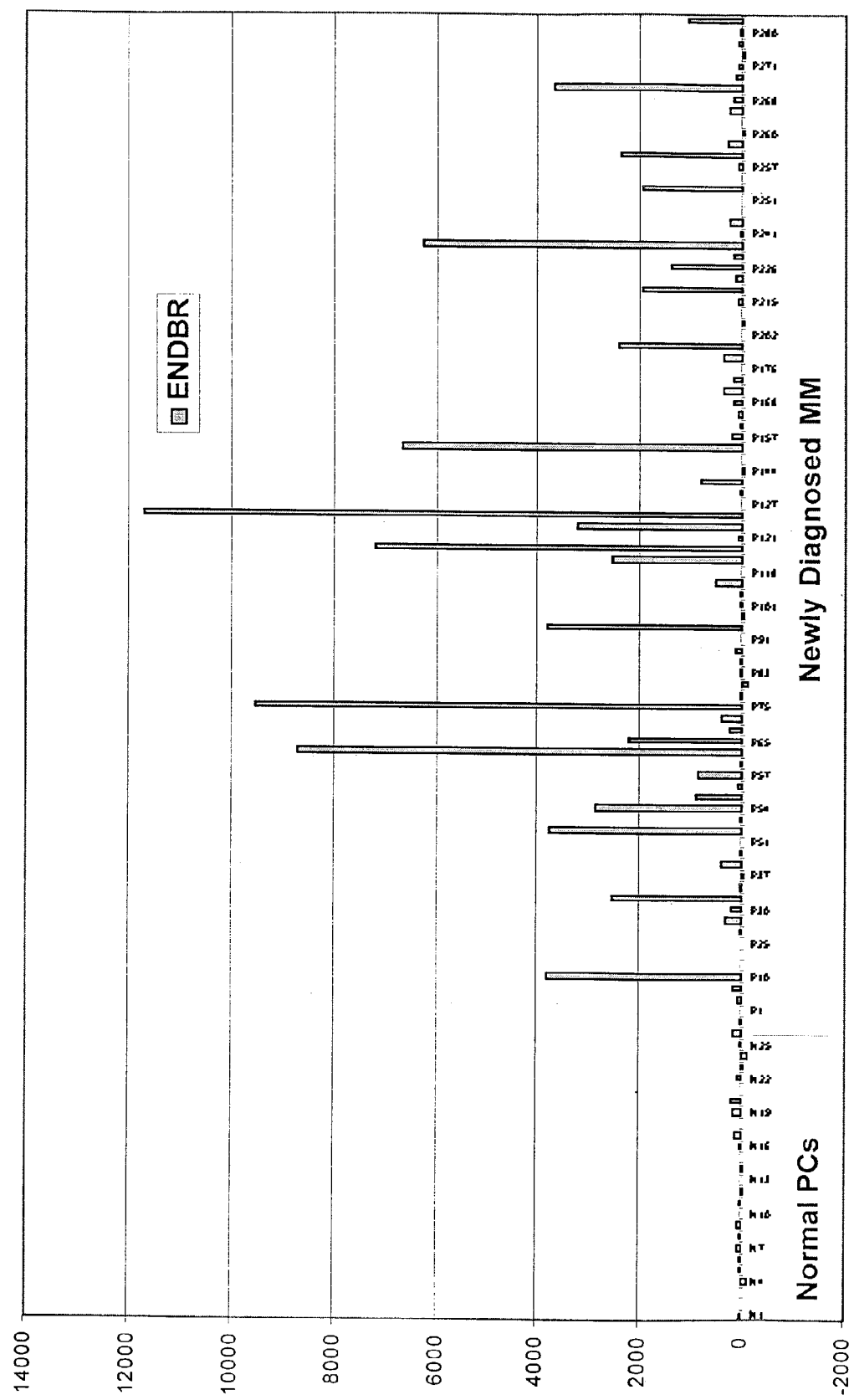
FIG. 8B shows endothelin B receptor expression in normal plasma cells and in newly diagnosed myeloma patients.

As disclosed above, the present invention has identified a number of genes that have significantly different expression levels in plasma cells derived from multiple myeloma compared to those of normal control. Genes that are significantly up-regulated or down-regulated in multiple myeloma are potential therapeutic targets of multiple myeloma. Examples of these genes are listed in Tables 4, 5 and 8. Among these differentially expressed genes is endothelin B receptor (ENDBR). This gene was not expressed in normal plasma cells, but does show highly elevated expression in a subset of myeloma. In fact, this gene now appears to be highly expressed in between 30-40% of myeloma patients. FIG. 8 shows a comparison of ENDBR expression in normal plasma cells and in approximately 200 myeloma patients starting with P1 through P226. ENDBR was either off or highly expressed in multiple myeloma patients (FIG. 8A). Levels of ENDBR expression levels were approximately the same in newly diagnosed and previously treated patients, suggesting that the activation is not a progression event (FIG. 8B).

Several important features of ENDBR should be noted. The ENDBR gene is located on chromosome 13. This is of potential significance given that abnormalities in chromosome 13 such as translocation or deletions represent one of the most powerful negative risk factors in multiple myeloma. Thus, it is possible that the hyperactivation of ENDBR expression could be an indicator of poor prognosis for multiple myeloma. There are also extensive reports linking endothelin signaling to cell growth, and endothelins have been shown to activate several key molecules with documented pathological roles in plasma cell tumorigenesis. Of note are the c-MYC oncogene, a gene that is activated in 100% of mouse plasmacytomas and hyperactivated in many primary human myeloma cells, and IL-6 which is a major growth and survival factor for myeloma cells. The endothelins also appear to exert their signaling through the phospholipase C pathway, a major signaling pathway in B-cells. Moreover, a recent paper reported that blocking endothelin signaling resulted in inhibition of the proliferation of Kaposi's sarcoma cells.

Figure 9A:
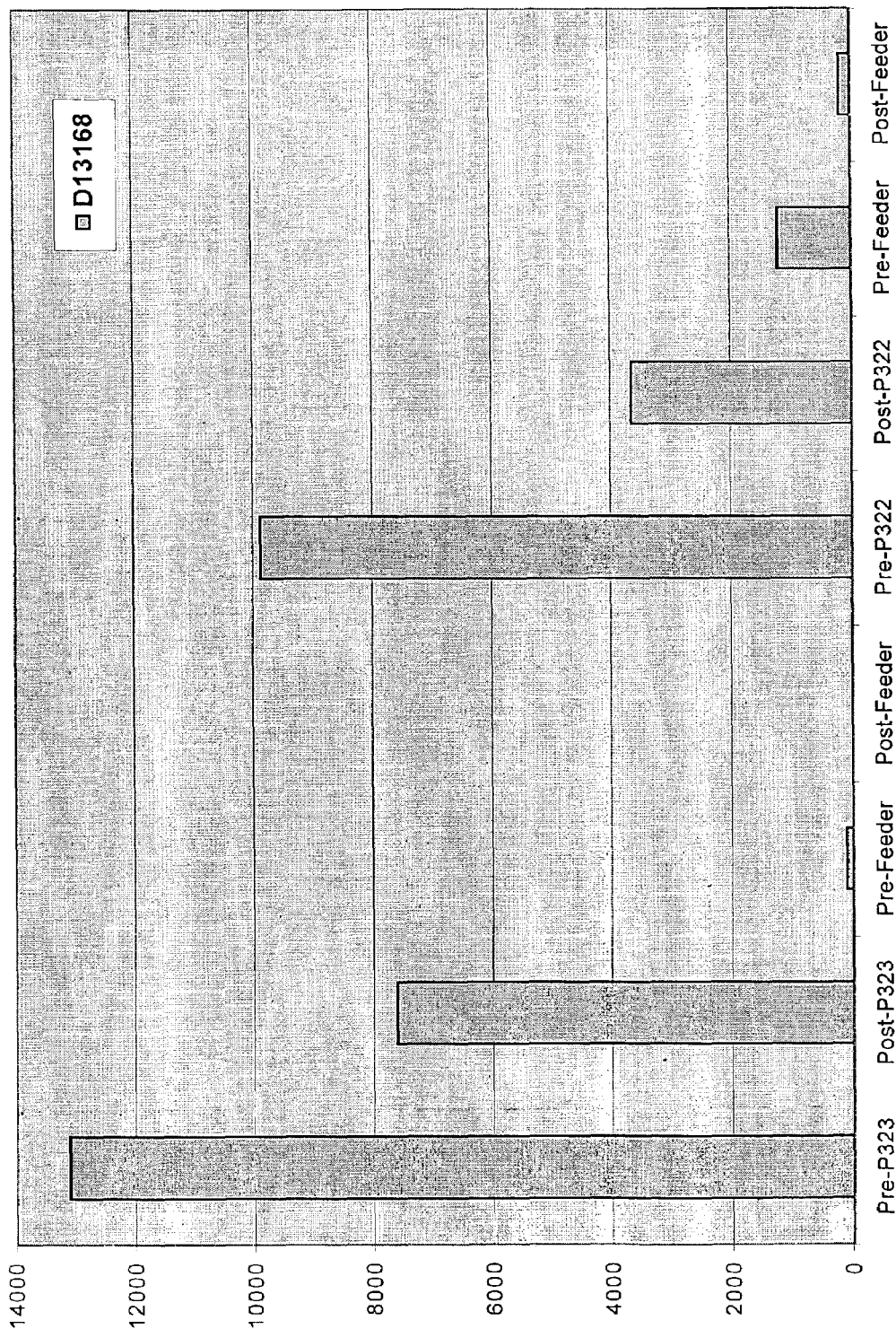
FIG. 9A shows the expression of endothelin B receptor (ENDBR) in feeder cells and myeloma cells P323 and P322 before and after co-culture.
Figure 9B:
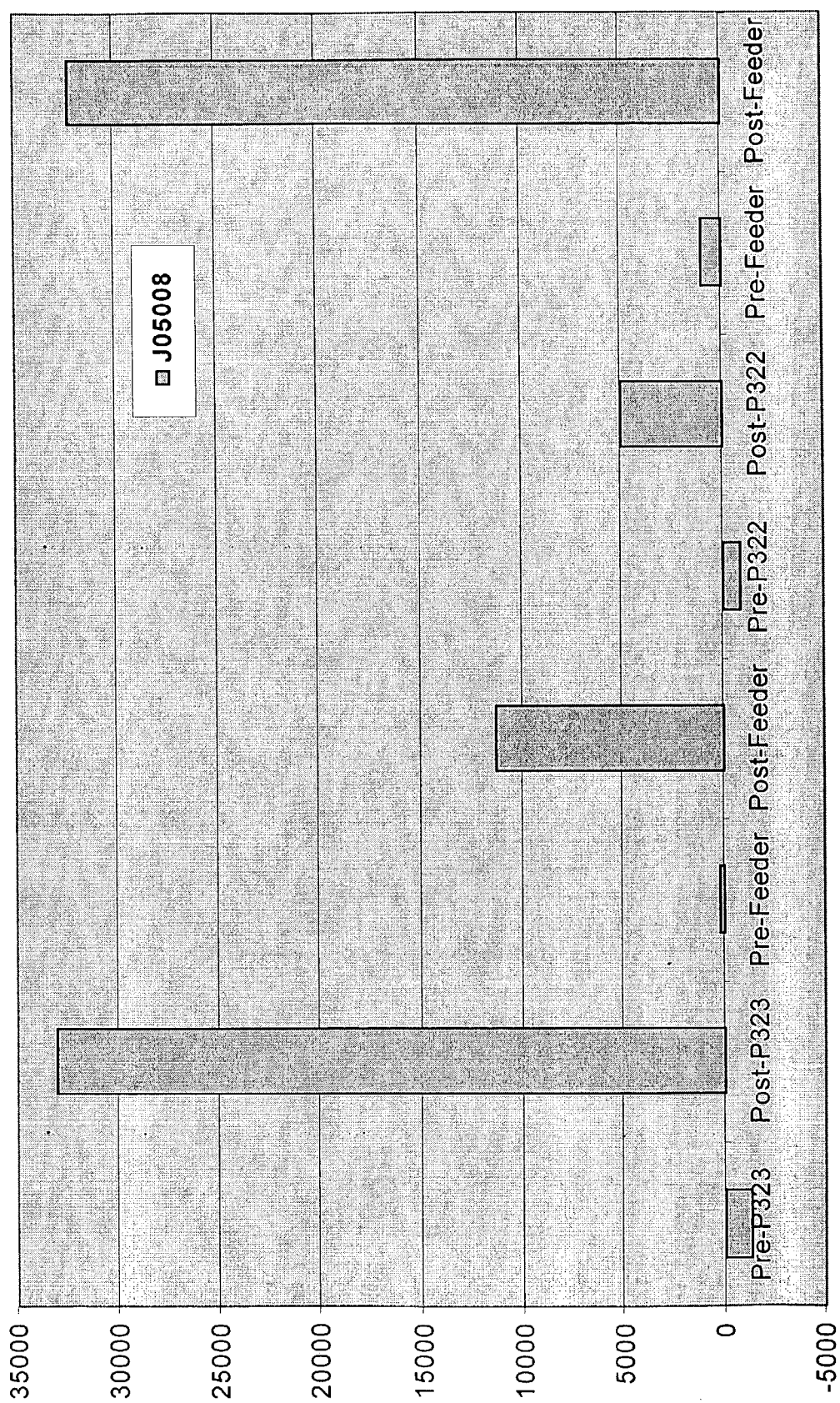
FIG. 9B shows the expression of endothelin 1 in feeder cells and myeloma cells P323 and P322 before and after co-culture.

When the tumor cells of multiple myeloma patients were taken out of the microenvironment of bone marrow, the tumor cells did not appear to express endothelins genes in a large proportion of the population. They lack expression of the endothelin 1, 2 and 3 in most cases. However, when the myeloma cells were taken out of the bone marrow and cultured for 48-72 hours on proprietary feeder layer that mimics the bone marrow microenvironment, endothelin 1 gene expression was massively up-regulated in both the myeloma cells P323 and P322 as well as the feeder layer (FIG. 9). Hence, a major variable within multiple myeloma may be the availability of endothelins. Enhanced production of endothelins coupled with up-regulated expression of ENDBR in local areas may contribute to the neoplastic phenotype of multiple myeloma, and blocking endothelins and endothelin receptor interaction may disrupt the development of the malignant phenotype.

EXAMPLE 13

Comparative Gene Expression Profiling of Human Plasma Cell Differentation

Examples 13-15 describe global gene expression profiling that reveals distinct changes in transcription associated with human plasma cell differentiation. Data presented below demonstrate for the first time that highly purified plasma cells could be isolated from two unique hematopoietic organs, tonsil and bone marrow. This purification of millions of cells eliminated background "noise" from non-specific cell types (see FIG. 10), thereby allowing accurate genetic profile and characterization of these samples using highly sensitive gene expression profiling technology. The results disclosed herein characterized molecular transcription changes associated with different cell stages and especially distinguishing differences in plasma cell, a cell previously thought to represent an end-stage differentiation product based on morphological criterion.

The CD19$^+$ tonsil B cells and CD138$^+$ plasma cells isolated from tonsil and bone marrow used in the study represent homogeneous populations with unique phenotypic characteristics. Thus, results presented are based on well-characterized cells as shown by flow cytometry, morphology, and expression of cIg. These results are important little is known about plasma cells, most likely due to their scarcity with most previous studies focusing only on flow cytometric characterizations.

Another unique finding from the results is that B cells and plasma cells segregated into two branches using a hierarchical gene expression cluster analysis. Further, within the plasma cell branch, tonsil plasma cells could be distinguished from bone marrow plasma cells, indicating that the cells represent unique stages of development as suspected from their derivation from unique hematopoietic organs. Genes identified herein (e.g., cell surface markers and transcription factors) matched those previously identified as distinguishing late-stage B cell development. In addition to the novel genes found, previously identified genes followed expected patterns of up- and down-regulation and matched those genes already shown to be linked to plasma cell differentiation or essential transcription factors for plasma cell differentiation.

Although cells at distinct stages of B cell development express CD19, it is likely that the majority of the tonsil B cells studied here represent germinal center centroblasts. It is known that centrocytes and centroblasts of germinal centers can be differentiated based on the expression of CD44 (centrocytes, CD44$^+$; centroblasts, CD44$^-$). Expression of the CD44 gene was undetectable in the tonsil B cell samples used in this study. In addition, the high level of expression of genes linked to proliferation, e.g. MKI67, PCNA, and CCNB1 (data not shown) suggests blasts make up the largest population of cells among the tonsil B cells. Finally, MYBL, whose expression is a marker of CD38$^+$ CD39$^-$ centroblasts, was found to be highly expressed in the tonsil B cells, down-regulated in tonsil plasma cells (P=0.00068), and extinguished in bone marrow plasma cells. Because centroblasts have already undergone switch recombination, the tonsil B cells studied here represent an optimal late stage B cell population to use in a comparative study of gene expression changes associated with early plasma cell differentiation.

Figure 10:
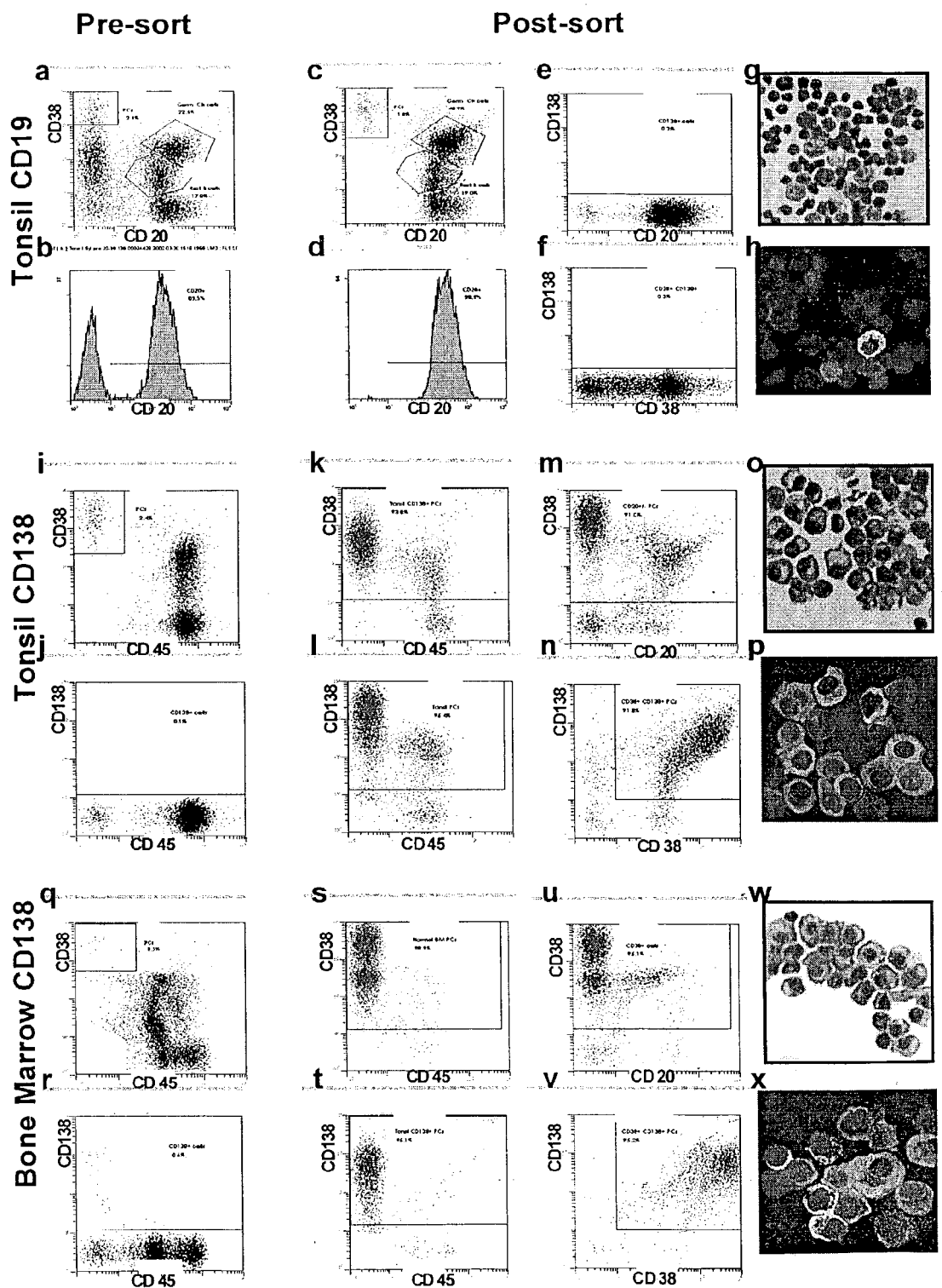
FIG. 10 shows flow cytometric, immunofluorescence and cytological analysis of normal B cell and plasma cell samples.

A representative analysis of normal cell types used in this study is presented in FIG. 10. FACs analysis of the tonsil preparations before sorting indicated that CD20$^{hi}$/CD38$^{lo}$ cells represented 70% and CD38$^+$/CD20$^-$ cells represented 30% of the population (FIGS. 10$a$, $b$). After anti-CD19 immunomagnetic bead selection, the CD20$^{hi}$/CD38$^{lo/-}$ cells were enriched to 98% and the CD38$^+$/CD20$^-$, CD138$^-$/CD20$^+$, and CD138$^-$/CD38$^+$ fractions represented 1% of the population (FIGS. 10$b$, $c$, $e$, $f$). Cell morphology of the purified fraction also showed that the majority of cells had typical B cell morphology (FIG. 10$g$). Immunofluorescence microscopy with anti-kappa and anti-lambda antibodies indicated a slight contamination with cIg$^+$ CD19$^+$ cells (FIG. 10$h$).

Before tonsil plasma cell isolation, FACs analysis of the tonsil mononuclear fractions indicated that CD38$^{hi}$/CD45$^-$ (FIG. 10$i$) and CD138$^{hi}$/CD45$^-$ cells (FIG. 10$j$) represented 2.4% of the population. After anti-CD138 immunomagnetic bead sorting, cells with a plasma cell phenotype that was either CD38$^{hi}$/CD45$^{lo}$ (95%), CD138$^{hi}$/CD45$^{lo}$ (94%), CD38$^{h}$/CD20$^{lo}$ (91%), or CD138$^{hi}$/CD38$^{hi}$ (92%) were greatly enriched (FIGS. 10$k$, $l$, $m$, $n$). The tonsil CD138-selected cells were also found to have a typical plasma cell morphology with increased cytoplasmic to nuclear ratio of prominent perinuclear Hoff or endoplasmic reticulum (FIG. 10$o$) and >95% of the cells were cIg positive (FIG. 10$p$).

FACs analysis prior to anti-CD138 immunomagnetic bead sorting of bone marrow mononuclear cell samples showed similar but distinct profiles in comparison with the tonsil preparations. CD38$^{hi}$/CD45$^{int}$ and CD138$^{hi}$/CD45$^{int}$ fractions showed more cells with lower expression of CD45 and a higher percentage of CD138$^+$ cells in the bone marrow plasma cells (FIGS. 10$q$, $r$). FACS analysis after purification showed that the CD38$^{hi}$/CD45$^-$ and CD38$^{hi}$/CD20$^{lo}$ cells were enriched to 99% and 91%, respectively (FIGS. 10$s$, $u$). Differences between tonsil plasma cells and bone marrow plasma cells after sorting were also evident, in that whereas the tonsil plasma cells had clear evidence of CD38$^+$/CD45$^+$ and CD38$^+$/CD20$^+$ cells, these fractions were greatly reduced in the bone marrow CD138-selected cells. Bone marrow plasma cells also expressed higher levels of CD38 than the tonsil plasma cells (FIGS. 10$s$, $k$). The CD138$^{hi}$/CD45$^-$ and CD138$^{hi}$/CD38$^{hi}$ populations represented 96% and 95% of the bone marrow plasma cell population (FIGS. 10$t$, $v$), again with a reduced amount of CD45$^+$ cells and higher percentage of CD38$^+$ cells as compared with tonsil plasma cells. As with the tonsil plasma cells, the majority of the bone marrow cells had plasma cell morphology (FIG. 10$w$) and were cIg positive (FIG. 10$x$). Thus, immunomagnetic bead selection resulted in the purification of a relatively homogenous tonsil B cell population and distinct plasma cell populations from two different organs, likely representing cells at different stages of maturation.

Having demonstrated the phenotypic characteristics of the cells, the global mRNA expression was then analyzed in 7 tonsil B cell, 11 tonsil plasma cell, and 31 bone marrow plasma cell samples using the Affymetrix high-density oligonucleotide microarray interrogating approximately 6800 named and annotated genes. The mean value of the AD expression level of genes for the CD markers used in the cell analysis, as well as other CD markers, chemokine receptors, apoptosis regulator, and a panel of transcription factors were analyzed across the normal samples (Table 10). CD45 was found to be highly expressed on tonsil B cells, with lower expression on tonsil plasma cells, and absent on bone marrow plasma cells. The genes for CD20, CD79B, CD52, and CD19 showed CD45-like expression patterns with progressive down-regulation from tonsil B cells to tonsil plasma cells. Although CD21 showed no significant change from tonsil B cells to tonsil plasma cells, the gene was down-regulated in bone marrow plasma cells. CD22, CD83, and CD72 showed progressive down-regulation.

Consistent with the FACS analysis, Syndecan-1 (CD138) and CD38, key plasma cell differentiation antigens, were absent or weakly expressed on tonsil B cells, with intermediate levels on tonsil plasma cells, and highest expression on bone marrow plasma cells. The intermediate level of CD138 expression is likely a direct reflection of the heterogeneous mixture of CD138$^+$ cells in the tonsil plasma cell fraction (see above) with some cells being highly CD138$^+$ and others weakly positive but still able to be sorted based on surface expression of CD138. CD38 expression showed the progressive increase seen with CD138 in the normal cells.

It was also observed that the CD63 gene was significantly up-regulated in bone marrow plasma cells. This is the first indication that this marker may be differentially regulated during plasma cell differentiation. The gene for CD27 showed significant up-regulation from the B cell to tonsil plasma cell transition, whereas bone marrow plasma cells and tonsil plasma cells showed similar levels.

Transcription factors differentially expressed in plasma cell development showed the expected changes. IRF4 and XBP1 were significantly up-regulated in tonsil and bone marrow plasma cells and CTIIA, BCL6, and STAT6 were down-regulated in the plasma cell samples. BSAP (PAX5)

did not show the expected changes, but it is believed that this was due to an ineffective probe set for the gene because the BSAP target gene, BLK, did show the expected down-regulation in the tonsil and bone marrow plasma cells. Interestingly, whereas MYC showed significant down-regulation in the tonsil B cell to tonsil plasma cell transition, the gene was reactivated in bone marrow plasma cells to levels higher than seen in the tonsil B cells. Whereas the chemokine receptors CXCR4 and CXCR5 showed down-regulation in the tonsil B cell to tonsil plasma cell transition, CXCR4 showed a MYC-like profile in that the gene was reactivated in bone marrow plasma cells. The BCL2 homologue BCL2A1 also showed the expected changes. Thus, gene expression patterns of cell surface markers are consistent with phenotypic patterns and genes known to be strongly associated with plasma cell differentiation showed anticipated patterns. These data support the notion that the tonsil B cells, tonsil plasma cells, and bone marrow plasma cells represent distinct stages of B-cell differentiation and that gene expression profiling of these cells can be used to gain a better understanding of the molecular mechanisms of differentiation.

TABLE 10

Gene Expression Of CD Marker And Proteins Known To Be Differentially Expressed During Plasma Cell Differentiation

| Accession | Symbol | TBC | TPC | BPC |
|---|---|---|---|---|
| Y00062 | CD45 | 11495 ± 2198 | 4979 ± 2522 | 1385 ± 706 |
| M27394 | CD20 | 23860 ± 5494 | 3799 ± 2977 | 289 ± 358 |
| M89957 | CD79B | 14758 ± 3348 | 4696 ± 2440 | 1243 ± 1357 |
| X62466 | CD52 | 14576 ± 2395 | 4348 ± 2074 | 2831 ± 1002 |
| M84371 | CD19 | 12339 ± 1708 | 6174 ± 1345 | 2852 ± 852 |
| M26004 | CD21 | 8909 ± 1640 | 5434 ± 4053 | 458 ± 140 |
| X59350 | CD22 | 10349 ± 1422 | 5356 ± 1610 | 1929 ± 612 |
| Z11697 | CD83 | 9201 ± 1900 | 2380 ± 1087 | 392 ± 403 |
| M54992 | CD72 | 6177 ± 1620 | 865 ± 554 | 454 ± 548 |
| Z48199 | CD138 | 719 ± 519 | 9935 ± 3545 | 24643 ± 6206 |
| D84276 | CD38 | 3122 ± 967 | 9833 ± 3419 | 14836 ± 3462 |
| X62654 | CD63 | 2310 ± 431 | 6815 ± 1582 | 16878 ± 3305 |
| M63928 | CD27 | 6235 ± 1736 | 15937 ± 6691 | 16714 ± 4442 |
| M31627 | XBP1 | 12978 ± 1676 | 54912 ± 13649 | 49558 ± 10798 |
| U52682 | IRF4 | 1863 ± 630 | 8422 ± 3061 | 11348 ± 3118 |
| U00115 | BCL6 | 7979 ± 1610 | 3303 ± 2070 | 618 ± 335 |
| X74301 | CIITA | 1553 ± 263 | 236 ± 217 | 113 ± 82 |
| U16031 | STAT6 | 1314 ± 512 | 386 ± 335 | 191 ± 187 |
| S76617 | BLK | 3654 ± 1551 | 388 ± 592 | 95 ± 86 |
| X68149 | CXCR5 | 3381 ± 1173 | 183 ± 299 | 92 ± 183 |
| U29680 | BCL2A1 | 3290 ± 1073 | 1121 ± 817 | 483 ± 209 |
| L00058 | MYC | 1528 ± 474 | 348 ± 239 | 2103 ± 903 |
| L06797 | CXCR4 | 11911 ± 2093 | 6673 ± 3508 | 18033 ± 5331 |

Accession = GENBANK ® accession number. Symbol = HUGO approved gene symbol. The numbers in the columns under the tonsil B cell (TBC), tonsil plasma cell (TPC), and bone marrow plasma cell (BPC) samples represent the mean average difference (AD) value ± the standard deviation (STD) for the given gene. Differences in expression across comparisons were significant (P < 0.01) unless indicated in bold.

Accession=GENBANK® accession number. Symbol=HUGO approved gene symbol.

EXAMPLE 14

Identification of Differentially Expressed Genes in the Tonsil B Cell to Tonsil Plasma Cell and in the Tonsil Plasma Cell to Bone Marrow Plasma Cell Transitions A more detailed and comprehensive evaluation was performed to determine gene expression changes that accompany the transition of tonsil B cells to tonsil plasma cells and the changes that occur as the immature tonsil plasma cells exit the lymph node germinal center and migrate to the bone marrow. To reveal global expression distinctions among the samples, hierarchical cluster analysis was performed with 4866 genes in 7 tonsil B cell, 7 tonsil plasma cell, and 7 bone marrow plasma cell cases (FIG. 11). As expected, this analysis revealed a major division between the tonsil B cell samples and plasma cell samples with the exception of one tonsil plasma cell sample being clustered with tonsil B cell. The normal plasma cells were further subdivided into two distinct groups of tonsil plasma cells and bone marrow plasma cells. Thus, global gene expression patterns confirmed the segregation of tonsil plasma cells and bone marrow plasma cells and also allowed the distinction of tonsil B cells from both plasma cell types.

$\chi^2$ and Wilcoxon rank sum analysis were used to identify 359 and 500 genes whose mRNA expression levels were significantly altered (P<0.00005) in the tonsil B cell to tonsil plasma cell and tonsil plasma cell to bone marrow plasma cell comparison, respectively. Genes that were significantly differentially expressed in the tonsil B cell to tonsil plasma cell transition were referred as "early differentiation genes" (EDGs) and those differentially expressed in the tonsil plasma cell to bone marrow plasma cell transition were referred as "late differentiation genes" (LDGs).

Early Differentiation Genes

Of the top 50 EDGs (Table 11), most of the genes (43) were down-regulated with only 7 genes being up-regulated in this transition. Gene expression was described as being at 1 of 5 possible levels. An AAC, indicating an undetectable or absent gene transcript, was defined as "−". For all the samples in a group, expression levels were defined as "+" if the gene transcript was present and the AD was <1000, "++" for 1000≦AD<5000, "+++" for 5000≦AD<10,000, and "++++" for AD≧10,000. The largest group of EDGs encoded transcription factors. Of 16 transcription factors, only 3, XBP-1, IRF4 and BMI1, were up-regulated EDGs. Among the down-regulated transcription factors, MYC and CIITA were found. The largest family included four ets domain-containing proteins: ETS1, SPIB, SPI1, and ELF1. Other transcription factors included the repressors EED and ID3, as well as the activators RUNX3, ICSBP1, REL, ERG3, and FOXM1. It is of potential significance that as IRF4 is up-regulated in both the tonsil B cell to tonsil plasma cell and tonsil plasma cell to bone marrow plasma cell transitions, the IRF family member interferon consensus sequence binding protein, ICSBP1, which is a lymphoid-specific negative regulator, was the only gene that was expressed at a +++ level in tonsil B cells and was shut down in both tonsil plasma cells and bone marrow plasma cells. These results suggest that the removal of ICSBP1 from IRF binding sites may be an important mechanism in regulating IRF4 function.

The second most abundant class of EDGs code for proteins involved in signaling. CASP10 which is involved in the activation cascade of caspases responsible for apoptosis execution represented the only signaling protein up-regulated in tonsil plasma cells.

Three small G proteins, the Rho family members ARHG and ARHH, and the proto-oncogene HRAS were down-regulated EDGs. Two members of the tumor necrosis factor family TNF and lymphotoxin beta (LTB), as well as the TNF receptor binding protein were LDGs. Given the important role of IL-4 in triggering class-switch recombination, the observation of down-regulation (tonsil B cell to tonsil plasma cell), and eventual extinguishing (tonsil plasma cell to bone marrow plasma cell) of IL4R fits well with the differentiation states of the cells under study.

Finally, the down-regulation of the B lymphoid tyrosine kinase (BLK) whose expression is restricted to B lymphoid cells and may function in a signal transduction pathway suggests that the reduction of this kinase is important in the early stages of plasma cell differentiation. Given the important role of cell adhesion in plasma cell biology, up-regulation of ITGA6 and PECAM1 could be of particular importance. In fact, these genes also showed a continual up-regulation in the tonsil plasma cell to bone marrow plasma cell transition and represented the only extracellular adhesion genes in the EDG class. Other multiple-member classes of down-regulated EDGs included those involved in cell cycle (CCNF, CCNG2, and CDC20) or DNA repair/maintenance (TERF2, LIG1, MSH2, RPA1). The down-regulation of these genes may thus be important to inducing and/or maintaining the terminal differentiated state of the plasma cells.

Late Differentiation Genes

In the top 50 LDGs, 33 were up-regulated or turned on and 17 genes were down-regulated or turned off (Table 12). Although 16 EDGs were transcription factors, only 5 LDGs belonged to this class. The BMI1 gene, which was an up-regulated EDG, was also an LDG, indicating that the gene undergoes a significant increase in expression in both the tonsil B cell to tonsil plasma cell and tonsil plasma cell to bone marrow plasma cell transitions. BMI1 was the only up-regulated transcription factor. MYBL1, MEF2B, and BCL6 were shut down in bone marrow plasma cells and the transcription elongation factor TCEA1 was down-regulated. The largest class of LDG (n=16; 11 up- and 5 down-regulated) coded for proteins involved in signaling. The LIM containing protein with both nuclear and focal adhesion localization, FHL1; and the secreted proteins, JAG1, a ligand for Notch, insulin-like growth factor IGF1; and bone morphogenic protein BMP6 were up-regulated. The dual specific phosphatase DUSP5 and the chemokine receptor CCR2 represented genes with the most dramatically altered expression and were turned on to extremely high levels in bone marrow plasma cells while being absent in tonsil plasma cells. Additional signaling genes, including the membrane caveaolae, CAV1 and CAV2, plasma membrane proteins important in transportation of materials and organizing numerous signal transduction pathways, were up-regulated LDGs.

Given the dramatic difference in life spans of tonsil plasma cells (several days) and bone marrow plasma cells (several weeks to months), the up-regulation of the anti-apoptotic gene BCL2 (– in tonsil B cells and ++ in bone marrow plasma cells) and concomitant down-regulation of the apoptosis-inducing protein BIK (+++ in tonsil B cells and – in bone marrow plasma cells) may be critical in regulating normal programmed cell death. As in the EDGs, LDGs contained multiple adhesion-related genes, and, as in the EDGs, the LDG adhesion genes were all up-regulated.

The PECAM1 gene was found to be both an EDG and LDG, suggesting that a gradation of cell surface expression of this gene is critical in development. Whereas the integrin family member ITGA6 was an EDG, ITGA4 was found to be an LDG. The finding that ITGA4 or VLA-4 (very late antigen 4) was an LDG is consistent with published data showing that this integrin is most predominant on late stage plasma cells. The adhesion molecule selectin P ligand (SEL-PLG) which mediates high affinity, calcium-dependent binding to P-, E- and L-selectins, mediating the tethering and rolling of neutrophils and T lymphocytes on endothelial cells, may facilitate a similar mechanism in late stage plasma cells. In addition, the epithelial membrane protein 3 (EMP3), a integral membrane glycoprotein putatively involved in cell-cell interactions, was identified. LRMP (JAW1), a lymphoid-restricted, integral ER membrane protein based on strong homology to MRVI1 (IRAG) and is likely a essential nitric oxide/cGKI-dependent regulator of IP3-induced calcium release from endoplasmic reticulum stores, was found to be a down-regulated LDG. The discovery of LRMP as a down-regulated LDG is consistent with previous studies showing that, although highly expressed in lymphoid precursors, it is shut down in plasma cells.

Thus, the gene expression profiling results confirmed previous observations as well as identified novel and highly significant changes in mRNA synthesis when tonsil B cells and tonsil plasma cells and tonsil plasma cells and bone marrow plasma cells are compared.

TABLE 11

Early-Stage Differentiation Genes: Top 50 Differentially Expressed Genes In Comparison Of Tonsil B Cells And Tonsil And Bone Marrow Plasma Cells

| Accession | Symbol | Function | Quantitative Gene Expression | | |
|---|---|---|---|---|---|
| | | | TBC | TPC | BPC |
| U60519 | CASP10 | apoptosis | – | + | ++ |
| X53586 | ITGA6 | adhesion | – | + | ++ |
| U04735 | STCH | chaperone | + | ++ | ++ |
| L13689 | BMI1 | transcription; repressor; PcG | + | ++ | +++ |
| L34657 | PECAM1 | adhesion | + | ++ | +++ |
| U52682 | IRF4 | transcription; IRF family | + | +++ | +++ |
| M31627 | XBP1 | transcription; bZip family | +++ | ++++ | ++++ |
| AB000410 | OGG1 | DNA glycosylase | + | – | – |
| D87432 | SLC7A6 | solute transporter | + | – | – |
| J04101 | ETS1 | transcription; ets family | + | – | – |
| L38820 | CD1D | immunity | + | – | – |
| M28827 | CD1C | immunity | + | – | – |
| M55542 | GBP1 | signaling; GTP binding | + | – | – |
| M81182 | ABCD3 | ABC transporter | + | – | – |
| M85085 | CSTF2 | mRNA cleavage stimulating factor | + | – | – |
| U74612 | FOXM1 | transcription; fork-head family | + | – | – |
| U84720 | RAE1 | RNA export | + | – | – |
| V00574 | HRAS | signaling; GTP binding protein | + | – | – |
| X02910 | TNF | signaling; TNFα | + | – | – |
| X63741 | EGR3 | transcription; egr family | + | – | – |
| X93512 | TERF2 | telomere repeat binding protein | + | – | – |
| Z36714 | CCNF | cell cycle; cyclin F | + | – | – |
| AB000409 | MNK1 | signaling; kinase | + | – | + |
| M33308 | VCL | cytoskeleton | + | – | ++ |
| D16480 | HADHA | mitochondrial oxidation | ++ | – | – |
| M63488 | RPA1 | DNA replication/repair | ++ | – | – |
| U03911 | MSH2 | DNA repair | ++ | – | – |
| U69108 | TRAF5 | signaling; TNFR associated protein | ++ | – | – |
| X12517 | SNRPC | mRNA splicing | ++ | – | – |
| X52056 | SPI1 | transcription; ets family | ++ | – | – |
| X68149 | BLR1 | signaling; cxc receptor | ++ | – | – |
| X74301 | CIITA | transcription; adaptor | ++ | – | – |
| X75042 | REL | transcription; rel/dorsal family | ++ | – | – |
| L00058 | MYC | transcription; bHLHZip | ++ | – | ++ |
| M36067 | LIG1 | DNA ligase | ++ | + | + |
| M82882 | ELF1 | transcription; ets family | ++ | + | + |
| S76617 | BLK | signaling; kinase | ++ | + | + |
| U47414 | CCNG2 | cell cycle; cyclin G | ++ | + | + |
| U61167 | SH3D1B | unknown; SH3 containing protein | ++ | + | + |
| X61587 | ARHG | signaling; Rho G | ++ | + | + |
| Z35278 | RUNX3 | transcription; contains runt domain | ++ | + | + |

TABLE 11-continued

Early-Stage Differentiation Genes: Top 50 Differentially Expressed Genes In Comparison Of Tonsil B Cells And Tonsil And Bone Marrow Plasma Cells

| Accession | Symbol | Function | Quantitative Gene Expression | | |
|---|---|---|---|---|---|
| | | | TBC | TPC | BPC |
| M91196 | ICSBP1 | transcription; IRF family | +++ | – | – |
| M34458 | LMNB1 | cytoskeletal matrix | +++ | + | – |
| U90651 | EED | transcription; repression; PcG | +++ | + | + |
| X69111 | ID3 | transcription; repression; bHLH | +++ | + | + |
| X52425 | IL4R | signaling; cytokine receptor | +++ | ++ | – |
| Z35227 | ARHH | signaling; Rho H | +++ | ++ | + |
| U89922 | LTB | signaling; TNF-c | +++ | + | + |
| U05340 | CDC20 | cell cycle; activator of APC | ++++ | ++ | – |
| X66079 | SPIB | transcription; ets family | ++++ | ++ | – |

Accession = GENBANK ® accession number. Symbol = HUGO approved gene symbol. TBC, tonsil B cell; TPC, tonsil plasma cell; BPC, bone marrow plasma cell; AD, mean average difference; AC, absolute call. Quantitative gene expression: –, AC absent; +, AC present and AD < 1,000; ++, AD = 1,000 to 5,000; +++, AD = 5,000 to 10,000; ++++, AD > 10,000.

Accession=GENBANK® accession number.

TABLE 12

Late-Stage Differentiation Genes: Top 50 Differentially Expressed Genes In Comparison Of Tonsil And Bone Marrow Plasma Cells

| Accession | Symbol | Function | Quantitative Gene Expression | |
|---|---|---|---|---|
| | | | TPC | BPC |
| U32114 | CAV2 | signaling; membrane caveolae | – | + |
| U60115 | FHL1 | signaling; LIM domain | – | + |
| U73936 | JAG1 | signaling; Notch ligand | – | + |
| X57025 | IGF1 | signaling; growth factor | – | + |
| Z32684 | XK | membrane transport | – | + |
| D10511 | ACAT1 | metabolism; ketone | – | ++ |
| Y08999 | ARPC1A | actin polymerization | – | ++ |
| M14745 | BCL2 | signaling; anti-apoptosis | – | ++ |
| M24486 | P4HA1 | collagen synthesis | – | ++ |
| M60315 | BMP6 | signaling; TGF family | – | ++ |
| U25956 | SELPLG | adhesion | – | ++ |
| X16983 | ITGA4 | adhesion | – | ++ |
| Z18951 | CAV1 | signaling; membrane caveolae | – | ++ |
| M60092 | AMPD1 | metabolism; energy | – | +++ |
| U15932 | DUSP5 | signaling; phosphatase | – | ++++ |
| U95626 | CCR2 | signaling; chemokine receptor | – | ++++ |
| D78132 | RHEB2 | signaling; ras homolog | + | ++ |
| L41887 | SFRS7 | mRNA splicing factor | + | ++ |
| M23161 | LOC90411[a] | unknown | + | ++ |
| M37721 | PAM | metabolism; hormone amidation | + | ++ |
| M69023 | TSPAN-3[a] | unknown | + | ++ |
| U02556 | TCTE1L | dynein homolog | + | ++ |
| U41060 | LIV-1[a] | unknown | + | ++ |
| U44772 | PPT1 | lysosome enzyme | + | ++ |
| U70660 | ATOX1 | metabolism; antioxidant | + | ++ |
| X92493 | PIP5K1B | signaling; kinase | + | ++ |
| M23254 | CAPN2 | cysteine protease | + | +++ |
| J02763 | S100A6 | signaling; calcium binding | ++ | +++ |
| L13689 | BMI1 | transcription; repressor; PcG | ++ | +++ |
| L34657 | PECAM1 | adhesion | ++ | +++ |
| M23294 | HEXB | metabolism; hexoaminidase | ++ | +++ |
| M64098 | HLDBP | metabolism; sterol | ++ | ++++ |
| U52101 | EMP3 | adhesion | ++ | ++++ |
| X66087 | MYBL1 | transcription; myb-like | + | – |

TABLE 12-continued

Late-Stage Differentiation Genes: Top 50 Differentially Expressed Genes In Comparison Of Tonsil And Bone Marrow Plasma Cells

| Accession | Symbol | Function | Quantitative Gene Expression | |
|---|---|---|---|---|
| | | | TPC | BPC |
| X54942 | CKS2 | cell cycle; kinase regulator | ++ | – |
| X73568 | SYK | signaling; kinase | ++ | – |
| L08177 | EBI2 | signaling; receptor | ++ | – |
| M25629 | KLK1 | protease; serine | ++ | – |
| U00115 | BCL6 | transcription; Zn-finger | ++ | – |
| U23852 | LCK | signaling; kinase | ++ | – |
| U60975 | SORL1 | endocytosis | ++ | – |
| X63380 | MEF2B | transcription; MADs box | ++ | – |
| L25878 | EPXH1 | metabolism; epoxide hydrolase | ++ | + |
| Z35227 | ARHH | signaling; Rho C | ++ | + |
| X89986 | BIK | signaling; apoptosis | +++ | – |
| M13792 | ADA | metabolism; purine | +++ | + |
| U10485 | LRMP | ER membrane protein | +++ | + |
| M81601 | TCEA1 | transcription; elongation | +++ | ++ |
| X70326 | MACMARCK | actin binding | ++++ | + |
| X56494 | PKM2 | metabolism; energy | ++++ | + |

Accession = GENBANK ® accession number. Symbol = HUGO approved gene symbol. "Unapproved symbol. TPC, tonsil plasma cell; BPC, bone marrow plasma cell; AD, mean average difference; AC, absolute call. Quantitative gene expression: –, AC absent; +, AC present and AD < 1,000; ++, AD = 1,000 to 5,000; +++, AD = 5,000 to 10,000; ++++, AD > 10,000.

Accession=GENBANK® accession number. Symbol=HUGO approved gene symbol. [a]Unapproved symbol. TPC, tonsil plasma cell; BPC, bone marrow plasma cell; AD, mean average difference; AC, absolute call.

EXAMPLE 15

Previously Identified and Novel Genes in Plasma Cell Differentiation

In this gene expression profiling study, not only previously identified but also novel genes associated with plasma cell development were identified. Some of the genes that may be pertinent to plasma cell differentiation are discussed here.

Polyadenylation of mRNA is a complex process that requires multiple protein factors, including 3 cleavage stimulation factors (CSTF1, CSFT2 and CSTF3). It has been shown that the concentration of CSTF2 increases during B cell activation, and this is sufficient to switch IgM heavy chain mRNA expression from membrane-bound form to secreted form. The CSTF2 gene was expressed at low levels in tonsil B cells, but was turned off in tonsil and bone marrow plasma cells, indicating that CSTF2 gene expression can also be used to define plasma cell differentiation.

The gene for CD63 showed a progressive increase in gene expression across the three cell types studied. CD63 belongs to the transmembrane 4 super family (TM4SF) of membrane proteins. Expression has been found on the intracellular lysosomal membranes of hemopoietic precursors in bone marrow, macrophages, platelets, and Wiebel-Palade bodies of vascular endothelium. Importantly, CD63 was described as a maker for melanoma progression and regulates tumor cell motility, adhesion, and migration on substrates associated with P1 integrins.

Most importantly, the discovery of novel genes reported herein will lead to a broader knowledge of the molecular mechanisms involved in plasma cell differentiation. Specifically, of the top 50 EDGs, most were down-regulated, and a majority of the EDGs were transcription factors, suggesting that transcriptional regulation is an important mechanism for modulating differentiation. Among the LDGs, transcription factor representation was much lower than among the EDGs.

Cell Cycle Control and Programmed Cell Death

Consistent with the terminal differentiation of plasma cells, many genes involved in cell cycle control and DNA metabolism were down-regulated EDGs. The modulation of DNA ligase LIG1; repair enzymes MSHC, and RPA1, CDC20; and the cyclins CCNG2 and CCNF may have important consequences in inducing the quiescent state of plasma cells. The telomeric repeat binding protein TERF2, which is one of two recently cloned mammalian telomere binding protein genes, was a down-regulated EDG. TERF2 acts to protect telomer ends, prevents telomere end-to-end fusion, and may be important in maintaining genomic stability. It is of interest to determine if TERF2 is down-regulated during the terminal differentiation of all cell types, and whether the lack of this gene product in tumors of terminally differentiated cells results in the high degree of chromosome structural rearrangements which is a hallmark of multiple myeloma that lacks TERF2 gene expression (unpublished data).

The CDC28 protein kinase 2 gene CKS2, which binds to the catalytic subunit of the cyclin dependent kinases and is essential for their biological function, was the only cell cycle gene in the LDG genes. It was expressed in tonsil plasma cells that are capable of modest proliferation; however, CKS2 was completely extinguished in bone marrow plasma cells. Thus, shutting down CKS2 expression may be critical in ending the proliferative capacity of bone marrow plasma cells.

A distinguishing feature of plasma cell terminal differentiation is the acquisition of increased longevity in the bone marrow plasma cells. It is likely that this phenomenon is controlled through programmed cell death or apoptosis. The finding that anti-apoptotic and pro-apoptotic genes, BCL2 and BIK, demonstrated opposing shifts in expression is consistent with these two genes playing major roles in extending the life-span of bone marrow plasma cells.

Transcription Factors

The majority of differentially expressed genes belong to the transcription factor family. Of the 50 EDGs, only 7 were up-regulated. IRF4 and XBP1, two genes known to be up-regulated during plasma cell differentiation were in this group. Both genes were expressed at equal levels in the tonsil and bone marrow plasma cells, suggesting that a continual increase in expression of these important regulators does not occur.

Although not on the HUGENFL® (HuGenFL) Microarray, recent studies using third generation AffymetrixU95Av2 microarray have also revealed an induction of Blimp-1 (PRDM1) expression in plasma cells compared with tonsil B cells (unpublished data), confirming the expected patterns of these transcription factors.

The vast majority of EDGs were down-regulated and the single largest subgroup of EDGs represented transcription factors (13 of 43 genes). Four of the 13 transcription factors, ETS1, SPI1, SP1B, and ELF1, belong to the ets family. These results are consistent with previous studies showing that several of the ETS proteins (ETS1, ELF1, PU.1 (SPI1), and SPI-B) are expressed in the B cell lineage. It is interesting to note that the down-regulation of ETS1 in the transition between tonsil B cell to tonsil plasma cell may be an important switch, as ETS1 knock-out mice show dramatic increases in plasma cells in the spleen and peripheral blood. In addition, it is curious that although SPI1 (PU.1) interacts with IRF4 in Blimp-1$^+$ germinal center tonsil B cells and plasma cells, data presented herein show that whereas IRF4 is up-regulated in the plasma cell transition, SPI1 is shut down in tonsil and bone marrow plasma cells. Thus, these data support the notion that the ets family of transcription factors are important hematopoietically and that down-regulation of at least four family members appears to be an important event in terminal differentiation of plasma cells.

The cytoskeletal gene vinculin (VCL) and the MAP kinase-interacting serine/threonine kinase 1 gene (MKNK1) represented novel EDGs. Vinculin is thought to function in anchoring F-actin to the membrane, whereas MKNK1 is an ERK substrate that phosphorylates eIF4e after recruitment to the eIF4F complex by binding to eIF4G. These two genes were turned off in the tonsil B cell to tonsil plasma cell transition, but were reactivated in bone marrow plasma cells. The MYC proto-oncogene also showed a dramatic down-regulation in the tonsil B cell to tonsil plasma cell transition with reactivation in bone marrow plasma cells. It will be important to understand if these two genes are regulated either directly or indirectly by MYC. One of the mechanisms by which PRDF1-BF1 promotes generation of plasma cells is repression of MYC, thereby allowing the B cells to exit the cell cycle and undergo terminal differentiation. Instant study showing the extinguishing of MYC in the tonsil B cell to tonsil plasma cell transition is consistent with this data. The reactivation of MYC in bone marrow plasma cells to levels similar to those seen in tonsil B cells, which appear to be highly proliferative blasts, is unresolved but suggests that MYC may have dual roles.

Similar to the tonsil B cell to tonsil plasma cell transition, the majority of the transcription factors were down-regulated in the tonsil to bone marrow plasma cell transition. The BCL6 gene, although not in the top 50 significant EDGs, did make the top 50 list for LDGs. BCL6 did show a progressive loss of expression from tonsil B cells to tonsil plasma cells (see Table 10), but there was then a dramatic loss of expression in bone marrow plasma cells. Additional transcription factors, the myb-like gene MYBL1, and the MADS box factor MEF2B, were also turned off in bone marrow plasma cells and may be major regulators of the terminal stages of plasma cell differentiation. The transcription elongation factor TCEA1 was down-regulated but remained present. BMI1, a member of a vertebrate Polycomb complex that regulates segmental identity by repressing HOX genes throughout development, showed a significant progressive increase in expression across all groups. It is of note that BMI1 is the human homolog of the mouse Bmi-1 proto-oncogene originally discovered as cooperating with transgenic c-Myc in inducing B cell lymphomas.

Given the recognition that changes in levels of expression of transcription factors represent the most striking feature of plasma cell differentiation, it is of interest to elucidate distinct pathways of transcriptional regulation driven by the various classes of transcription factors discovered herein. This can be done with the aid of global expression profiling and sophisticated data mining tools such as Baysian networks.

EXAMPLE 16

Identification of Genes with Similar Expression between Multiple Myeloma and Cells at Different Stages of B Cell Development.

Examples 16 and 17 describe the establishment of a B cell developmental stage-based classification of multiple myeloma using global gene expression profiling.

To classify multiple myeloma with respect to EDG and LDG reported above, 74 newly diagnosed cases of multiple myeloma and 7 tonsil B cell, 7 tonsil plasma cell, and 7 bone marrow plasma cell samples were tested for variance across the 359 EDGs and 500 LDGs disclosed above. The top 50 EDGs that showed the most significant variance across all samples were defined as early differentiation genes for myeloma (EDG-MM); likewise, the top 50 LDGs showing the most significant variance across all samples were identified as late differentiation genes for myeloma-1 (LDG-MM1). Subtracting the LDG-MM1 from the 500 LDG and then applying one-way ANOVA test for variance to the remaining genes identified the top 50 genes showing similarities between bone marrow plasma cells and multiple myeloma. These genes were defined as LDG-MM2.

Within the top 50 EDG-MM (Table 13), 18 genes that showed up-regulation in the tonsil B cell to tonsil plasma cell transition showed down-regulation to levels at or below that seen in tonsil B cells. The remaining 32 EDG-MM showed a reverse profile, in that these genes were down-regulated in the tonsil B cell to plasma cell transition, but showed tonsil B cell-like expression in multiple myeloma. In Table 13, gene expression was described as being at 1 of 5 possible levels. An absent absolute call (AAC), indicating an undetectable or absent gene transcript, was defined as "−". For all the samples in a group, expression levels were defined as "+" if the gene transcript was present and the average difference (AD) was <1000, "++" for 1000≦AD<5000, "+++" for 5000≦AD<10,000, and "++++" for AD≧10,000.

One of the most striking genes defining EDG-MM was the cyclin dependent kinase 8 (CDK8), which was found absent in tonsil B cells but up-regulated to extremely high levels in tonsil and bone marrow plasma cells and then shut down again in virtually all multiple myeloma cases. The mitotic cyclin showed a progressive loss in expression from tonsil B cell (++) to tonsil plasma cell (+) to bone marrow plasma cell (−), whereas multiple myeloma cases either showing bone marrow-like levels or tonsil B cell levels. Given that the tonsil B cells used in this study likely represent highly proliferative centroblasts, multiple myeloma cases with similar levels might be suggestive of a proliferative form of the disease. A total of 27 of the top 50 EDG-MM showed no variability in multiple myeloma, ie, all multiple myeloma and tonsil B cell samples showed similar levels of expression.

A majority (34 of 50) of the top 50 LDG-MM1 (Table 14) were genes that showed up-regulation from the transition of tonsil plasma cell to bone marrow plasma cell, but showed down-regulation to tonsil plasma cell levels in multiple myeloma. The overall pattern seen for LDG-MM1 was the reverse seen for the EDG-MM, where a majority of those genes showed down-regulation from tonsil B cell to plasma cell and up regulation to tonsil B cell-like levels in multiple myeloma. The most dramatically altered LDG-MM1 was seen in the massive up-regulation of the cxc chemokines SDF1, PF4, and PPBP in bone marrow plasma cells in contrast with complete absence of detectable transcripts in all multiple myeloma. These results are validated by the fact that two separate and distinct probe sets interrogating different region of SDF1 (accession numbers L36033 and U19495) were found to show identical patterns. The RB1 tumor suppressor gene showed a significant up-regulation in the tonsil plasma cell (+) to bone marrow plasma cell (++) transition with multiple myeloma showing levels consistent with either cell type. Unlike with the EDG-MM, only 15 of the top 50 LDG-MM1 showed no variability within the multiple myeloma population.

The LDG-MM2 genes (Table 15) showing similarities between bone marrow plasma cells and subsets of multiple myeloma revealed that all genes showed variability within multiple myeloma and that the variability could be dramatic, e.g. the apoptosis inhibitor BIK. Unlike those seen in EDG-MM and LDG-MM1, a large class of LDG-MM2 represented genes coding for enzymes involved in metabolism with a majority involved in glucose metabolism.

TABLE 13

EDG-MM: Tonsil B Cell-like Multiple Myeloma Genes

| Accession | Symbol | Function | Quantitative Gene Expression | | | |
|---|---|---|---|---|---|---|
| | | | TBC | TPC | BPC | MM |
| D28364 | ANXA2 | annexin family | − | + | + | −/+ |
| U81787 | WNT10B | signaling; ligand | − | + | ++ | −/++ |
| U88898 | LOC51581[a] | unknown | − | + | + | −/+ |
| X12451 | CTSL | protease; cysteine | − | ++ | ++ | − |
| Z25347 | CDK8 | cell cycle; kinase | − | +++ + | +++ + | −/++ |
| D38548 | KIAA0076[a] | unknown | + | ++ | ++ | +/++ |
| D86479 | AEBP1 | extracellular matrix | + | ++ | ++ | + |
| U04689 | OR1D2 | signaling; receptor | + | ++ | + | + |
| M31328 | GNB3 | signaling; G protein | + | ++ | ++ | + |
| U13395 | WWOX | metabolism; oxidoreductase | + | ++ | ++ | + |
| X14675 | BCR | signaling; GTPase for RAC | + | ++ | ++ | + |
| X16665 | HOXB2 | transcription; homeobox domain | + | ++ | ++ | −/+ |
| Z11899 | POU5F1 | transcription; homeobox domain | + | ++ | ++ | + |
| Z36531 | FGL2 | secreted fibrinogen-like | + | ++ | ++ | + |
| X80907 | PIK3R2 | signaling; kinase adaptor | + | +++ | +++ | ++ |
| D31846 | AQP2 | aquaporin | ++ | +++ | +++ | ++ |
| L18983 | PTPRN | phosphatase; membrane | ++ | ++++ | ++++ | ++ |
| M23323 | CD3E | signaling; TCR partner | ++ | ++++ | ++++ | ++ |
| D83781 | KIAA0197[a] | unknown | + | − | − | + |
| HT4824 | CBS | metabolism; cystathionine-beta-synthase | + | − | − | −/++ |
| S78873 | RABIF | signaling; GTP releasing factor | + | − | − | +/++ |
| U32645 | ELF4 | transcription; ets domian | + | − | − | −/+ |
| X97630 | EMK1 | signaling; kinase; ELK domain | + | − | − | + |
| Z24724 | UN-KNOWN[a] | cell cycle | + | − | − | +/++ |

TABLE 13-continued

EDG-MM: Tonsil B Cell-like Multiple Myeloma Genes

| Accession | Symbol | Function | TBC | TPC | BPC | MM |
|---|---|---|---|---|---|---|
| D16480 | HADHA | mitochondrial oxidation | ++ | – | – | –/++ |
| L77701 | COX17 | mitochondrial oxidation | ++ | – | – | –/++ |
| M90356 | BTF3L2 | transcription; NAC domain | ++ | – | – | ++ |
| U08815 | SF3A3 | spliceosome | ++ | – | – | +/++ |
| U53225 | SNX1 | intracellular trafficking | ++ | – | – | +/++ |
| M25753 | CCNB1 | cell cycle | ++ | + | – | –/++ |
| D87448 | TOPBP1[a] | topoisomerase II binding protein | ++ | + | + | +/++ |
| L38810 | PSMC5 | 26S proteasome subunit 5 | ++ | + | + | ++ |
| M29551 | PPP3CB | signaling; calcium dependent pho | ++ | + | + | +/++ |
| M32886 | SRI | signaling; calcium binding | ++ | + | + | ++ |
| U24704 | PSMD4 | 26S proteasome subunit 4 | ++ | + | + | ++ |
| U25165 | FXR1 | RNA binding protein | ++ | + | + | ++ |
| U37022 | CDK4 | cell cycle; kinase | ++ | + | + | ++ |
| U53003 | C21orf33 | unknown; highly conserved | ++ | + | + | ++ |
| X89985 | BCL7B | actin cross-linking | ++ | + | + | ++ |
| D49738 | CKAP1 | tubulin folding | +++ | + | + | ++ |
| D43950 | CCT5 | chaperonin | +++ | ++ | ++ | +++ |
| D82348 | ATIC | metabolism; purine biosynthesis | +++ | ++ | ++ | +++ |
| D86550 | DYRK1A | signaling; kinase | +++ | ++ | ++ | +++ |
| L06132 | VDAC1 | anion channel | +++ | ++ | ++ | ++/+++ |
| L43631 | SAFB | nuclear scaffold factor | +++ | ++ | ++ | ++/+++ |
| M30448 | CSNK2B | signaling; casein kinase regulation | +++ | ++ | ++ | ++/+++ |
| X76013 | QARS | metabolism; glutaminyl tRNA synthetase | +++ | ++ | ++ | ++/+++ |
| D83735 | CNN2 | actin binding | ++++ | ++ | ++ | ++/+++ |
| M86667 | NAP1L1 | nucleosome assembly | +++ | ++ | ++ | +++ |
| X04828 | GNAI2 | signaling; G protein | ++++ | ++ | ++ | ++/+++ |

Genes identified by one-way ANOVA analysis. Accession = GENBANK® accession number. Symbol = HUGO approved gene symbol; unapproved symbol marked by [a]. TBC, tonsil B cells; TPC, tonsil plasma cells; BPC, bone marrow plasma cells; AC, absolute call; AD, average difference. Quantitative gene expression: –, AC absent; +, AC present and AD < 1,000; ++, AD = 1,000 to 5,000; +++, AD = 5,000 to 10,000; ++++, AD > 10,000.

Genes identified by one-way ANOVA analysis. Accession=GENBANK® accession number.

TABLE 14

LDG-MM1: Tonsil Plasma Cell-Like Multiple Myeloma Genes

| Accession | Symbol | Function | TPC | BPC | MM |
|---|---|---|---|---|---|
| U90902 | 23612[a] | unknown; related to TIAM1 | – | + | –/++ |
| D12775 | AMPD3 | metabolism; AMP deaminase | – | + | –/++ |
| U37546 | BIRC3 | signaling; anti-apoptosis | – | ++ | –/++ |
| Z11793 | SEPP1 | metabolism; selenium transport | – | +++ | –/+ |
| L36033 | SDF1 | signaling; cxc chemokine | – | +++ | – |
| U19495 | SDF1 | signaling; cxc chemokine | – | +++ | – |
| M27891 | CST3 | protease inhibitor | – | ++++ | –/++++ |
| M26602 | DEFA1 | immunity | – | ++++ | –/++++ |
| M25897 | PF4 | signaling; cxc chemokine | – | ++++ | – |
| M54995 | PPBP | signaling; cxc chemokine | – | ++++ | – |
| U79288 | KIAA0513[a] | unknown | + | ++ | +/++ |
| M59465 | TNFAIP1 | signaling; anti-apoptosis | + | ++ | +/++++ |
| X53586 | ITGA6 | adhesion | + | ++ | +/++ |
| D50663 | TCTEL1 | dynein light chain | + | ++ | +/++ |
| U40846 | NAGLU | metabolism; hepran sulfate degradation | + | ++ | +/++ |
| M80563 | S100A4 | Signaling; calcium binding | + | ++ | +/++++ |
| X04085 | CAT | metabolism; catalase | + | ++ | +/++ |
| L02648 | TCN2 | metabolism; vitamin B12 transport | + | ++ | + |
| L35249 | ATP6B2 | lysosome; vacuolar proton pump | + | ++ | + |
| L09209 | APLP2 | amyloid beta precursor like | + | ++ | + |
| L41870 | RB1 | cell cycle | + | ++ | +/++ |
| X76732 | NUCB2 | signaling; calcium binding | + | +++ | +/+++ |
| D29805 | 5B4GALT1 | adhesion | + | +++ | + |
| M29877 | FUCA1 | lysosome; fucosidase | + | +++ | +/++ |
| M32304 | TIMP2 | metalloproteinase 2 inhibitor | + | +++ | +/++++ |
| D10522 | MACS | actin crosslinking | + | ++++ | –/++ |
| L38696 | RALY[a] | RNA binding | ++ | +++ | ++ |
| U05875 | IFNGR2 | signaling; interferon gamma receptor | ++ | +++ | ++/+++ |
| U78095 | SPINT2 | protease inhibitor; blocks HGF | ++ | +++ | –/+++ |
| L13977 | PRCP | lysosomal; angiotensinase C | ++ | ++++ | ++ |
| U12255 | FCGRT | IgG Fc receptor | ++ | ++++ | –/+++ |
| L06797 | CXCR4 | signaling; SDF1 receptor | ++ | ++++ | ++/++++ |
| D82061 | FABGL | metabolism | ++ | ++++ | ++/+++ |
| Y00433 | GPX1 | oxidation protection | +++ | ++++ | ++/+++ |
| M60752 | H2AFA | histone; nucleosome | + | – | –/++ |
| U18300 | DDB2 | DNA repair | + | – | + |
| X63692 | DNMT1 | DNA methyl-transferase | + | – | + |
| D11327 | PTPN7 | signaling; phosphatase | ++ | – | ++ |
| X54942 | CKS2 | cell cycle; kinase regulator | ++ | – | +/+++ |
| D14874 | ADM | adrenomedullin | ++ | + | +/++++ |
| D86976 | KIAA0223[a] | minor histocompatability antigen | ++ | + | +/+++ |
| X52979 | SNRPB | mRNA splicing | ++ | + | +/++ |
| Z49254 | MRPL23 | mitochondrial ribosomal protein | ++ | + | ++ |

TABLE 14-continued

LDG-MM1: Tonsil Plasma Cell-Like Multiple Myeloma Genes

| Accession | Symbol | Function | Quantitative Gene Expression | | |
|---|---|---|---|---|---|
| | | | TPC | BPC | MM |
| U66464 | HPK1 | signaling; kinase | ++ | + | +/++ |
| U91903 | FRZB | signaling; WNT antagonists | ++ | + | +/++ |
| D87453 | MRPS27 | mitochondrial ribosomal protein | ++ | + | +/++ |
| X59932 | CSK | signaling; kinase | +++ | ++ | ++ |
| L17131 | HMGIY | transcription; high mobility group | ++++ | + | ++/++++ |
| L19779 | H2AFO | histone; nucleosome | ++++ | ++ | ++++ |
| U70439 | SSP29[a] | unknown | ++++ | +++ | +++/++++ |

Genes identified by one-way ANOVA analysis. Accession = GENBANK® accession number. Symbol = HUGO approved gene symbol; unapproved symbol marked by [a]. TPC, tonsil plasma cells; BPC, bone marrow plasma cells; AC, absolute call; AD, average difference. Quantitative gene expression: −, AC absent; +, AC present and AD < 1,000; ++, AD = 1,000 to 5,000; +++, AD = 5,000 to 10,000; ++++, AD > 10,000.

Genes identified by one-way ANOVA analysis. Accession=GENBANK® accession number.

TABLE 15

LDG-MM2: Bone marrow Plasma Cell-like Multiple Myeloma Genes

| Accession | Symbol | Function | Quantitative Gene Expression | |
|---|---|---|---|---|
| | | | BPC | MM |
| U61145 | EZH2 | transcription; SET domain | − | −/+ |
| HT4000 | SYK | signaling; lymphocyte kinase | − | −/++ |
| X89986 | BIK | signaling; apoptosis inducer | − | −/++++ |
| D85181 | SC5DL | metabolism; sterol-C5-desaturase | + | −/+ |
| M98045 | FPGS | metabolism; folylpolyglutamate synthase | + | −/++ |
| L41559 | PCBD | transcription; enhances TCF1 activity | + | −/++ |
| L25876 | CDKN2 | cell cycle; CDK inhibitor; phosphatase | + | +/++ |
| U76638 | BRAD1 | transcription; BRCA1 heterodimer | + | +/++ |
| L05072 | IRF1 | transcription; IRF family | + | +/++ |
| D87440 | KIAA025[a] | unknown | + | +/++ |
| U02680 | PTK9 | tyrosine kinase | + | +/++ |
| U28042 | DDX10 | oncogene; ATP-dependent RNA helicase | + | +/++ |
| L20320 | CDK7 | cell cycle; kinase | + | +/++ |
| X56494 | PKM2 | metabolism; pyruvate kinase | + | +/++++ |
| M12959 | TCRA | signaling; T cell receptor | ++ | −/++ |
| HT3981 | INSL3 | signaling; insulin-like peptide; IGF family | ++ | −/++ |
| U21931 | FBP1 | metabolism; fructose bisphophatase | ++ | −/++++ |
| Z48054 | PXR1 | metabolism; peroxisome biogenesis | ++ | +/++ |
| D84145 | WS-3[a] | dynatin 6 | ++ | +/++ |
| D14661 | KIAA0105[a] | transcription; WT1-associating protein | ++ | +/++ |
| X77548 | NCOA4 | transcription; nuclear receptor coactivator | ++ | +/++ |
| M90696 | CTSS | cysteine protease | ++ | +/++ |
| D11086 | IL2RG | cytokine receptor | ++ | +/++ |
| U70426 | RGS16 | signaling; GTPase activating protein | ++ | +/+++ |
| X14850 | H2AX | histone; required for antibody maturation | ++ | +/+++ |
| M29927 | OAT | metabolism; ornithine aminotransferase | ++ | +/+++ |
| S74017 | NFE2L2 | transcription; | ++ | +/+++ |
| HT4604 | GYG | metabolism; glycogen biogenesis | ++ | +/+++ |
| M55531 | SLC2A5 | metabolism; fructose transporter | ++ | +/++++ |
| M60750 | H2BFL | histone; nucleosome | ++ | +/++++ |
| L19437 | TALDO1 | metabolism; transaldolase | ++ | ++/+++ |
| M10901 | NR3C1 | transcription; glucocorticoid receptor | ++ | ++/+++ |
| L41887 | SFRS7 | MRNA splicing factor | ++ | ++/+++ |
| M34423 | GLB1 | metabolism; galactosidase | ++ | ++/++++ |
| X15414 | AKR1B1 | metabolism; aldose reductase | +++ | +/++++ |
| J04456 | LGALS1 | signaling; inhibits CD45 phosphatase | +++ | +/++++ |
| X92493 | PIP5K1B | signaling; kinase | +++ | +/++++ |
| U51478 | ATP1B3 | Na+, K+ transporter | +++ | ++/++++ |
| X91257 | SARS | seryl-tRNA synthetase | +++ | ++/++++ |
| D30655 | EIF4A2 | translation initiation | +++ | ++/++++ |
| D31887 | KIAA0062[a] | unknown | +++ | ++/++++ |
| X04106 | CAPN4 | cysteine protease; calcium dependent | +++ | ++/++++ |
| D87442 | NCSTN[a] | nicastrin | +++ | ++/++++ |
| L76191 | IRAK1 | signaling; cytokine receptor kinase | +++ | +++/++++ |
| HT1428 | HBB | hemoglobin | ++++ | −/++++ |
| U44975 | COPEB | oncogene; transcription factor | ++++ | −/++++ |
| X55733 | EIF4B | translation initiation | ++++ | +/++++ |
| L09604 | PLP2 | signaling; colonic epithelium differentiation | ++++ | +/++++ |
| HT1614 | PPP1CA | signaling; phosphatase | ++++ | +++/++++ |
| L26247 | SUI1[a] | translation initiation; probable | ++++ | +++/++++ |

Accession = GENBANK® accession number or TIGR database. Symbol = HUGO approved gene symbol; unapproved symbol marked by [a]. BPC, bone marrow plasma cells; AC, absolute call; AD, average difference. Quantitative gene expression: −, AC absent; +, AC present and AD < 1,000; ++, AD = 1,000 to 5,000; +++, AD = 5,000 to 10,000; ++++, AD > 10,000.

Accession=GENBANK® accession number or TIGR database.

EXAMPLE 17

Hierachical Cluster Analysis with EDG-MM, LDG-MM1, and LDG-MM2 Reveals Developmental Stage-Based Classification of Multiple Myeloma To identify whether variability in gene expression seen in multiple myeloma (MM) might be used to discern subgroups of disease, hierarchical cluster analysis was performed on 74 newly diagnosed MM, 7 tonsil B cell, 7 tonsil plasma cell, and 7 bone marrow samples using the EDG-MM (FIG. 12), LDG-MM1 (FIG. 13), and LDG-MM2 (FIG. 14). Hierarchical clustering was applied to all samples using 30 of the 50 EDG-MM. A total of 20 genes were filtered out with Max−Min<2.5. This filtering was performed on this group because many of the top 50 EDG-MM showed no variability across MM and thus could not be used to distinguish MM subgroups. A similar clustering strategy was employed to cluster the samples using the 50 LDG-MM1 and 50 LDG-MM2.

The MM samples clustering with the tonsil B cell samples were then identified to determine whether the MM cases clustering with tonsil B cells, or tonsil and bone marrow plasma cells could be correlated with gene expression-defined MM subgroups (Table 16). This data showed that of the MM cases clustering tightly with the tonsil B cell samples, 13 of 22 were from the MM4 subgroup, accounting for a majority of all MM4 cases (13 of 18 MM4 samples). The LDG-MM defined cluster distribution of gene expression-defined M M subgroups was dramatically different in that 14 of the 28 MM samples clustering with the tonsil plasma cell samples were from MM3 subgroup (14 of 15 MM3 samples). LDG-MM2 again showed a strong correlation with the MM subgroups in that 14 of the 20 MM cases in this cluster were from the MM2 subgroup (14 of 21 MM2 cases). Thus, the MM4, MM3, and MM2 subtypes of MM have similarities to tonsil B cells, tonsil plasma cells, and bone marrow plasma cells respectively. MM1 represented the only subgroup with no strong correlations with normal cell counterparts tested here, suggesting that this class has unique characteristics yet to be uncovered.

The distribution of the four MM subgroups in the normal cell cluster groups was determined next (Table 17). The results demonstrate that whereas all MM3 cases were able to be classified, 6 MM1, 5 MM2, and 3 MM4 cases were not clustered with any normal cell group in any of the three cluster analyses. In all samples capable of being clustered, there were strong correlations between gene expression-defined subgroups and normal cell types with the exception of MM1. The data also show that 3 MM1, 2 MM2, 4 MM3, and 1 MM4 cases were found to cluster in two groups. No samples were found in three groups and all cases clustering with two normal classes were always in an adjacent, temporally appropriate groups. P241 was an exception in that it was clustered in the bone marrow plasma cell and tonsil B cell groups.

Because one of the EDG-MMs was discovered to be cyclin B1 (CCNB1) (Table 13), it was determined if a panel of proliferation association genes recently discovered to be up-regulated in MM4 could be used to advance and validate the classification of MM4 as a so-called tonsil B cell-like form of MM. Box plots of the expression patterns of CCNB1, CKS1, CKS2, SNRPC, EZH2, KNSL1, PRKDC, and PRIM1 showed significant differences across all the groups tested with strong significant correlation between tonsil B cells and MM4 (FIG. 15). Several important observations were made in this analysis. For all the genes, with the exception of SNRPC, there was a progressive reduction in expression in the transition from tonsil B cells to tonsil plasma cells to bone marrow plasma cells. In addition, striking correlations were observed with PRIM1 (FIG. 15). Although PRIM1 expression was significantly different across the entire group ($P=4.25\times10^{-5}$), no difference exists between tonsil B cells and MM4 (Wilcoxon rank sum [WRS] P=0.1), or between tonsil plasma cells and MM3 (WRS P=0.6). Given the important function of several transcription factors in driving and/or maintaining plasma cell differentiation, it was determined if these factors showed altered expression across the groups under study. Although other factors showed no significant changes, XBP1 (FIG. 15) showed an enormous up-regulation between tonsil B cells and tonsil plasma cells as expected. However, the gene showed a reduction in bone marrow plasma cells and a progressive loss across the four MM subgroups with MM4 showing the lowest level ($P=3.85\times10^{-10}$).

Based on conventional morphological features, plasma cells have been thought to represent a homogeneous end-stage cell type. However, phenotypic analysis and gene expression profiling disclosed herein demonstrated that plasma cells isolated from distinct organs can be recognized as belonging to distinct stages of development. Multiple myeloma plasma cells are derived from the bone marrow and are thought to represent a transformed counterpart of normal terminally differentiated bone marrow plasma cells. However, the dramatic differences in survival, which can range from several months to greater than 10 years, suggests that multiple myeloma may represent a constellation of several subtypes of disease. Conventional laboratory parameters have not been particular useful in segregating distinct disease subtypes with sufficient robustness that would allow adequate risk stratification. In addition, unlike achievements in classifying leukemias and lymphomas based on similar nonrandom recurrent chromosomal translocations, the extreme karyotypic heterogeneity of multiple myeloma has made attempts at understanding the molecular mechanisms of the disease and classification prediction virtually impossible.

In studies presented here, it was identified that many EDGs and LDGs exhibit highly variable expression in multiple myeloma, suggesting that multiple myeloma might be amenable to a developmental stage-based classification. It appears from the results of this study that multiple myeloma can in fact be classified based on similarities in gene expression with cells representing distinct stages of B cell differentiation. This developmental based-system in conjunction with the gene expression-based system reported above represents a critical affirmation of the validity of the developmental-based system.

Recent studies provide support for the hypothesis that MM3 represents a tonsil plasma cell-like form of the disease. Microarray profiling with the U95Av2 GENECHIP® (Gene Chip) on 150 newly diagnosed patients (including the 74 described here) along with an analysis of chromosome 13 loss has revealed a significant link between reduced RB1 transcripts with either monosomy or partial deletions of chromosome 13 (unpublished data). In these studies, it was observed that a number of multiple myeloma cases with or without chromosome 13 deletion had RB1 transcripts at levels comparable to those seen in normal tonsil plasma cells. FISH analysis with a bacterial artificial chromosome BAC covering RB1 demonstrated that these cases did not have interstitial deletions of the RB1 locus. Given that RB1 was found to be a LDG-MM 1, it was determined if the low levels of RB1 may be linked to tonsil plasma cell-like MM, i.e MM3. Of 35 multiple myeloma cases with RB1 AD values of <1100 (RB1 AD value not less than 1100 in 35 normal bone marrow plasma cell samples tested), 74% belonged to the MM3 class. In contrast, of 38 multiple myeloma cases lacking deletion 13 and having RB1 AD values greater than 1100, only 21% belonged to the MM3 subtype (unpublished data).

Although there is a significant link between the cell development-based classification and gene expression profiling-based classification disclosed herein, there are exceptions in that although as expected the majority of the MM4 cases belonged to the tonsil B cell-cluster subgroup, 5 MM3, 1 MM2, and 3 MM1 cases were also found in this cluster. The recognition that cases within one gene expression-defined subgroup could be classified in two normal cell defined clusters suggests these cases may have intermediate characteristics with distinct clinical outcomes. It is of interest to determine if the unsupervised gene expression-based system or developmental stage-based system alone or in combination will allow the creation of robust risk stratification system. This can be tested by allowing sufficient follow-up time on >150 uniformly treated multiple myeloma cases in which profiling has been performed at diagnosis.

MM1 was the only gene expression-defined subgroup lacking strong similarities to any of the normal cell types analyzed in this study. It is possible that MM1 has similarities to either mucosal-derived plasma cells or peripheral blood plasma cells which has recently been shown to represent a distinct type of plasma cells. Future studies will be aimed at providing a developmental stage position for this subtype.

The hypoproliferative nature of multiple myeloma, with labeling indexes in the clonal plasma cells rarely exceeding 1%, has lead to the hypothesis that multiple myeloma is a tumor arising from a transformed and proliferative precursor cell that differentiates to terminally differentiated plasma cells. It has been shown that there is a bone marrow B cell population transcribing multiple myeloma plasma cell-derived VDJ joined to IgM sequence in IgG- and IgA-secreting multiple myelomas. Other investigations have shown that the clonogenic cell in multiple myeloma originates from a pre-switched but somatically mutated B cell that lacks intraclonal variation. This hypothesis is supported by recent use of single-cell and in situ reverse transcriptase-polymerase chain reaction to detect a high frequency of circulating B cells that share clonotypic Ig heavy-chain VDJ rearrangements with multiple myeloma plasma cells. Studies have also implicated these precursor cells in mediating spread of disease and affecting patient survival.

Links of gene expression patterns between subsets of multiple myeloma and cells representing different late stages of B cell differentiation further support the above hypothesis in that MM4 and MM3 may have origins in a so called "multiple myeloma stem cell". This hypothesis can be tested by isolating B cells from tonsils or lymph nodes or peripheral blood of MM3 and MM4 patients, differentiating them into plasma cells in vitro using a new method described by Tarte et al. (2002) and then testing for the presence of an multiple myeloma gene expression signature within the differentiated populations. Even if the multiple myeloma stem cell represents a minority population in the B cells, the multiple myeloma gene expression signature may be recognized, if not with conventional microarray, then by more sensitive quantitative real-time RT-PCR. A real time RT-PCR method is envisioned as expression profile models using at little as 20 genes that distinguish malignant multiple myeloma plasma cells from normal plasma cells at an accuracy of 99.5% have been developed (unpublished data).

Regardless of the outcome of these experiments, it is clear that gene expression profiling has become an extremely powerful tool in evaluating the molecular mechanisms of plasma cell differentiation and how these events relate to multiple myeloma development and progression, which in turn should provide more rational means of treating this currently fatal disease.

TABLE 16

Distribution of Multiple Myeloma Subgroups in Hierarchical Clusters Defined by EDG-MM, LDG-MM1, and LDG-MM2 Genes

| Normal Cell-Defined Cluster | Gene Expression-Defined MM Subgroups | | | | |
|---|---|---|---|---|---|
| | MM1 (n = 20) | MM2 (n = 21) | MM3 (n = 15) | MM4 (n = 18) | P |
| EDG-MM (n = 22) | 3 | 1 | 5 | 13 | .00005 |
| LDG-MM1 (n = 29) | 8 | 4 | 14 | 3 | .000008 |
| LDG-MM2 (n = 20) | 6 | 14 | 0 | 0 | .000001 |

TABLE 17

Distribution of Gene Expression-Defined Multiple Myeloma Subgroup Cases in Normal Cell Clusters defined by EDG-MM, LDG-MM1, and LDG-MM2

| MM1 | TBC | TPC | BPC | MM2 | TBC | TPC | BPC | MM3 | TBC | TPC | BPC | MM4 | TBC | TPC | BPC |
|---|---|---|---|---|---|---|---|---|---|---|---|---|---|---|---|
| P026 | | Y | Y | P237 | | Y | Y | P052 | Y | Y | | P034 | Y | Y | |
| P037 | | Y | Y | P241 | Y | | Y | P098 | Y | Y | | P051 | Y | | |
| P029 | Y | Y | | P079 | | | Y | P107 | Y | Y | | P057 | Y | | |
| P061 | | Y | | P083 | | | Y | P158 | Y | Y | | P063 | Y | | |
| P066 | | Y | | P121 | | | Y | P119 | | Y | | P065 | Y | | |
| P006 | | Y | | P144 | | | Y | P221 | | Y | | P075 | Y | | |
| P120 | | Y | | P157 | | | Y | P030 | | Y | | P084 | Y | | |
| P131 | | Y | | P171 | | | Y | P043 | | Y | | P122 | Y | | |
| P002 | | | Y | P176 | | | Y | P053 | | Y | | P127 | Y | | |
| P010 | | | Y | P213 | | | Y | P055 | | Y | | P154 | Y | | |
| P067 | | | Y | P215 | | | Y | P138 | | Y | | P187 | Y | | |
| P226 | | | Y | P251 | | | Y | P155 | | Y | | P199 | Y | | |
| P025 | Y | | | P250 | | | Y | P163 | | Y | | P255 | Y | | |
| P082 | Y | | | P222 | Y | | | P239 | | Y | | P054 | | Y | |
| *P085* | | | | P103 | Y | | | P175 | Y | | | P101 | | Y | |
| *P099* | | | | P202 | Y | | | | | | | P056 | | | |
| *P001* | | | | P015 | | | | | | | | *P091* | | | |
| *P016* | | | | P048 | | | | | | | | *P168* | | | |

TABLE 17-continued

Distribution of Gene Expression-Defined Multiple Myeloma Subgroup Cases in Normal Cell Clusters defined by EDG-MM, LDG-MM1, and LDG-MM2

| MM1 | TBC | TPC | BPC | MM2 | TBC | TPC | BPC | MM3 | TBC | TPC | BPC | MM4 | TBC | TPC | BPC |
|---|---|---|---|---|---|---|---|---|---|---|---|---|---|---|---|
| *P036* | | | | *P124* | | | | | | | | | | | |
| *P118* | | | | *P212* | | | | | | | | | | | |
| | | | | *P249* | | | | | | | | | | | |

MM1, MM2, MM3, MM4, and PXXX represent gene expression-defined subgroups and patient identifiers, respectively. Y indicates that the case was found in the normal cell-defined cluster. Cases in italics were not found to cluster with any normal cell type. Some cases were found to cluster with two normal cell types. TBC, tonsil B cells; TPB, tonsil plasma cells; BPC, bone marrow plasma cells.

EXAMPLE 18

Diagnostic Models that Distinguish Multiple Myeloma, Monoclonal Gammopathy of Undetermined Significance, and Normal Plasma Cells The molecular mechanisms of the related plasma cell dyscrasias monoclonal gammopathy of undetermined significance (MGUS) and multiple myeloma (MM) are poorly understood. Additionally, the ability to differentiate these two disorders can be difficult. This has important clinical implications because MGUS is a benign plasma cell hyperplasia whereas MM is a uniformly fatal malignancy. Monoclonal gammopathies are characterized by the detection of a monoclonal immunoglobulin in the serum or urine and underlying proliferation of a plasma cell/B lymphoid clone. Patients with MGUS have the least advanced disease and are characterized by a detectable plasma cell population in the marrow (<10%) and secretion of a monoclonal protein detectable in the serum (<30 g/L), but they lack clinical features of overt malignancy (such as lytic bone lesions, anemia, or hypercalcemia). Patients with overt MM have increased marrow plasmacytosis (>10%), serum M protein (>30 g/L), and generally present with anemia, lytic bone disease, hypercalcemia, or renal insufficiency.

Approximately 2% of all monoclonal gammopathy of undetermined significance cases will convert to overt multiple myeloma per year, but it is virtually impossible to predict which of these cases will convert. A difficulty in the clinical management of multiple myeloma is the extreme heterogeneity in survival, which can range from as little as two months to greater than eight years with only 20% of this variability being accounted for with current clinical laboratory tests. Thus, there is a great need for more robust methods of classification and stratification of these diseases.

This example reports on the application of a panel of statistical and data mining methodologies to classify multiple myeloma (MM), monoclonal gammopathy of undetermined significance (MGUS), and normal plasma cells. Expressions of 12,000 genes in highly purified plasma cells were analyzed on a high density oligonucleotide microarray. Various methodologies applied to global gene expression data identified a class of genes whose altered expression is capable of discriminating normal and malignant plasma cells as well as classifying some MGUS as "like" MM and others as "unlike" MM. The extremely high predictive power of this small subset of genes, whose products are involved in a variety of cellular processes, e.g., adhesion and signaling, suggests that their deregulated expression may not only prove useful in the creation of molecular diagnostics, but may also provide important insight into the mechanisms of MM development and/or conversion from the benign condition of MGUS to the overly malignant and uniformly fatal MM.

Six different methodologies were employed herein: logistic regression, decision trees, support vector machines (SVM), Ensemble of Voters with 20 best information gain genes (EOV), naïve Bayes, and Bayesian networks. All six models were run on microarray data derived from Affymetrix (version 5) high density oligonucleotide microarray analysis. One hundred fifty six untreated MM samples, 34 healthy samples, and 32 samples designated as MGUS were compared. The normalization algorithm available from the Affymetrix software was used. Information on normalization and standardization of the microarray data is available on Affymetrix's website.

Statistical and Data Mining Methodologies

Various methods were employed with two goals in mind. The first goal is to identify genes whose over or under expression are apparent in the comparison of healthy samples, MGUS (monoclonal gammopathy of undetermined significance) samples, and malignant MM (multiple myeloma) samples. The second goal is to identify optimal methods for use in analyzing microarray data and specifically methods applicable to analyzing microarray data on samples from MGUS and MM patients. Previous work has been done in identifying lists of genes that discriminate between the two types of samples (Zhan et. al., 2002a; Chauhan et. al., 2002), but, to our knowledge, this is the first work that has been done on simultaneously identifying discriminatory genes and creating models to predict and describe the differences between myeloma, MGUS, and healthy samples.

For each of the methods (and each of the comparisons), a 10-fold cross validation was employed to estimate the prediction error. Using 10-fold cross validation, $1/10^{th}$ of the data was removed (the 'test' data), and the entire model was created using only the remaining 90% of the data (the 'training' data.) The test data were then run through the training model and any misclassifications were noted. Error rates were computed by compiling the misclassifications from each of the 10 independent runs. Empirical results suggest that 10-fold cross validation may provide better accuracy estimates than the more common leave one out cross validation (Kohavi, 1995).

Logistic Regression

The logistic procedure creates a linear model that yields a number between zero and one. This value represents a predictive probability, for example, of being in the multiple myeloma sample (predictive value close to one) or of being in the normal sample (predictive value close to zero). The structure allows for knowledge of the uncertainty in predicting the group membership of future samples. For example, a new sample might be classified with a predictive probability of 0.53 and classified as multiple myeloma, albeit with much less confidence than another sample whose predictive probability is 0.99.

Decision Trees

Decision tree induction algorithms begin by finding the single feature that is most correlated with class. For the present discussion, mutual information was used and the classes were multiple myeloma vs. normal, multiple myeloma vs. MGUS and MGUS vs. normal. For each feature, the algorithm computes the information gain of the detection and of the optimal split point for the real-valued measure (signal). Information gain is defined as follows: the entropy of a data set is—p $\log_2 p$—$(1-p)\log_2(1-p)$ where p is the fraction of samples that are of a certain class. A split takes one data set and divides it into two data sets: the set of data points for which the feature has a value below the split point (or a particular nominal value) and the set of data points for which the gene has a value above the split point (or any other nominal value).

Ensembles

Even with pruning, decision trees can sometimes over fit the data. One approach to avoid over fitting is to learn the n best simple decision trees, and let these trees vote on each new case to be predicted. The simplest decision tree is a decision stump, a decision tree with a single internal node, or decision node. Our "Ensemble of Voters" (EOV) approach is an unweighted majority vote of the top 20 decision stumps, scored by information gain.

Naïve Bayes

Naïve Bayes is so named because it makes the (often) naïve assumption that all features (e.g. gene expression levels) are conditionally independent of the given class value (e.g. MM or normal). In spite of this naive assumption, in practice it often works very well. Like logistic regression, naïve Bayes returns a probability distribution over the class values. The model simply takes the form of Bayes' rule with the naïve conditional independence assumption.

Bayesian Networks

Bayesian networks (Bayes nets) are a very different form of graphical model from decision trees. Like decision trees, the nodes in a Bayes net correspond to features, or variables. For classification tasks, one node also corresponds to the class variable. A Bayes net is a directed acyclic graph (DAG) that specifies a joint probability distribution over its variables. Arcs between nodes specify dependencies among variables, while the absence of arcs can be used to infer conditional independencies. By capturing conditional independence where it exists, a Bayes net can provide a much more compact representation of the joint distribution than a full joint table or other representation. There is much current research into the development of algorithms to construct Bayes net models from data (Friedman et al., 1999; Murphy, 2001; Pe'er et al., 2001.) Bayes nets are proven to be outstanding tools for classification. For example, in KDD Cup 2001, an international data mining competition with over 100 entries, the Bayes net learning algorithm Power-Predictor was the top performer on a data set with strong similarities to microarray data (Cheng et al., 2000). This is the algorithm employed in the present study.

Support Vector Machines

Support vector machines (SVMs) (Vapnik, 1998; Cristianini and Shawe-Taylor, 2000) are another novel data mining approach that has proven to be well suited to gene expression microarray data (Brown et al., 1999; Furey et al., 2000.) At its simplest level, a support vector machine is an algorithm that attempts to find a linear separator between the data points of two classes. SVMs seek to maximize the margin, or separation between the two classes. Maximizing the margin can be viewed as an optimization task that can be solved with linear programming techniques. Support vector machines based on "kernel methods" can efficiently identify separators that belong to other functional classes. A commonly used kernel is the Gaussian kernel. Nevertheless, for gene expression microarray data, it has been repeatedly demonstrated empirically that simple linear SVMs give better performance (Brown et al., 1999; Furey et al., 2000) than SVMs with other kernels.

Results

As mentioned, each model was tested using 10-fold cross validation to obtain error (misclassification) rates. For each of 10 runs of the data, 10% of the sample was removed and the prediction model was created. Then, using the created model, the test sample was predicted into groups and the accuracy was recorded. After completing all 10 runs, the accuracy values were accumulated into the following table (Table 18).

TABLE 18

Ten-Fold Cross Validation Results

| % correctly classified | MM | Normal | MM | MGUS | MGUS | Normal |
| --- | --- | --- | --- | --- | --- | --- |
| Logistic | 98.72% | 91.18% | 89.1% | 18.8% | 90.63% | 97.06% |
| Trees | 97.44% | 94.12% | 87.18% | 37.5% | 90.63% | 94.12% |
| SVM | 98.72% | 97.06% | 89.10% | 34.38% | 90.63% | 100% |
| Bayes Net | 98.72% | 100% | 93.56% | 34.38% | 90.63% | 97.06% |
| EOV | 98.08% | 100% | 57.69% | 68.75% | 90.63% | 100% |
| Naïve Bayes | 98.08% | 100% | 91.67% | 43.75% | 90.63% | 100% |

There does not appear to be one methodology that stands out from the rest in terms of predicting group membership. In the difficult classification of multiple myeloma (MM) vs. MGUS, Ensemble of Voters classifies the most MGUS correctly (68.75%), but the fewest multiple myeloma correctly (57.69%.) Using naïve Bayes produces the best classification, though it does not seem to be appreciably better than the other methods. All the methods appear to be able to classify multiple myeloma vs. Normal quite well and MGUS vs. Normal almost as well.

To test the difference of accuracy across procedures, a paired t-test was done for the overall correct classification rate for each of the comparisons on each of the folds of the procedures. None of the methods were significantly different ($p \leq 0.05$) except the EOV when compared to the other methods in the MGUS vs. multiple myeloma test. The paired t-tests give p-values between 0.002 and 0.031 (unadjusted for multiple comparisons) for the EOV compared with the other 5 models in the MGUS vs. multiple myeloma test. According to this test, the EOV has a significantly lower rate of correct classification, though it is the most accurate MGUS classifier as shown above. In comparing two groups, this is often the trade off between sensitivity and specificity.

Models for predicting group membership were identified for each method. The models classifying multiple myeloma vs. MGUS had more overlapping genes (17 unique genes) then the models classifying multiple myeloma vs. Normal (12 unique genes) or MGUS vs. Normal (10 unique genes.) A possible explanation for this is that there are probably numerous genes that distinguish multiple myeloma and normal samples because the two groups are quite distinct. However, the genetic similarities between multiple myeloma and MGUS lead to fewer number of genes that are different across the two groups. This dearth of distinguishing genes conditions any good model to contain some of the same limited number of genes. A more detailed discussion of the particular genes is given in the conclusion.

Meta-Voting

As an additional step to improve the prediction capabilities of the method, a "meta" prediction value was calculated. For each of the logistic regression, SVM, and Bayes Net procedures, the marginal predicted group was calculated and then a final prediction was given as the top voted group. A sample is classified in a group if at least two of the three methods predict that group. The calculation indicate that the meta voting procedure does not improve the results.

Receiver Operator Characteristic (ROC) Curves

A Receiver Operating Characteristic (ROC) curve demonstrates the relationship between sensitivity (correct prediction to the more diseased group) and specificity (correct prediction to the less diseased group). FIG. 16 gives the ROC curves for the comparison of MM (multiple myeloma) vs. MGUS classification. The difficult comparison (multiple myeloma vs. MGUS) is challenging for all the methods. For example, naïve Bayes has a high sensitivity but at the cost of low specificity. For even mediocre values of specificity, the sensitivity drops off quite rapidly. In order to have a high sensitivity for any of the methods (that is, in order to have very few false positives of multiple myeloma), the ability to predict MGUS accurately (specificity) was compromised.

Prediction of MGUS

The models that classify the multiple myeloma and normal samples into distinct groups may also be able to be used as a predictive model for samples that are not clearly in either group based on clinical data. As a whole, the MGUS samples are clinically healthy (except for high levels of immunoglobulins) but genetically appear malignant. Applying the multiple myeloma vs. normal model to the MGUS samples will give us an idea as to which group the MGUS samples look more like. Table 19 provides the prediction distribution for the MGUS samples into the multiple myeloma and normal groups based on the model which compared multiple myeloma to normal samples. On average, about 90% of the MGUS samples are classified as multiple myeloma, and about 10% are classified as normal. The possible reason for this is that the 10% who are classified as normal may have longer survival times and less disease progression. Regardless, the similarity of MGUS to multiple myeloma (even in the model that was derived without any MGUS) gives additional evidence that the MGUS is actually genetically much more similar to the multiple myeloma than to the normal samples. From both the prediction of the dichotomous groups and the classification of MGUS samples into the two extreme groups, it can be concluded that the methods are not notably different.

In order to better understand the mechanisms behind the poor classification of the MGUS samples (when compared to multiple myeloma), the number of MGUS classified as multiple myeloma for each of three methods, logistic regression, SVM, and Bayes Net was tabulated. Of the 32 MGUS samples, the misclassification rates are given in Table 20. There were 26 MGUS samples misclassified using the logistic procedure; 17 of the 26 were also misclassified using SVM, and 18 of the 26 were misclassified using Bayes Net.

This cross tabulation indicates that the misclassified MGUS samples are continuously getting misclassified which lends evidence to a possible subset of MGUS samples that are genetically similar to the multiple myeloma samples.

TABLE 19

MM vs. Normal (predicting MGUS)

| % MGUS classified as: | MM | Normal |
|---|---|---|
| Logistic | 87.5% | 12.5% |
| Trees | 93.75% | 6.25% |
| SVM | 93.75% | 6.25% |
| Bayes Net | 93.75% | 6.25% |
| EOV | 84.37% | 15.63% |
| Naïve Bayes | 93.75% | 6.25% |

TABLE 20

| # MGUS misclassified | Logistic | SVM | Bayes Net |
|---|---|---|---|
| Logistic | 26 | 17 | 18 |
| SVM | | 21 | 17 |
| Bayes Net | | | 21 |

Discussion

Six different statistical and data mining algorithms were examined for their ability to discriminate normal, hyperplastic, and malignant cells based on the expression patterns of ~12,000 genes. The models were highly accurate in distinguishing normal plasma cells from abnormal cells. However, these models displayed a uniform failure in the discrimination between the hyperplasic cells and malignant cells. A major goal of this study was to develop or modify data mining tools in order to capture a small subset of genes from massive gene expression data sets to accurately distinguish groups of cells, e.g. normal, precancerous, and cancerous cells, with the ultimate goal to create sensitive and reproducible molecular-based diagnostic tests. In addition, future studies can be aimed at using a similar strategy to identify a minimum subset of genes capable of discriminating subgroups of disease for risk stratification and prognostics. This is a particularly important concept for this disease as the overall survival in multiple myeloma is highly variable, with some patients surviving as long as 10 years while others die within several months of diagnosis. Current microarrray studies require the isolation of large numbers of cells that necessitate advanced facilities and expertise. The studies described in this example represent the first step toward streamlining this process, as a smaller subset of genes (10-20) with a high predictive power allows for a massive reduction in scale, which in turn will make development of a commercial test more amenable to mass production and hence widespread clinical use.

One possible reason for the inability of the models to discriminate MGUS (monoclonal gammopathy of undetermined significance) from multiple myeloma is that MGUS represents at least two different diseases. This is supported by the overlap in misclassification of MGUS samples as shown in Tables 19-20. In simplistic terms, MGUS can be viewed as a disease that will remain indolent or one that will convert to overt malignancy. Accruing sufficient numbers of stable and progressive MGUS cases along with sufficient follow-up time will help resolve this issue.

The failure of the models to differentiate the two disease types could be related to the limitations of the current methodologies. The microarray profiling utilized here only interrogated ⅓ of the estimated 35,000 human genes (International Human Genome Sequencing Consortium, 2001; Venter et al., 2001), thus it is possible that a whole genome survey would reveal discriminating features. A new Affymetrix U133 GENECHIP® (Gene Chip) system which is thought to interrogate all human genes may be used to address this question. It is also possible that a whole genome analysis will reveal no significant differences. This revelation could mean any of a variety of possibilities: (1) there is no genetic difference between the two diseases, (2) only the MGUS that are classified as multiple myeloma are genetically similar to multiple myeloma, and the clinical tests are unable to identify that distinction, (3) the current microarray technology is not specific enough to measure the differences between the two diseases, (4) the methods described above are not appropriate for this type of analysis. If (1) or (2) is true, these results would point to other determinants of an indolent or malignant course such as genetic predisposition or somatic DNA mutations not manifest in gene expression, a unique environmental exposure interacting with these predisposing genetic traits, or a non-tumor cell microenvironment or "soil" that promotes plasma cell growth.

Another goal of this work was to use the models of global gene expression profiling to define critical genetic alterations that accompany the transition of a plasma cell from its normal homeostasis to a benign hyperplasia and from hyperplasia to an overt malignancy. Integration of the data from the six models revealed a group of genes that were found in two or more of the models. For purposes of this study these genes were interpreted to represent the most differentially expressed in these transitions. Ten common genes were identified in the normal to MGUS (monoclonal gammopathy of undetermined significance) comparison with 8 of the genes being down-regulated or shut down in the abnormal cells. A similar phenomenon was seen in the normal versus multiple myeloma comparison with 9 of 12 common genes being down-regulated. This was in contrast to the MGUS versus multiple myeloma comparison where almost half (8 of 18 probe sets representing 17 unique genes) of the probe sets were up-regulated in multiple myeloma. Probes sets for 4 different chemokine genes SCYA23 (Normal vs. MGUS), SDF1 (Normal vs. MM), and SCYC2 and SCYA18 (MGUS vs. MM) were down-regulated in the latter group in each of the 3 comparisons. Two probe sets for SCYA18 were found in the MGUS vs. MM comparison. This is an important validation of SCYA18 gene expression truly being different in the two conditions. Chemokines are important mediators of immune responses and act as soluble factors that induce the migration of specific immune cells to sites of inflammation. The potential significance of the loss of expression of multiple chemokine genes in plasma cell dyscrasias is not understood, but may point to how tumors may suppress anti-tumor immune reactions.

As with SCYA18, two unrelated probe sets for the human homologue of the Drospohila melangaster gene frizzled (FZD2) were down-regulated in the normal to MGUS transition. FZD2 codes for a membrane bound receptor that binds a highly conserved family of soluble ligands known as WNTs. WNT signaling regulates homeotic patterning and cell-fate decisions in multicellular organisms ranging from flies to humans. The Wnt signaling cascade has also been shown to be involved in neoplasia as hyperactivation of the Wnt-1 gene by viral insertional mutagenesis caused spontaneous mammary tumorigenesis in mice. It is suspected that loss of FZD2 expression in MGUS carries potential significance given that expression profiling has revealed deregulated expression of multiple members of the WNT signaling pathway in multiple myeloma and plasma cell leukemia (results shown above; Zhan et al., 2002a; De Vos et al., 2001). Results in previous examples presented above also show that a secreted antagonist of WNT signaling, FRZB, exhibits elevated expression in a comparison of normal plasma cells and multiple myeloma (Zhan et al., 2002a; De Vos et al., 2001). The concomitant, or possibly sequential, down-regulation of the functional WNT receptor (FZD2) and up-regulation of a decoy receptor strongly suggests that disruption of WVNT signaling plays a pathological role in multiple myeloma development. In addition to abnormalities in the receptor and decoy genes, the genes for the ligands, WNT5A and WNT10B, have been identified as altered in multiple myeloma (results shown above; Zhan et. al., 2002). Whereas WNT5A is upregulated in multiple myeloma, WNT10B is expressed at high levels in normal plasma cells but not in a majority of multiple myeloma plasma cells (Zhan et. al., 2002a). It is of note that recent studies have demonstrated that Wnt-5A, Wnt-2B, Wnt-10B, Wnt-11 comprise a novel class of hematopoietic cell regulators.

Taken together these findings suggests that deregulated autocrine and/or paracrine Wnt signaling may play a pivitol role in plasma cell dyscrasias and that a progressive deregulation of multiple components of the signaling complex may be associated with disease progression from normal plasma cells to hyperplastic, but benign, MGUS then to overt multiple myeloma. In conclusion, it is anticipated that strategies like those employed here will allow the creation of new molecular diagnostic and prognostic tests and should provide useful insight into the genetic mechanisms of neoplastic transformation.

EXAMPLE 19

Elevated Expression of Wnt Signaling Antagonists DKK1 and FRZB in Myeloma Plasma Cells is Associated with Lytic Bone Disease Multiple myeloma is the only hematological malignancy consistently associated with debilitating lytic bone disease. The prevalence of bone disease varies with the presentation of multiple myeloma, from smoldering multiple myeloma often without bone involvement, to solitary plasmacytoma, to diffuse or focal multiple myeloma where systemic losses of bone mineral density or focal lytic bone lesions are seen in 80% of patients. Progression from the pre-malignant monoclonal gammopathy of undetermined significance (MGUS) to overt multiple myeloma is preceded by changes in bone turnover rates. Bone loss tends to be located adjacent to malignant plasma cells, suggesting that multiple myeloma plasma cells secrete factors that induce osteoclast activation and/or suppress osteoblast growth and differentiation.

To identify secreted factors linked to multiple myeloma bone disease, the expression profiles of ~12,000 genes was compared in CD138-enriched plasma cells (PC) from newly diagnosed multiple myeloma (MM) with no radiological evidence of osteolytic bone lesions (n=87) to those with ≧3 lytic lesions (n=83). Of a total of 367 genes identified, 229 were higher and 138 lower in PC from MM with lytic lesions. Expression of genes associated with cell proliferation, e.g. PCNA, TYMS, PRKDC, CENPA, and TOP2A predominated in M M with lytic lesions. In contrast ARHE, IL-6R, WNT10B, and the B-cell receptor molecules SLAM, TACI, and LNHR, were notable genes expressed at significantly lower levels in M M with lytic lesions. Consistent with a critical role of WNT signaling in osteoblast growth and differentiation (see below), the two secreted WNT signaling antagonists, soluble frizzled related protein 3 (SFRP-3/FRZB) and DKK1, represented the only genes coding for secreted factors within the top 50 up-regulated genes. Importantly, DKK1 and FRZB were not expressed in PC from 45 normal bone marrow donors or 10 Waldenstrom's macroglobulinemia, a PC malignancy that lacks bone disease, and monoclonal gammopathy of undetermined significance (MGUS). Both immuno-histochemistry and immunofluoresence of biopsy material confirmed gene expression data.

Since lytic bone lesions develop at sites of MRI-defined medullary plasmacytoma (MPCT), MRI represents a highly sensitive surrogate for present or future osteolytic lesions. As MRI-defined MPCT can be observed in the absence of x-ray detectable lytic lesions, it is hypothesized that those cases with no lytic lesions, yet having underlying MPCT might skew the data analysis when correlating gene expression with x-ray data alone. Thus, the inventors combined x-ray and MRI data and applied $\chi^2$, WRS, and SAM analyses to compare 65 newly diagnosed cases of MM exhibiting three or more lytic lesions and three or more MPCT with 43 cases exhibiting no lytic lesions or MPCT. A total of 107 genes differentiating the two groups at $P<0.001$ were identified. Importantly many of the same genes, e.g. cell cycle genes, identified above were also identified in the latter analysis and the levels of difference have increased. For example, whereas the ratio (bone disease/no bone disease) of the mean expression level for DKK1 in the first comparison was 2.45, the mean value increased to 6.25 in the latter. This reflected the fact that virtually all cases with no lytic lesions and moderate to high DKK1 had MRI-defined focal lesions. The mean expression level of DKK1 in the no lytic lesion group was 1674 (range 40 to 10828) whereas the mean DKK1 level in the no lytic lesion & no focal lesion group dropped to 625 (range 57 to 4183).

It is important to note that DKK1 and FRZB expression, as determined from bone marrow aspirates of the iliac crest, although very powerful, can not account for the presence of bone lesions in all patients, as cases exists that have x-ray lesions in which the multiple myeloma plasma cells do not express appreciable levels of DKK1 or FRZB. Several possibilities may account for this observation. First, it is possible that if plasma cells were isolated from MPCT at focal lesions the cells might have high levels of either these genes. Alternatively, a quantitative trait locus (QTL) for low bone mass in the general population may enhance bone lesion development even in the presence of low levels of DKK1 and FRZB. Finally, it is likely that DKK1 independent mechanisms, e.g. osteoclast hyperactivation, are also at work in the development of bone disease. Nonetheless, it is remarkable that cells from random bone marrow aspirates of the iliac crest have gene expression profiling (GEP) features expected of plasma cells derived from MPCT adjacent to lytic lesions. Thus comparative GEP studies of CT-guided fine needle aspirates of MPCT and random aspirates from the same patient should reveal stronger similarities rather than differences. Preliminary studies of this design have in fact revealed no major distinguishing GEP features, including of DKK1 and FRZB, between the two cell types.

It have recently shown that expression of the cell cycle control and DNA metabolism genes TYMS, UBE2C, CCNB1, PCNA, TK1, BUB1, BUB1, EZH2, and TOP2A is significantly higher in MM with metaphase cytogenetic abnormalities (CA) and that these features are linked to poor survival. These same genes were also over-expressed in MM with lytic lesions and MPCT and especially in cases with both, suggesting this type of MM is also likely to have a high proliferation index and may provide a molecular explanation for why MM with >3 lytic lesions is classified as a high risk stage III disease in the Durie Salmon staging system.

Although exhibiting highly variable and sometimes very high expression in multiple myeloma plasma cells, MIP-1-alpha (CCL3/SCYA3), a chemokine implicated in OCL development and multiple myeloma bone disease, was not significantly differentially expressed in this analysis. In addition, RANKL, a known osteoclast differentiation factor with conflicting data concerning its expression on multiple myeloma plasma cells, has not been detected in any multiple myeloma plasma cells or normal bone marrow plasma cell sample tested with our microarray system.

Consistent with a key role for JUN in controlling DKK1 expression and in turn apoptosis, it has been shown that plasma cells derived from extramedullary disease, as well as primary refractory disease, and human multiple myeloma cell lines have low to undetectable levels of both JUN and DKK1. It has also been shown that primary multiple myeloma cells co-cultured with in vitro derived osteoclasts are long-lived and moderately proliferative and that these cells down-regulate JUN, FOS, FOSB, and DKK1 after co-culture (Yaccoby et al., 2002). Thus, one of the mechanisms by which OCL may prolong multiple myeloma plasma cell survival is through the down-regulation of DKK1 via the down-regulation of JUN.

The relevance of elevated DKK1 and FRZB expression in multiple myeloma bone disease is derived from several recent studies that have shown that functional Wnt signaling is critical for osteoblast differentiation and function. Patients exhibiting loss of function mutations in the low-density lipoprotein receptor-related protein 5 (LRP5), a co-receptor for the Wnt ligand, have a condition known as osteoporosis-pseudoglioma (OPPG). Importantly, separate and distinct mutations in LRP5 result in a high bone mass (HBM) phenotype. In contrast to the OPPG mutations, the HBM defects represent gain-of-function mutations that effectively block binding of the inhibitory protein DKK1. Thus, it is speculated that high local levels of secreted DKK1 and FRZB at the sites of MPCT blocks LRP5 function on osteoblasts, which in turn results in apoptosis or a block to terminal differentiation.

Obligate carriers of the OPPG mutations can have reduced bone mass and a QTL near LRP5 on 11q12 influences bone density in the general population. It is therefore conceivable that multiple myeloma bone disease may also be influenced by this QTL, as patients inheriting a low bone mass allele and whose multiple myeloma plasma cells express high levels of DKK1 may be at higher risk of developing bone disease than those with just one of these features. The inheritance patterns of this QTL could also help explain the presence of lytic lesions in patients with low DKK1 and low FRZB. It is also interesting to speculate that the risk of conversion of monoclonal gammopathy of undetermined significance (MGUS) to multiple myeloma may also be influenced by this QTL. Thus it is of interest to determine the genotypes for this locus in a large population of multiple myeloma and MGUS cases and age-gender matched controls and correlating this with DKK1 expression, bone mass, and bone disease.

Osteolysis is the most common skeletal manifestation of neoplasia and may be focal or generalized. Given that prostate and placenta are the only adult tissues that express appreciable levels of DKK1 and that metastatic prostate adenocarcinomas to the bone are frequent and associated with osteoblastic and sometimes osteolytic lesions, it is intriguing to speculate that metastatic prostate cancers as well as other bone metastasizing tumors expressing high levels of DKK1 may also contribute to osteolytic lesions. It is also interesting to speculate that osteoporosis in the general population may also be linked to elevated DKK1.

The data linking DKK1 up-regulation after drug treatment, its down-regulation in late stage disease and after OCL co-culture, its high expression in multiple myeloma with bone lesions, and published reports on the molecular biology of DKK1 expression has prompted the inventors to develop a working model for DKK1 in multiple myeloma. It is envisioned that in the early stages of disease, an inherent genomic instability induces expression of DKK1 which in turn induces apoptosis of multiple myeloma cells and may explain the relatively slow progression of the disease, as cell growth is tempered by a high rate of DKK1 induced apoptosis. However, as the disease progresses, high levels of DKK1 secreted from the multiple myeloma cells results in profound defects in osteoblast function and combined with osteoclast hyper-activation leads to uncoupled bone turnover and the development lytic bone lesions and diffuse osteopenia. As osteoclast numbers increase these cells induce the down-regulation of JUN and DKK1 in multiple myeloma plasma cells, liberating the multiple myeloma plasma cells from the pro-apoptotic effects of DKK1, resulting in an increased tumor cell burden. Although DKK1 loss in the early stages of disease progression is likely due to down-regulation of JUN that is induced by an osteoclast derived factor, permanent loss of DKK1 expression late in disease is likely due to the loss of p53. Thus, DKK1 in multiple myeloma has a paradoxical twist, in that even though secreted DKK1 may facilitate apoptosis of multiple myeloma plasma cells, it may also block osteoblast growth and differentiation, which in turn creates a bone marrow microenvironment primed for disease progression. If true, utilization of this knowledge could lead to the development of new therapies for MM that accentuate and preserve the pro-apoptotic effects of DKK1 on MM PC, but at the same time prevent its bone damaging effects.

EXAMPLE 20

DKK1 is Secreted by Plasma Cells and Contributes to Osteolytic Lesions in Multiple Myeloma Examples 20-22 show that DKK1 is the only gene coding for secreted proteins that is significantly elevated in the malignant plasma cells from patients with bone lesions at diagnosis. DKK1 protein is synthesized and secreted into the marrow space where elevated levels also correlate with plasma cell gene expression levels and the presence of bone lesions. Finally, it is shown that plasma from multiple myeloma bone marrow containing high levels of DKK1 blocks in vitro osteoblast differentiation in a DKK1-dependent manner, whereas plasma from normal healthy donors does not.

Because osteolytic lesions develop at the site of MRI-defined focal medullary plasmacytomas and DKK1 levels strongly correlate with the presence of MRI-focal lesions, it is speculated that DKK1 protein levels are high in the environment surrounding "nests" of plasma cells, leading to an incapacitation of osteoblasts adjacent to these plasma cell clusters. Concentration gradients of the Wnt ligands and their soluble inhibitors, e.g. DKK1, are important in the creation of body segmentation and cellular polarity. Thus, DKK1 may exert most of its inhibitory effects directly adjacent to plasmacytomas, and thus may provide a functional explanation as to why lytic lesions are always found next to medullary plasmacytomas and not in unaffected areas. Because plasma cells make up ≦5% of all bone marrow cells and plasma cells are the only source of DKK1 in human bone marrow, elevated DKK1 levels in the marrow could also be related to systemic osteoblast defects and osteopenia when tumor cell burden reaches a critical threshold. Published work showed that when tumor cell burden increases above 50%, osteoblast mineral apposition rates are dramatically reduced.

Not all multiple myeloma patients with bone lesions exhibited elevated levels of DKK1. Several possibilities may account for this observation. Obligate carriers of the OPPG mutations can have reduced bone mass and a quantitative trait loci (QTL) near LRP5 on 11q12 influences bone density in the general population. Thus, QTL inheritance patterns could explain the presence of lytic lesions in patients with low DKK1 expression, as the presence of a low bone mass allele and low DKK1 levels may create a high risk for developing bone lesions. It is also possible that the Wnt signaling antagonist FRZB, which is elevated in multiple myeloma and multiple myeloma with osteolytic lesions (data not shown), and which negatively regulates chondrocyte development could synergize with DKK1 to contribute to osteoblast dysfunction and bone lesions.

Although Wnt/β-catenin signaling defects are implicated in hereditary syndromes affecting bone, the data presented herein are the first evidence that disrupting this signaling cascade is also linked to bone destruction in non-hereditary conditions. These data also support the notion that elevated DKK1, and possibly other Wnt signaling antagonists, might play a role in other forms of bone loss. Soluble Wnt antagonist SFRP-2, and possibly DKK1, is downregulated by estrogen; thus it is important to determine whether DKK1 protein levels or other Wnt antagonists are elevated in post-menopausal women and whether protein levels correlate with osteoporosis. Furthermore, given that breast cancer metastasis to the bone is frequently associated with osteolytic lesions, it is important to determine if DKK1 expression is elevated in these cases. Finally, these data support the concept that pharmacological antagonism of DKK1 action may be a means of controlling both malignancy-related bone loss, and post-menopausal or other forms of osteoporosis.

Global Gene Expression Profiling of Malignant Plasma Cells Links DKK1 with Bone Lesions One hundred seventy four patients with newly diagnosed multiple myeloma, 45 normal healthy donors, and 10 patients with Waldenstrom's macroglobulinemia were studied in this example. The characteristics of the multiple myeloma patients are presented in Table 21.

Bone images were reviewed on a Canon PACS (Picture Archiving and Cataloging System). MRI scans were performed on 1.5 Tesla GE Signa® scanners. X-rays were digitized from film in accordance with American College of Radiology (ACR) standards. MRI scans and x-rays were linked to the Canon PACS system using the ACR's DICOM (Digital Imaging and Communications in Medicine) standard. Imaging was done in accordance with manufacturers' specifications. MRI images were created with pre- and post-gadolinium T1-weighting and STIR (short-tau inversion recovery) weighting.

MRI-defined focal lesions can be observed before the development of radiologically identifiable lytic lesions; therefore, T1-weighted and STIR-weighted imaging was used to evaluate bone lesions in multiple myeloma. Bone disease in multiple myeloma patients was modeled using logistic regression. DKK1 protein and gene expression values, measured using the signal calls from the Version 5.01 Affymetrix Analysis Suite, were transformed using the Log Base 2 function prior to entry into the logistic regression model. Candidate genes were reduced to 58 genes with the lowest p-value from logistic regression (P<0.00012). T-tests with permutation-adjusted p-values verified the significance of the 58 genes at the 0.05 level. Except in the process of reducing candidate genes, p-values less than 0.05 were considered significant and p-values less than 0.10 were considered marginally significant. Expression intensities of genes identified by logistic regression were visualized with ClusterView (Li and Wong, 2001). Gene expression and protein levels were correlated with Spearman or Pearsons correlation metric.

Logistic regression and permutation analysis of global gene expression differences in purified plasma cells from patients with none (n=36) and those with 1 or more (1+) (n=137) MRI-defined focal lesions identified 30 downregulated and 28 upregulated genes that were significantly differentially expressed (P<0.0001) in patients with 1+ MRI lesions (FIG. 17A). The soluble Wnt/β-catenin signaling antagonist DKK1 ranked 4th in significance (P=4.3×10$^{-6}$) and represented the only gene coding for a secreted factor in the list. DKK1 was undetectable by microarray analysis of bone marrow plasma cells from 45 normal healthy donors and 10 patients with Waldenström's macroglobulinemia, a plasma cell malignancy that lacks lytic bone disease (data not shown).

Using the same comparative ranking criteria for x-ray identifiable osteolytic lesions, DKK1 expression was again significantly elevated in patients with 1+ lesions (P=0.0068), but ranked 199 of ~10,000 genes investigated (data not shown). Because osteolytic lesions always develop at sites of MRI-detectable focal lesions and MRI lesions can be present in the absence of lytic lesions, it is hypothesized that multiple myeloma patients with no x-ray lesions, but high DKK1 expression, would have MRI lesions, thus explaining the reduced ranking of DKK1. Indeed, removing patients with 1+ MRI lesions from the group with no x-ray lesions resulted in DKK1 moving to the 5th most significant gene (P=0.0000089) when comparing those patients with no x-ray lesions and no MRI lesions with patients who had 1+ x-ray lesions (data not shown).

Increased Log2 (DKK1) expression increases the likelihood of having 1+ MRI lesions (OR 1.42 [95% CI: 1.21, 1.66], P<0.0001) (FIG. 17B). This relationship is still statistically significant, but of less magnitude for patients with 1+x-ray lesions (OR: 1.19 [95% CI: 1.04, 1.35], P=0.0084). Again, removing patients with 1+ MRI lesions from the no x-ray lesion group reveals that the relationship of DKK1 and lesions detected by x-ray (adjusted) (OR 1.43 [95% CI: 1.20, 1.69], P<0.0001) mirrors that of lesions detected by MRI. Though this is not conclusive evidence of a link between elevated DKK1 and bone lesions, the pattern of DKK 1 expression is consistent with the theory that DKK1 and MRI are strong early indicators of x-ray-defined osteolytic lesions.

Immunohistochemistry and Immunofluorescence

A polyclonal goat anti-human DKK1 antibody (R&D Systems, Minneapolis, Minn.) diluted 1:200 in TBS was incubated on formalin-fixed, paraffin-embedded multiple myeloma bone marrow biopsy sections for 2 hours at room temperature. Anti-kappa or -lambda antibodies (Dako, Carpenteria, Calif.) diluted 1:1200 were incubated on adjacent sections for 30 minutes at room temperature. Antigen-antibody reactions were developed with DAB (using biotinylated anti-goat antibody (1:400 dilution, Vector Laboratories, Burlingame, Calif.) and streptavidin-horse radish peroxidase (Dako)), and counterstained with Hematoxylin-2. For immunofluorescence, cells were fixed in 4% paraformaldehyde, blocked with 1% bovine serum albumin (BSA)/Hank's balanced salt solution (HBSS) for 10 minutes, then incubated with 1 ug/ml anti-human DKK1 antibody followed by a Rhodamine-conjugated rabbit anti-goat IgG F(ab')$_2$ fragment (1:500 dilution, Jackson ImmunoResearch, West Grove, Pa.). Cytoplasmic immunoglobulin kappa or lambda light chains were stained with FITC-conjugated goat anti-human kappa or lambda IgG at 1:100 dilution (Vector Laboratories). All slides were examined with fluorescence optics on an Olympus BX60 epifluorescence microscope and photographed at 1000× magnification.

DKK1 protein is synthesized by malignant and normal plasma cells. Serial sections from bone marrow biopsies of 30 multiple myeloma cases stained with antibodies against cytoplasmic immunoglobulin kappa or lambda light chain (cIg) and DKK1 revealed plasma cells expressed DKK1 in a manner consistent with gene expression data (FIGS. 18A-D). Simultaneous two-color immunofluoresence microscopy on mononuclear cells from bone marrow aspirates of 30 multiple myeloma patients and 9 normal healthy donors was consistent with immunohistochemistry results, showing DKK1 protein expression exclusively in cIg-restricted plasma cells (FIGS. 2E-H). As seen in the multiple myeloma bone marrow aspirates, non-plasma cells in normal marrow did not express DKK1; however, approximately ⅓ to ½ of cIg-positive plasma cells expressed DKK1. Although DKK1 expression was not detected by microarray, DKK1 expression, albeit low, could be detected in purified bone marrow plasma cells by real time RT-PCR (data not shown).

TABLE 21

Myeloma Patient Characteristics And Their Relationship To MRI Lesions

| Variable | n/N | % | MRI = 1+ | MRI = 0 | P value |
|---|---|---|---|---|---|
| Age ≧ 65 yr | 23/169 | 14 | 17/132 (12.9%) | 6/36 (16.7%) | 0.5869* |
| Caucasian | 147/169 | 87 | 113/132 (85.6%) | 33/36 (91.7%) | 0.4163* |
| Female | 68/169 | 40 | 55/132 (41.7%) | 13/36 (36.1%) | 0.5472 |
| Kappa light chain | 104/165 | 63 | 79/128 (61.7%) | 24/36 (66.7%) | 0.5874 |
| Lambda light chain | 61/165 | 37 | 49/128 (38.3%) | 12/36 (33.3%) | 0.5874 |
| IgA subtype | 39/169 | 23 | 25/132 (18.9%) | 14/36 (38.9%) | 0.0120 |
| B2M ≧ 4 mg/L | 60/169 | 36 | 47/132 (35.6%) | 13/36 (36.1%) | 0.9553 |
| CRP ≧ 4 mg/L | 12/166 | 7 | 11/129 (8.5%) | 1/36 (2.8%) | 0.4662* |
| Creatinine ≧ 2 mg/dL | 19/169 | 11 | 16/132 (12.1%) | 3/36 (8.3%) | 0.7673* |
| LDH ≧ 190 UI/L | 52/169 | 31 | 44/132 (33.3%) | 8/36 (22.2%) | 0.2012 |
| Albumin < 3.5 g/dL | 23/169 | 14 | 19/132 (14.4%) | 4/36 (11.1%) | 0.7868* |
| Hgb < 10 g/dL | 40/169 | 24 | 31/132 (23.5%) | 8/36 (22.2%) | 0.8736 |
| PCLI ≧ 1% | 23/150 | 15 | 18/119 (15.1%) | 4/30 (13.3%) | 1.0000* |
| ASPC ≧ 33% | 109/166 | 66 | 82/129 (63.6%) | 26/36 (72.2%) | 0.3342 |
| BMPC ≧ 33% | 104/166 | 63 | 79/128 (61.2%) | 24/36 (66.7%) | 0.5522 |
| Cytogenetic abnormalities | 52/156 | 33 | 45/121 (37.2%) | 6/34 (17.6%) | 0.0321 |

TABLE 21-continued

Myeloma Patient Characteristics And Their Relationship To MRI Lesions

| Variable | n/N | % | MRI = 1+ | MRI = 0 | P value |
|---|---|---|---|---|---|
| CA13 or hypodiploid | 33/52 | 63 | 31/121 (25.6%) | 3/34 (8.8%) | 0.0365 |
| Other CA | 19/52 | 37 | 53/103 (51.5%) | 16/32 (50.0%) | 0.8855 |
| FISH13 | 69/136 | 51 | 103/136 (75.7%) | 28/36 (77.8%) | 0.7981 |
| Osteopenia | 131/173 | 76 | | | |
| 1+ Lesions by MRI | 137/173 | 79 | | | |
| 3+ Lesions by MRI | 108/173 | 62 | | | |
| 1+ Lesions by X-ray | 105/174 | 60 | | | |
| 3+ Lesions by X-ray | 69/174 | 40 | | | |

*Fisher's Exact test, otherwise Chi-square test

EXAMPLE 21

Correlation between Levels of DKK1 Protein in Bone Marrow Plasma and the Presence of Bone Lesions An enzyme-linked immunosorbent assay (ELISA) was used to measure DKK1 protein concentration in the bone marrow plasma. Nunc-Immuno MaxiSorp surface microtiter plates were coated with 50 ul of anti-DKK1 antibody at 1 ug/ml in 1×PBS, pH 7.2 at 4° C. overnight, and blocked with 4% BSA. Bone marrow plasma from multiple myeloma, Waldenström's, and normal donors was diluted 1:50 in dilution buffer (1×PBS+0.1 Tween-20+1% BSA). A total of 50 μl was loaded per well and incubated overnight at 4° C., washed and incubated with biotinylated goat anti-human DKK1 IgG (R&D Systems) diluted to 0.2 ug/ml in dilution buffer, followed by addition of 50 μl of 1:10,000 dilution of streptavidin-horse radish peroxidase (Vector Laboratories) all according to manufacturer's recommendations. Color development was achieved with the OPD substrate system (Dako) based on manufacturer's instructions. Serial dilutions of recombinant human DKK1 (R&D Systems) were used to establish a standard curve. The cell line T293, which does not express endogenous DKK1 and T293 with stably transfected DKK1 were used to validate the ELISA assay.

DKK1 protein concentration in the bone marrow plasma from 14 normal healthy donors was 8.9 (S.D. 4.2) ng/ml. In contrast, the mean plasma concentration in 205 newly diagnosed multiple myeloma patients was 28.37 (S.D. 54.45) ng/ml and the mean level in 9 Waldenström's acroglobulinemia patients was 5.5 (S.D. 2.4) ng/ml. Both DKK1 gene expression and DKK1 protein levels determined in 107 multiple myeloma cases were strongly correlated (r=0.65, P<0.00001) (FIG. 19A). DKK1 protein levels were correlated with bone lesions in 74 multiple myeloma in which both measurements were available. DKK1 protein levels were significantly higher in patients with 1+ MRI versus those with no MRI lesions (OR: 1.98 [95% CI: 1.18, 3.32], P=0.012) (FIG. 19B), but only marginally significant for 1+ x-ray lesions versus no lesions (OR: 1.38 [95% CI: 0.95, 2.00], P=0.09) (FIG. 19B). However, as observed for DKK1 gene expression (see FIG. 17B), serum DKK1 protein levels can discriminate patients with no MRI and no x-ray lesions from patients with 1+ MRI and no x-ray lesions (OR: 7.46 [95% CI: 1.40, 39.82], P=0.0186), but cannot discriminate the 1+ MRI lesions and 1+ x-ray lesions group from the 1+ MRI lesions/no x-ray lesions group (OR: 1.14 [95%CI: 0.98, 1.32], P=0.5752) (FIG. 19B). These data show that DKK1 proteins levels are elevated in MM bone marrow, that DKK1 gene expression levels in multiple myeloma plasma cells correlate with DKK1 protein levels in the serum, and that DKK 1 serum levels also correlate with the presence of bone lesions.

EXAMPLE 22

Multiple Myeloma Marrow Serum Blocks In Vitro Osteoblast Differentiation in a DKK1-Dependent Fashion BMP-2 specifically converts the differentiation pathway of C2C12 myoblasts into that of osteoblast lineage and BMP-2 induced osteoblast differentiation of mesenchymal precursor cells in vitro involves Wnt/β-catenin signaling. Thus, it is of interest to determine if multiple myeloma serum containing high levels of DKK1 could block BMP-2 induced alkaline phosphatase (ALP) production by C2C12 cells.

C2C12 mesenchymal precursor cells (American Type Tissue Culture, Reston, Va.) were cultured in DMEM (Invitrogen, Carlsbad, Calif.) supplemented with 10% heat-inactivated fetal calf serum. BMP-2 induced alkaline phosphatase activity in C2C12 cells was measured as previously described (Gallea et al., 2001; Spinella-Jaegle et al., 2001). Briefly, C2C12 cells were plated at $2\times10^4/cm^2$ in 5% FCS and treated 24 hours later by addition of 0.1 ug/ml BMP-2+10% normal serum, or 10% multiple myeloma patient serum (resulting in final DKK1 concentration of at least 15 ng/ml), or 10% multiple myeloma patient serum+anti-DKK1 antibody or non-specific goat polyclonal IgG (Jackson ImmunoResearch) at a 5:1 molar ratio to DKK1. After 5 days, ALP activity was determined in cell lysates using an Alkaline Phosphatase Opt Kit (Roche Molecular Biochemicals). Cell lysates were analyzed for protein content using the micro-BCA assay kit (Pierce, Rockford, Ill.). Each experiment was done in triplicate.

It was first showed that TGF-β (2.5 ng/ml) and recombinant human DKK1 (12.5 ng/ml) could block ALP production after treatment with 0.1 ug/ml of BMP-2 for 5 days (data not shown). ALP levels were undetectable in C2C12 cells grown in 5% FCS for 5 days (FIG. 20). C2C12 cells treated with BMP-2 and 10% serum from a normal donor induced ALP activity to a mean of 0.72 mM/min/mg total protein. Cells treated with 10% serum from two multiple myeloma cases (final DKK1 concentration 20 ng/ml and 16.8 ng/ml) resulted in a significant reduction of ALP levels relative to the normal control. However, co-incubation with DKK1 antibodies resulted in a significant increase in ALP levels. Co-incubation with a non-specific polyclonal goat IgG did not have a significant affect on ALP levels relative to multiple myeloma serum alone. These data show that serum from multiple myeloma patients, but not normal donors, can block in vitro osteoblast differentiation in a DKK1-dependent fashion.

EXAMPLE 23

Gene Expression Profiling Implicates Wnt Signaling in Multiple Myeloma

In addition to a possible role for FRZB and DKK1 in multiple myeloma (MM) bone disease and DKK1 in drug induced MM cell apoptosis, additional components of the Wnt signaling system also show expression perturbations in MM. Wnt signaling is mediated by the Frizzled (FZD1-FZD10) seven-transmembrane-span receptors alone or when complexed with heterotrimeric G proteins or essential co-receptors LRP5/6. Intracellular signaling branches into either the canonical β-catenin-TCF pathway that activates target genes in the nucleus, the Wnt/Ca$^{2+}$ pathway or the planar cell polarity pathway which involves jun N-terminal kinase (JNK) and cytoskeleton modifications. With respect to the canonical β-catenin-TCF pathway, the absence of Wnt signal, which can be blocked by antagonist like FRZB and DKK1, results in β-catenin being sequestered in a complex with Axin, adenomatous polyposis coli (APC), CKIα and/or CKIε, ανδGSK-3β. Both CKIα/ε and GSK-3β phosphorylate β-catenin thereby targeting the protein for ubiquination and degradation by the proteasome. In the presence of Wnts, disheveled (Dsh) blocks β-catenin degradation possibly by recruiting GBP/Frat1, which displaces GSK3β from axin resulting in β-catenin stabilization. Stabilized β-catenin migrates to the nucleus where it associates with TCF/LEF transcription factors. Using the Affymetrix HUGENFL® (HuGenFL) microarray, it has previously been shown that, with respect to normal bone marrow PC, the TCF7 (TCF1) transcription factor and APC are down-regulated and up-regulated in MM, respectively (Zhan et al., 2002a). A recent analysis of 60 genes involved in or activated by WNT signaling in 222 MM and 45 normal bone marrow PC using the second-generation U95Av2 microarray revealed that TCF7 expression remained significant and represented the most significantly down-regulated WNT signaling gene in MM. The APC significance was lost in this new analysis probably owing to a change in the probe set interrogating the gene. The Wnt receptor FZD2 with a mean expression level of 1034 in MM and 2657 in normal bone marrow PC, represented the second most significant down-regulated gene. Importantly, FZD2 has also been found to be significantly down-regulated in MGUS and represents the only WNT signaling component found deregulated in benign plasma cell dyscrasia. DKK1 and FRZB, with ratios (MM/normal bone marrow PC) of mean expression levels of 25 and 14 respectively, represented by far the most significantly up-regulated WNT components in this analysis.

WNT5A and WNT10B tended to show up-regulation and down-regulation in MM respectively (Zhan et al., 2002a). In the new analysis the mean expression level for WNT5A was 217 (range 29 to 484) whereas the mean expression level in MM was 1299 (range 16 to 10782). In contrast, the mean expression level of WNT10B in normal bone marrow PC was 3239 (range 1552 to 6105) and 1881 (range 481 to 15354) in MM. Thus, these two ligands show inverse relationships with respect to normal bone marrow PC. Furthermore, the two genes also tend to be inversely correlated within the patient population.

Recent studies have shown that rat Wnt5a is a ligand for Rfz2 (FZD2) and that binding of the ligand to receptor signals through phosphodiesterase and cyclic GMP (Ahumada et al., 2002). Correlation analysis of the expression of FZD2 and WNT5A in PC from 222 newly diagnosed patients has shown that PC with low FZD2 tend to have high expression of WNT5A and those with high FZD2 to have low WNT5A levels. One possible explanation for this phenomenon is that normal PC utilizes the FZD2 signaling pathway and that down-regulation of FZD2, an apparent early event in MM, results in a compensatory up-regulation of WNT5A.

Yamanaka et al. have recently shown that Wnt5a is also capable of activating JNK in cultured cells, and that the JNK pathway mediates the action of Wnt5a to regulate convergent extension movements, a vertebrate correlate of the planar cell polarity pathway of Drosophila (Yamanaka et al., 2002). Lisovsky and colleagues have also shown that Xenopus Frizzled 8 (Xfz8) activates JNK and triggers rapid apoptotic cell death in gastrulating Xenopus embryos (Lisovsky et al., 2002). They showed that the apoptotic signaling was shared by a specific subset of Frizzled receptors, was inhibited by Wnt5a, and occurred in a Dishevelled- and T cell factor (TCF)-independent manner (Lisovsky et al., 2002). These data suggests that WNT5A over-expression in MM may prevent apoptosis through inhibition of JNK signaling. Hideshima et al. have demonstrated that the proteasome inhibitor PS-341 activates JNK, that this activation is correlated with MM cell apoptosis, and that blocking JNK activation abrogates PS-341-induced cell death (Hideshima et al., 2002). Thus it will be interesting to determine if MM cells cultured in the presence of excess WNT5A demonstrate resistance to PS-341-induced apoptosis.

Previous studies on the effects of Wnts in hematopoiesis suggests that alteration in the ratio of specific Wnt ligands, especially Wnt5A and Wnt10B, may have profound effects on normal bone marrow stem cell function (Austin et al., 1997). Brandon and colleagues have recently shown that treatment of hematopoietic progenitor cell-enriched bone marrow cultures with soluble WNT11 or WNT5a inhibited macrophage formation and enhanced monocyte and RBC production (Van Den Berg et al., 1998). Thus, one of the consequences of elevated WNT5A in MM may be to drive progenitor cells to monocytes at the expense of macrophage development. This increased pool of monocytes, in the presence of osteoclast differentiation factors such as RANKL, could theoretically contribute to increased osteoclast numbers.

Van Den Berg and colleagues have demonstrated that Wnt-5A, Wnt-2B, and Wnt-10B are expressed in fetal bone stromal cells, that these genes are expressed to varying levels in hematopoietic cell lines derived from T cells, B cells, myeloid cells, and erythroid cells, but that only Wnt-5A is expressed in CD34(+)Lin-primitive progenitor cells (Van Den Berg et al., 1998). The authors also showed that the number of hematopoietic progenitor cells is markedly affected by exposure to stromal cell layers expressing Wnt genes. Colony formation by cells expanded on the Wnt-expressing co-cultures was similar for each of the three genes, indicating similar action on primitive progenitor cells; however, Wnt-10B showed differential activity on erythroid progenitors (BFU-E) compared with Wnt-5A and Wnt-2B (Van Den Berg et al., 1998). Co-cultures containing Wnt-10B alone or in combination with all three Wnt genes had threefold to fourfold lower BFU-E colony numbers than the Wnt-5A- or Wnt-2B-expressing co-cultures (Van Den Berg et al., 1998). The relationship of Wnt signaling and stromal cell-hematopoietic cell development has been furthered by studies showing that conditioned medium containing Wnt-3a dramatically reduced the production of B lymphocyte and myeloid lineages, except for macrophages, in long-term bone marrow cultures grown on stromal cells (Brandon et al., 2000). In contrast, the same conditioned medium did not affect the generation of these cells in stromal cell-free conditions. The authors took these results to suggest that Wnt proteins exert their effects through stromal cells and supported this hypothesis by showing that the same effects could be mimicked by the expression of a stabilized form of beta-catenin in stromal cells (Yamane et al., 2001).

Evidence for a direct role of Wnt signaling in B-cell biology and B-cell disease is derived from recent studies showing that Wnt signaling requires BCL9-mediated recruitment of pygopus to the nuclear β-catenin-TCF complex (Kramps et al., 2002). GEP data from 222 newly diagnosed MM and 45 normal bone marrow PC has revealed elevated expression of BCL9 in approximately one-third of MM (mean 2128; range 758 to 4735) when compared to normal PC (mean 1447; range 394 to 2305). Reya et al. have shown that mice deficient for lymphocyte enhancer factor-1 (LEF-1) exhibit defects in pro-B cell proliferation and survival in vitro and in vivo, that Lef1$^{-/-}$ pro-B cells display elevated levels of fas and c-myc transcription, and that Wnt proteins are mitogenic for pro-B cells and that this effect is mediated by Lef1 (Reya et al., 2000).

A role for WNT signaling in normal PC development is indicated by several observations. First, global GEP of human plasma cell differentiation revealed that whereas WNT10B is not expressed in tonsil BC, it is turned on in both tonsil and bone marrow PC (Zhan et al., 2003). In contrast, FRZB was significantly down-regulated in the transition of immature tonsil PC to mature bone marrow PC (Zhan et al., 2003). Secondly, Alexander et al. have demonstrated that syndecan-1 (CD138/SDC1), a transmembrane heparan sulfate proteoglycan expressed exclusively on mature plasma cells within the hematopoietic lineage, is required for Wnt-1-induced mammary tumorigenesis in mice (Alexander et al., 2000), suggests that one possible function for syndecan-1 in PC biology is to facilitate WNT signaling. Finally, a recent gene expression study of mouse plasma cell differentiation has shown that Axin and Frat1 are down-regulated in PC with respect to BC, whereas β catenin and disheveled were equally expressed in both cell types (Underhill et al., 2003).

EXAMPLE 24

Gene Expression Profiling before and after Short-Term Drug Treatment to Identify Potential Mechanisms of Action All current chemotherapy regimens for multiple myeloma (MM) treatment attempt to use combinations of multiple drugs affecting non-overlapping, and non-cross resistant pathways. It is impossible to define, in the context of these extensive combinations, the molecular mechanisms of action of individual components. Short-term serial gene expression studies of tumor cells after single agent drug treatment may provide insight into the mechanisms of action, especially when combined with clinical response data. This knowledge, if confirmed, can lead to the development of second-generation drugs with more effective response profiles and less toxicities. In addition, knowledge of pathways will allow development of drugs that target discrete points along pathways allowing use of complementary or synergistic drugs. Potential advantages of performing invivo studies are that drug metabolism, tumor cell host interactions, and drug response correlations can be considered.

In an effort to gain insight into the mechanism of action of various single-agent compounds, the inventors have performed baseline and 48-hour follow-up gene expression profiling (GEP) on patients before and after therapy with dexamethasone (n=20), thalidomide (n=18), the thalidomide derivative IMiD (n=15), or the proteasome inhibitor PS-341 (n=11) (Shaughnessy et al., 2002).

Based on the t-test for differences in quantitative expression changes, dexamethasone induced the greatest change (147 genes P<0.0001; 51 up and 96 down). PECAM1 was down-regulated in 20 of 20 cases and represented the most significantly altered gene (P=5.8×10–9) after dexamethasone treatment. PECAM1 is an adhesion molecule that is up-regulated as PC mature from the tonsil to bone marrow stage of development (Zhan et al., 2003), suggesting a critical role for this protein in PC adhesion to the bone marrow stroma. Thus, it is possible that down-regulation of PECAM1 may result in MM PC detachment and an increased rate of spontaneous or chemotherapy induced apoptosis.

Virtually all (18 of 20) cases treated with dexamethasone also showed down-regulation of the pro-angiogenic molecule VEGF and the anti-apoptotic molecule MCL1, both of which have been implicated in MM biology. Since VEGF is up-regulated upon adherence of MM cells to stroma, it is not clear whether VEGF down-regulation is directly caused by dexamethasone or is a reflection of the down-regulation of PECAM1 and detachment of the cells from stroma. Given that most patients initially respond to dexamethasone treatment, but eventually develop resistance, performing GEP on patients after treatment with dexamethasone that are known to be resistant to the drug might provide insight into the mechanisms of action. For example, it may be found that dexamethasone resistant MM PC may not down-regulate PECAM1 and VEGF after short-term treatment.

Surprisingly, using the same t-test analysis, PS-341 only induced significant changes in 9 genes (P<0.001; 2 up and 7 down). The down-regulation of the Cockayne syndrome 1 gene (CKN1) represented the most significant change (P=6× 10–6) after PS-341 treatment. CKN1 encodes a WD repeat protein that interacts with CSB protein and a subunit of RNA polymerase II TFIIH and mutations of CKN1 are associated defective strand-specific repair of transcriptionally active genes. Thus, the down-regulation of CKN1 by PS-341 may have negative effects on RNA polymerase II transcription and may explain the low number of altered genes relative to dexamethasone, thalidomide, and IMiD. A possible mechanism of action of the drug may be to impair DNA damage repair through the down-regulation of CKN1. In such a scenario inactivation of CKN1 could result in cells with germ line TP53 being driven into an apoptotic program rather than a DNA repair pathway. Such a scenario, if true, suggests that combining PS-341 with alkylating agents may have synergistic effects.

IMiD or CC-5013, a potent thalidomide analog, induced changes in 98 genes (P<0.001; 41 up and 57 down), whereas thalidomide induced significant changes in 57 genes (P<0.001; 29 up and 28 down). Given that IMiD and thalidomide are related molecules, it is speculated that consistent and common changes in gene expression influenced by both drugs might point to mechanisms of action. Seven genes, CROT, IL6, TPBG, ALB, PLSCR1 and, DKK1 were activated by both drugs with up-regulation after IMiD treatment being more pronounced for all genes, attesting to the higher potency of the derivative. Importantly, Dickkopf1 (DKK1), a secreted antagonist of Wnt signaling, was hyperactivated a median of 125% in 14 of 18 patients treated with thalidomide and up-regulated a median of 315% in 13 of 15 cases treated with IMiD. Virtually all MM cases not showing a hyperactivation of DKK1 after treatment with both drugs had little or no detectable expression in the baseline sample, suggesting that these cases had an inherent inability to activate DKK1 expression. Along these lines it was also noted that whereas DKK1 was expressed in nearly 80% of newly diagnosed MM, virtually all cases of PC leukemia and plural effusions from end stage M M lack expression of DKK1. Given that DKK1 is a direct target of p53 and p53 loss is frequently seen in late stage MM, it is possible that the lack of expression and/or inability to activate DKK1 in MM may be due to loss of p53. In fact, one of the cases of newly diagnosed MM that showed no DKK1 at baseline or after 48 hr treatment with thalidomide was primary refractory to all interventions. The p53 status in this patient was not known.

Of 648 genes exhibiting a greater than 50% (range 51% to 408%) change in median expression level after IMiD treatment, DKK1, at 315% increase ranked as the 4$^{th}$ most significantly altered gene. In a similar analysis after thalidomide treatment, DKK1 was ranked 13$^{th}$ out of 217 genes. Conversely, although hyperactivated in 14 of 20 patients, DKK1 only showed a median increase of 23%, was ranked 1426$^{th}$ and not represented in the list of 280 genes exhibiting an up-regulation of at least 50% (range 51% to 470%) by dexamthasone. The effects of PS-341 were even more skewed from the IMiD and thalidomide data in that only 7 of 15 patient samples exhibited increases in DKK1 and the median change was essentially undetectable at −1.60%. DKK1 ranked 7,532 of 12,000 genes tested. Thus, these data provide the first evidence that for the in vivo effects of drug treatment on DKK1 expression, thalidomide and IMiD have powerful up-regulating effects; dexamethasone has an intermediate effect; and the proteasome inhibitor PS-341 has little or no effect.

It is important to determine if the drug has a direct activating effect or whether the increase really reflects the rapid and preferential killing of cells not expressing DKK1 which would in turn create a virtual up-regulation. Several points argue against the latter possibility. First, DNA damaging agents like UV irradiation, $H_2O_2$, cisplatin, and BCNU activate DKK1 in vitro and this activation sensitizes cells to apoptosis. Second, it is unlikely that a massive cell kill occurred within 48 hours after in vivo administration. Finally, the inventos have recently found that in vitro treatment of the human MM cell line ARP1 with thalidomide, IMiD, and dexamethasone results in the activation of DKK1.

Given the fact that in vitro DNA damage triggers DKK1 expression, it is speculated that DNA instability present in MM PC may be a trigger of DKK1 activation in newly diagnosed, previously untreated cases of MM. Thus, DKK1 not only could be a major mediator of MM PC cell death after drug treatment, but also a mediator of apoptosis in these cells as a result of endogenous DNA damage. Indirect support for a role for DKK1 in M M cell apoptosis comes from previous studies showing that 1) DKK1 is activated by BMP-4, and 2) that treatment of MM cell lines and primary MM samples with BMP-4 can inhibit proliferation and induce apoptosis. These data suggests that one possible mechanism of BMP-4 induced MM PC killing is through the activation of DKK1.

DKK1 has been shown to be critical for limb morphogenesis during vertebrate embryogenesis. DKK1 null mutant embryos show duplications and fusions of limb digits whereas forced over expression of DKK1 in embryonic limb buds inhibits limb outgrowth. The limb defects resulting from over expression of DKK1 have a strong resemblance to the limb defects seen in thalidomide embryopathy. Thus, an intriguing implication of the link between thalidomide and DKK1 activation is that disruption of WNT signaling through DKK1 activation by thalidomide may be the long sought mechanism by which thalidomide causes such limb malformations. Interestingly, a link between DKK1 expression and MM-specific bone defects has become apparent through the use of microarray profiling (see above).

Thus, in vivo monitoring of gene expression changes following single agent drug treatment appears to be a feasible approach to study the effect of treatment and molecular mechanisms of action. These types of study have powerful advantages over in vitro studies of the same design, in that response, tumor cell host interactions, and non-tumor cell effects (variables that cannot be faithfully recapitulated in model systems) can be taken into account.

The following references are cited herein:

Ahumada et al., Signaling of rat Frizzled-2 through phosphodiesterase and cyclic GMP. *Science* 298:2006-10 (2002).

Alexander et al., Syndecan-1 is required for Wnt-1-induced mammary tumorigenesis in mice. *Nat. Genet.* 25:329-32 (2000).

Austin et al., A role for the Wnt gene family in hematopoiesis: expansion of multilineage progenitor cells. *Blood* 89:3624-35 (1997).

Brandon et al., WNT signaling modulates the diversification of hematopoietic cells. *Blood* 96:4132-41 (2000).

Brown et al., Support vector machine classification of microarray gene expression data. UCSC-CRL 99-09, Department of Computer Science, University California Santa Cruz, Santa Cruz, Calif. (1999).

Chauhan et al., Identification of genes regulated by Dexamethasone in multiple myeloma cells using oligonucleotide arrays. *Oncogene* 21:1346-1358 (2002).

Cheng et al., KDD Cup 2001. *SIGKDD Explorations* 3:47-64 (2000).

Cristianini and Shawe-Taylor, An Introduction to Support Vector Machines and other kernel-based learning methods. Cambridge University Press (2000).

De Vos et al., Identifying intercellular signaling genes expressed in malignant plasma cells by using complementary DNA arrays. *Blood* 98:771-80 (2001).

Eisen et al., Cluster analysis and display of genome-wide expression patterns. *Proc Natl Acad Sci* USA 95:14863-14868 (1998).

Friedman et al., Learning Bayesian network structure from massive datasets: the "sparse candidate" algorithm. *Proceedings of the International Conference on Uncertainty in Artificial Intelligence* (1999).

Furey et al., Support vector machine classification and validation of cancer tissue samples using microarray expression data. *Bioinformatics* 16:906-914 (2000).

Gallea et al., Activation of mitogen-activated protein kinase cascades is involved in regulation of bone morphogenetic protein-2-induced osteoblast differentiation in pluripotent C2C12 cells. *Bone* 28:491-8 (2001).

Hideshima et al., Molecular mechanisms mediating anti-myeloma activity of proteasome inhibitor PS-341. *Blood* (2002).

International Human Genome Sequencing Consortium, Initial sequencing and analysis of the human genome. *Nature* 409:860-921 (2001).

Kohavi, A study of cross-validation and bootstrap for accuracy estimation and model selection. *Proceedings of the International Joint Conference on Artificial Intelligence* (IJCAI) (1995).

Kramps et al., Wnt/wingless signaling requires BCL9/legless-mediated recruitment of pygopus to the nuclear beta-catenin-TCF complex. *Cell* 109:47-60 (2002).

Li and Wong, Model-based analysis of oligonucleotide arrays: expression index computation and outlier detection. *Proc Natl Acad Sci* USA 98:31-36 (2001).

Lisovsky et al., Frizzled receptors activate a novel JNK-dependent pathway that may lead to apoptosis. *Curr. Biol.* 12:53-8 (2002).

Murphy, The Bayes Net Toolbox for Matlab. *Computing Science and Statistics: Proceedings of the Interface*, (2001).

Pe'er et al., Inferring Subnetworks from Perturbed Expression Profiles. *Proceedings of the Ninth International Conference on IntelligentSystems for Molecular Biology* (2001).

Reya et al., Wnt signaling regulates B lymphocyte proliferation through a LEF-1 dependent mechanism. *Immunity* 13:15-24 (2000).

Shaughnessy et al., High incidence of chromosome 13 deletion in multiple myeloma detected by multiprobe interphase FISH. *Blood* 96:1505-1511 (2000).

Shaughnessy et al., Gene expression profiling after short term in vivo treatment identifies potential mechanisms of action of current drugs used to treat multiple myeloma. *Blood* 100:781a (2002).

Spinella-Jaegle et al., Opposite effects, of bone morphogenetic protein-2 and transforming growth factor-beta1 on osteoblast differentiation. *Bone* 29:323-30 (2001).

Tarte et al., Generation of polyclonal plasma cells from peripheral blood B cells: a normal counterpart of malignant plasma cells. *Blood* In press (2002).

Underhill et al., Gene expression profiling reveals a highly specialized genetic program of plasma cells. *Blood* (2003).

Van Den Berg et al., Role of members of the Wnt gene family in human hematopoiesis. *Blood* 92:3189-202 (1998).

Vapnik, Statistical Learning Theory. John Wiley & Sons (1998).

Venter et al., The sequence of the human genome. *Science* 291:1304-51 (2001).

Yaccoby et al., Significant and consistent gene expression changes highlight the molecular consequences of myeloma and normal donor plasma cell interactions with osteoclasts. *Blood* 100: 2392a (2002).

Yamanaka et al., JNK functions in the non-canonical Wnt pathway to regulate convergent extension movements in vertebrates. *EMBO* 3:69-75 (2002).

Yamane et al., Wnt signaling regulates hemopoiesis through stromal cells. *J Immunol* 167:765-72 (2001).

Zhan et al., Global gene expression profiling of multiple myeloma, monoclonal gammopathy of undetermined significance, and normal bone marrow plasma cells. *Blood* 99:1745-1757 (2002a).

Zhan et al., Gene expression profiling of multiple myeloma plasma cells allows identification of potential molecular determinants of lytic bone disease. *Blood* 100: 782a (2002b).

Zhan et al., Gene expression profiling of human plasma cell differentiation and classification of multiple myeloma based on similarities to distinct stages of late stage B-cell development. *Blood* 101:1128-1140 (2003).

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

What is claimed is:

1. A method of diagnosis for multiple myeloma, comprising the steps of:
   isolating plasma cells from an individual;
   examining expression of a group of 14 genes within said plasma cells, said 14 genes identified by SEQ ID NO. 1, SEQ ID NO. 2, SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11, SEQ ID NO. 12, SEQ ID NO. 13 and SEQ ID NO. 14,
   performing statistical analysis on the expression levels of said genes, wherein a statistically significant value, representing collectively the expression levels of said genes, of said analysis indicates that said individual has multiple myeloma.

2. The method of claim 1, wherein the expression of said 14 genes is examined at the nucleic acid level or protein level.

* * * * *